(12) United States Patent
Chen et al.

(10) Patent No.: US 11,208,653 B2
(45) Date of Patent: Dec. 28, 2021

(54) INCREASING RNAI EFFICIENCY THROUGH SINGLE NUCLEOTIDE MISMATCHES

(71) Applicant: Whitehead Institute for Biomedical Research, Cambridge, MA (US)

(72) Inventors: Grace Chen, Somerville, MA (US); David Bartel, Brookline, MA (US); Hazel Sive, Newton, MA (US)

(73) Assignee: Whitehead Institute for Biomedical Research, Cambridge, MA (US)

(*) Notice: Subject to any disclaimer, the term of this patent is extended or adjusted under 35 U.S.C. 154(b) by 0 days.

(21) Appl. No.: 16/097,179

(22) PCT Filed: Apr. 27, 2017

(86) PCT No.: PCT/US2017/029972
§ 371 (c)(1),
(2) Date: Oct. 26, 2018

(87) PCT Pub. No.: WO2017/189927
PCT Pub. Date: Nov. 2, 2017

(65) Prior Publication Data
US 2021/0130819 A1    May 6, 2021

Related U.S. Application Data

(60) Provisional application No. 62/328,589, filed on Apr. 27, 2016.

(51) Int. Cl.
*C12N 15/113*    (2010.01)
(52) U.S. Cl.
CPC ........ *C12N 15/113* (2013.01); *C12N 2310/14* (2013.01); *C12N 2320/50* (2013.01)

(58) Field of Classification Search
None
See application file for complete search history.

(56) References Cited

U.S. PATENT DOCUMENTS

2007/0259827 A1* 11/2007 Aronin .................... A61P 25/28
                                                      514/44 A
2011/0223665 A1    9/2011 Maier et al.

OTHER PUBLICATIONS

Amarzguioui et al. Nucleic Acids Research 2003, vol. 31, pp. 589-595.*
Elabshir et al. EMBO Journal 2001, vol. 20, pp. 6877-6888.*
Huang, Huang, et al. "Profiling of mismatch discrimination in RNAi enabled rational design of allele-specific siRNAs." Nucleic Acids Research 37.22 (2009): 7560-7569.
Cognet, J. A. H., et al. "Soloution conformation of an olionucleotide containing a GG mismatch determined by nuclear manetic resonance and molecular mechanics." Nucleic Acids Research 19.24 (1991): 6771-6779.
International Search Report from International Application No. PCT/US2017/029972, dated Nov. 9, 2017.

* cited by examiner

*Primary Examiner* — Tracy Vivlemore
(74) *Attorney, Agent, or Firm* — Morse, Barnes-Brown & Pendleton, P.C.; Lisa M. Warren, Esq.; Erin E. Bryan, Esq.

(57) ABSTRACT

Methods and compositions for increasing RNAi efficiency through single nucleotide mismatches.

7 Claims, 25 Drawing Sheets
(22 of 25 Drawing Sheet(s) Filed in Color)
Specification includes a Sequence Listing.

1C

1D 2D
(SEQ ID NOs: 42-52)
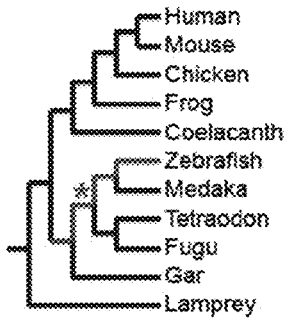
2E
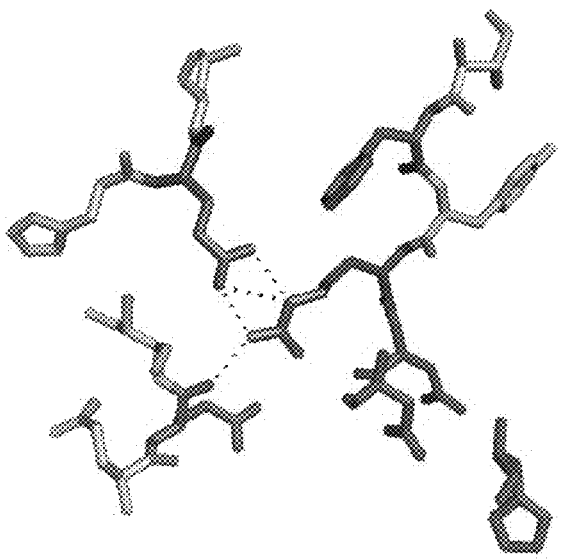
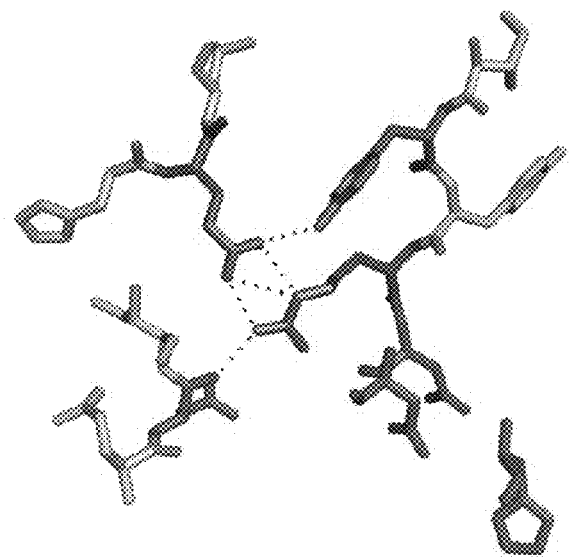
FIGS. 2D-2E

Ancestral pre-miR-451 (G-G)

```
 U              G     CU
U  UAGUAAUGGUAA GGUU    G      SEQ ID NO: 53
G  GUCAUUACCAUU CCAA           SEQ ID NO: 54
 A              G     A*
```

Amniote pre-miR-451 (G-C)

```
 U                    CU
U  UAGUAAUGGUAACGGUU    G      SEQ ID NO: 55
G  GUCAUUACCAUUGCCAA           SEQ ID NO: 56
 A                    A*
```

5B 6A (SEQ ID NOs: 42-52)

6B

7A

7B

INCREASING RNAI EFFICIENCY THROUGH SINGLE NUCLEOTIDE MISMATCHES

RELATED APPLICATIONS

This application is a national stage filing under 35 U.S.C. 371 of International Application No. PCT/US2017/029972, filed Apr. 27, 2017, which claims the benefit of U.S. Provisional Application No. 62/328,589, filed Apr. 27, 2016, the entire teachings of which are incorporated herein by reference.

GOVERNMENT SUPPORT

This invention was made with government support under Grant No. R37 GM061835 awarded by the National Institutes of Health. The government has certain rights in the invention.

BACKGROUND OF THE INVENTION

Diverse RNA-silencing pathways play important roles in transposon silencing, viral defense, heterochromatin formation, and posttranscriptional repression of cellular genes (Bartel, 2004; Farazi et al., 2008; Malone and Hannon, 2009; Moazed, 2009; Tomari and Zamore, 2005). The simplest of these pathways is RNA interference (RNAi), in which the Dicer endonuclease cleaves long, double-stranded RNA (dsRNA) into small interfering RNAs (siRNAs) that are loaded into an Argonaute (Ago) protein to form an RNA-induced silencing complex (RISC), which cuts (i.e., slices) transcripts that have extensive pairing to the siRNA (Farazi et al., 2008; Tomari and Zamore, 2005). The RNA silencing pathways each include at their core a silencing complex that contains a short (20-32-nt) RNA associated with an Argonaute homolog (Bartel, 2004; Farazi et al., 2008; Malone and Hannon, 2009; Moazed, 2009; Tomari and Zamore, 2005). Within this complex the RNA provides specificity as it pairs to target transcripts, and the Argonaute homolog either slices the target precisely between the nucleotides that pair to residues 10 and 11 of the guide RNA or recruits other proteins to promote other types of repression. More efficient methods of targeting and slicing target transcripts using RNAi are desired.

SUMMARY OF THE INVENTION

In some embodiments, the present inventions are directed to siRNAs comprising a guide sequence with at least one mismatch with respect to a target sequence.

In some embodiments, the present inventions are directed to methods of using an siRNA to modulate expression levels of at least one target having a target sequence, comprising contacting a target with an siRNA having a guide sequence with at least one mismatch with respect to the target sequence, thereby modulating expression levels of the target.

In some embodiments, the present inventions are directed to methods of using an oligonucleotide to modulate expression levels of at least one target having a target sequence, comprising contacting a target with an oligonucleotide having a guide sequence with at least one mismatch with respect to the target sequence, thereby modulating expression levels of the target In some embodiments, the guide sequence mismatch with respect to the target sequence is located within nucleotides 2 to 7 of the guide sequence. For example, the guide sequence mismatch with respect to the target sequence may be located at guide position 6 of the guide sequence. In some embodiments, the guide sequence has no more than one mismatch with respect to the target sequence. In some embodiments, the guide sequence mismatch with respect to the target sequence is selected from the group consisting of a G-G mismatch, a G-A mismatch, and a G-U mismatch. In other embodiments, the guide sequence mismatch with respect to the target sequence is selected from the group consisting of a A-A mismatch, a A-G mismatch, and a A-C mismatch. In some embodiments, the guide sequence mismatch with respect to the target sequence is selected from the group consisting of a U-U mismatch, a U-G mismatch, and a U-C mismatch. In still other embodiments, the guide sequence mismatch with respect to the target sequence is selected from the group consisting of a C-C mismatch, a C-A mismatch, and a C-U mismatch. In some embodiments, the guide sequence mismatch with respect to the target sequence is located at guide position 6 of the guide sequence, and is a G-G mismatch.

In some embodiments, the guide sequence mismatch with respect to the target sequence is designed in view of the target sequence. In some embodiments, the guide sequence mismatch with respect to the target sequence is intentionally inserted in view of the target sequence.

In some embodiments, the siRNA or oligonucleotide is administered to an organism (e.g., a mammal, a human, etc.) in a therapeutically effective amount. In some embodiments, the siRNA reduces expression of the target by at least 50%, by at least 75% or by at least 90%. In some embodiments, the modulation of expression levels of the at least one target results in treatment of a condition associated with aberrant expression of the at least one target.

In some embodiments, the siRNA comprising a guide sequence having a mismatch with respect to the target sequence exhibits increased target binding compared to a siRNA comprising a guide sequence not having a mismatch with respect to the target sequence. In other embodiments, the siRNA comprising a guide sequence having a mismatch with respect to the target sequence exhibits increased target slicing compared to a siRNA comprising a guide sequence not having a mismatch with respect to the target sequence.

In some embodiments, the present inventions are directed to the use of the siRNAs as described here for the treatment of a condition associated with aberrant expression of a target.

In some embodiments, the present inventions are directed to methods of treating a condition associated with aberrant expression of a target, comprising selecting a patient diagnosed with said condition and administering to said patient the siRNA described here.

In some embodiments, the present inventions are directed to pharmaceutical compositions comprising an siRNA which is useful for the treatment of a condition, wherein said siRNA comprises a guide sequence having at least one mismatch with respect to a target sequence.

In some embodiments, the present inventions are directed to methods of treating a mammal (e.g., a human) suffering from a condition, the method comprising administering to the mammal a therapeutically effective amount of an siRNA targeted to a target gene having a target sequence, wherein the siRNA comprises a guide sequence having a mismatch with respect to the target sequence.

In some embodiments, the siRNA is administered parenterally. In some embodiments, the siRNA is administered intravenously. In some embodiments, the siRNA is administered by bolus injection into a target organ or tissue. In some embodiments, the siRNA is administered intraperitoneally. In some embodiments, the siRNA is administered subcutaneously.

Also disclosed herein are teleost cells that comprise a nucleic acid that encodes an Argonaute polypeptide that has increased target slicing ability as compared to the Argonaute2 (Ago2) polypeptide that is native to the cell.

In some embodiments, the cell is a zebrafish cell. In some embodiments, the nucleic acid is operably linked to an expression control element capable of directing transcription in the teleost cell. In some embodiments, the expression control element comprises an inducible promoter that is functional in the cell. In some embodiments, the nucleic acid is a DNA segment that is integrated into the genome of the cell.

In some embodiments, the nucleic acid is the native Ago2 gene of the cell but has been genetically modified to encode an Ago polypeptide having a glutamate at the position corresponding to position 16 of SEQ ID NO: 1, a phenylalanine at the position corresponding to position 45 of SEQ ID NO: 1, or both. In some embodiments, the nucleic acid encodes a variant of the Ago2 polypeptide that is native to the cell, wherein the variant Ago2 polypeptide has a glutamate at the position corresponding to position 16 of SEQ ID NO: 1, a phenylalanine at the position corresponding to position 45 of SEQ ID NO: 1, or both.

In some embodiments, the nucleic acid encodes a polypeptide that is at least 90%, at least 95%, at least 96%, at least 97%, at least 98%, at least 99%, or more identical to a naturally occurring Ago2 polypeptide, and in some aspects the polypeptide encoded by the nucleic acid has a glutamate at the position corresponding to position 16 of SEQ ID NO: 1, a phenylalanine at the position corresponding to position 45 of SEQ ID NO: 1, or both. In some embodiments, the nucleic acid encodes a mammalian, avian, amphibian, reptile, coelacanth, or non-teleost fish Ago2 polypeptide.

In some embodiments, the cell further comprises (i) a non-endogenous nucleic acid segment that can be transcribed to yield a shRNA that has sequence complementarity to mRNA of a gene; or (ii) a siRNA. In certain embodiments, the non-endogenous nucleic acid segment is operably linked to an expression control element capable of directing transcription in the cell. In certain embodiments, the expression control element comprises an inducible promoter. In certain embodiments, the nucleic acid segment that can be transcribed to yield a shRNA is integrated into the genome of the cell. In certain embodiments, the gene is an endogenous gene of the cell.

In some embodiments, the Argonaute polypeptide is at least 90%, at least 95%, at least 96%, at least 97%, at least 98%, at least 99%, or more identical to a naturally occurring Ago2 polypeptide. In certain embodiments, the Argonaute polypeptide is identical to a naturally occurring Ago2 polypeptide. In some embodiments, the naturally occurring Ago2 polypeptide is encoded by a nucleic acid having an accession number listed in Table 1.

Also disclosed herein, are genetically modified teleosts. The genetically modified teleosts comprise at least one cell as described here. Also disclosed herein, are genetically modified teleosts comprising cells that comprise a nucleic acid that encodes an Argonaute polypeptide that has increased target slicing ability as compared to the Ago2 polypeptide that is native to the teleost.

In some embodiments, the present inventions are directed to genetically modified teleosts in which one allele or both alleles of the native Ago2 gene has been modified to encode an Ago2 polypeptide that has a glutamate at the position corresponding to position 16 of SEQ ID NO: 1, a phenylalanine at the position corresponding to position 45 of SEQ ID NO: 1, or both. In some embodiments, the present inventions are directed genetically modified teleosts in which at least 90%, at least 95%, at least 99%, or more of the cells express an Ago2 polypeptide that is native to a non-teleost organism, optionally wherein the non-teleost organism is a non-teleost fish, a mammal, or a bird. Also disclosed herein, are genetically modified teleosts in which at least 90%, at least 95%, at least 99%, or more of the cells express a polypeptide that is at least 90%, at least 95%, at least 96%, at least 97%, at least 98%, at least 99%, or more identical to a naturally occurring Ago2 polypeptide.

In some embodiments, the teleost is a zebrafish.

In some embodiments, the present inventions are directed to nucleic acids that encodes a polypeptide that is at least 95%, at least 96%, at least 97%, at least 98%, at least 99%, or more identical to a teleost Ago2, wherein the polypeptide has a glutamate at the position corresponding to position 16 of SEQ ID NO: 1, a phenylalanine at the position corresponding to position 45 of SEQ ID NO: 1, or both, wherein the polypeptide comprises a sequence that is not found in nature.

Also disclosed herein are expression vectors comprising the nucleic acids as described here.

In some embodiments, a cell comprises the nucleic acid or vector described here. In optional embodiments, the cell is a teleost cell. In additional optional embodiments, the nucleic acid or vector is integrated into the genome of the cell.

Also disclosed herein are polypeptides that are at least 95%, at least 96%, at least 97%, at least 98%, at least 99%, or more identical to a teleost Ago2, wherein the polypeptide has a glutamate at the position corresponding to position 16 of SEQ ID NO: 1, a phenylalanine at the position corresponding to position 45 of SEQ ID NO: 1, or both, wherein the polypeptide comprises a sequence that is not found in nature. In some embodiments, a cell comprises the polypeptide described here. In optional embodiments, the cell is a teleost cell. In further optional embodiments, the cell is a zebrafish cell.

Also disclosed herein are non-human organisms comprising the nucleic acid, expression vector, polypeptide or cells described here. In optional embodiments, the non-human organism is a teleost. In further optional embodiments, the teleost is a zebrafish.

In some embodiments, the present inventions are directed to methods of producing a genetically modified teleost cell that has an increased target slicing ability as compared to an otherwise identical non-genetically modified teleost cell the method comprising: (a) providing a teleost cell; and (b) modifying the teleost cell so as to cause it to express an Argonaute polypeptide that has increased target slicing ability as compared to the Argonaute2 (Ago2) polypeptide that is native to the cell.

In some embodiments, step (b) comprises introducing into the teleost cell a nucleic acid that comprises a sequence that encodes the Argonaute polypeptide, wherein the sequence that encodes the Argonaute polypeptide is operably linked to an expression control element capable of directing transcription in the teleost cell. In alternative embodiments, step (b) comprises modifying at least one allele of the endogenous Ago2 gene in the cell so that it encodes an Argonaute polypeptide that has increased target slicing ability as compared to the Ago2 polypeptide that is native to the cell. In some embodiments, the Argonaute polypeptide comprises the polypeptide described here. In some embodiments, the Argonaute polypeptide is native to a non-teleost, optionally wherein the Argonaute polypeptide is a mammalian or avian Ago2 polypeptide.

In some embodiments, the present inventions are directed to methods of inhibiting expression of a target sequence in a teleost cell comprising: (a) providing a teleost cell described here; and (b) contacting the cell with a siRNA comprising a guide strand that is complementary to the target sequence. Also disclosed herein, are methods of inhibiting expression of a target sequence in a teleost cell comprising: (a) providing a teleost cell described here; and (b) expressing a shRNA comprising a guide strand that is complementary to the target sequence in the cell.

In some embodiments, the guide strand comprises a mismatch with respect to the target sequence, wherein the mismatch is located within nucleotides 2 to 7 of the guide sequence. In optional embodiments, the mismatch is located at position 6. In some embodiments, the mismatch is a G-G mismatch.

In some embodiments, the present inventions are directed to methods of inhibiting expression of a target sequence in a teleost comprising: (a) providing a teleost as described here; and (b) contacting the teleost with a siRNA comprising a guide strand that is complementary to the target sequence. Also disclosed herein are methods of inhibiting expression of a target sequence in a teleost comprising: (a) providing a teleost as described here; and (b) expressing a shRNA comprising a guide strand that is complementary to the target sequence in one or more cells of the teleost.

In some embodiments, the present inventions are directed to methods of examining the function of a gene in a teleost cell comprising: (a) providing a teleost cell as described here; (b) contacting the cell with a siRNA comprising a guide strand that is complementary to the target sequence; and (c) observing at least one phenotype of the cell, thereby examining the function of the gene. Also disclosed herein are methods of examining the function of a gene in a teleost cell comprising: (a) providing a teleost cell as described here; (b) expressing a shRNA comprising a guide strand that is complementary to the target sequence in one or more cells of the teleost; and (c) observing at least one phenotype of the cell, thereby examining the function of the gene.

In some embodiments, the present inventions are directed to methods of examining the function of a gene in a teleost comprising: (a) providing a teleost cell as described here; (b) contacting the teleost with a siRNA comprising a guide strand that is complementary to the target sequence; and (c) observing at least one phenotype of the teleost, thereby examining the function of the gene. Also disclosed herein are methods of examining the function of a gene in a teleost comprising: (a) providing a teleost as described here; (b) expressing a shRNA comprising a guide strand that is complementary to the target sequence in one or more cells of the teleost; and (c) observing at least one phenotype of the cell, thereby examining the function of the gene.

In some embodiments, the target sequence is or encodes a homolog of a mammalian sequence characterized in that mutation of, or altered expression or activity of, the mammalian sequence is associated with a condition. In some embodiments, inhibition of the target sequence results in a phenotype that corresponds to a phenotype characteristic of a mammalian condition.

In some embodiments, the methods further comprise contacting the teleost cell or teleost with a test agent and evaluating the effect of the agent on the phenotype of the teleost or teleost cell. In some embodiments, the methods further comprise identifying the test agent as a candidate therapeutic agent for treating the condition if the test agent reduces the severity of the phenotype.

In some embodiments, the guide strand comprises a mismatch with respect to the target sequence, wherein the mismatch is located within nucleotides 2 to 7 of the guide sequence. In optional embodiments, the mismatch is located at position 6. In some embodiments, the mismatch is a G-G mismatch. In some embodiments, the teleost cell is a zebrafish cell or the teleost is a zebrafish.

The above discussed, and many other, features and attendant advantages of the present inventions will become better understood by reference to the following detailed description of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A is a schematic of the protocol for assaying slicing in vivo. A 500 nt RNA with a site that perfectly paired to miR-430 was injected into single-cell embryos, with or without mRNA encoding additional Ago2. Total RNA was extracted at 4 hpf and analyzed on an RNA blot. FIG. 1B shows a comparison of slicing activity observed with either no added Ago (−), added drAgo2, or added hsAGO2. Shown is an RNA blot probing for an injected target with or without a perfectly complementary site (perfect site and 10-11 mm, respectively) and with or without mRNA encoding the indicated Ago2 protein. The percentage of product is indicated below each lane. FIG. 1C is a schematic of the protocol for assaying pre-miR-451 binding and cleavage. Pre-miR-451 with a labeled 5'-terminus (asterisk) was co-injected into single-cell embryos with mRNA for tagged Ago2. RNA co-purifying with Ago2 at 4 hpf was extracted and analyzed on a denaturing gel. FIG. 1D shows a comparison of pre-miR-451 binding and cleavage observed for either tagged drAgo2 or tagged hsAGO2 in zebrafish embryos. Shown is a phosphorimage of a denaturing polyacrylamide gel that resolved 5'-end-labeled pre-miR-451 substrate and products co-purifying with each of the indicated tagged Ago2 proteins. Below each lane is the percentage of labeled RNA in the form of cleaved product, including the mature miRNA and the cleaved, but either non-resected or partially resected, intermediates (diagramed to the right of the gel; asterisk, 5' label).

FIGS. 2A-2G depict restoring slicing activity to drAgo2. FIG. 2A shows the design of constructs that swapped the N-domains of hsAGO2 and drAgo2, with a summary of the slicing and pre-miR-451 processing activities observed for each construct (right). FIG. 2B shows a comparison of slicing activity observed with either no added Ago2 (−) or with mRNAs that introduced the Ago2 constructs described in panel A. Assays were as in FIG. 1B. FIG. 2C shows a comparison of pre-miR-451 binding and cleavage observed for the Ago2 constructs described in panel A. Assays were as in FIG. 1D. FIG. 2D is a cladogram (left) and multiple-sequence alignment (right) comparing a short region of the Ago2 PIWI domain from the indicated species. The segments of the jawed-fish lineage originally under consideration for the loss of Ago2 slicing activity are highlighted in red. Residues that were identical in Sarcopterygii and lamprey, but different in zebrafish, and were thus initial candidates for conferring the loss of slicing activity are in blue.

Other residues that varied in between these species are in bold. The two substitutions that were the prime candidates for conferring the loss of slicing are shaded in red in the alignment, with the most parsimonious point of their occurrence indicated with an asterisk in the cladogram. FIG. 2E shows amino acid changes proposed to explain the loss of efficient slicing in zebrafish modeled within the hsAGO2 structure (Schirle and MacRae, 2012), substituting the human residues (top) with the zebrafish residues (bottom). The residues of the catalytic tetrad are highlighted in green, showing part of the hydrogen-bond network proposed to position the active-site glutamate (dashed lines) (Nakanishi et al., 2012). This glutamate changes to an aspartate in zebrafish (green residues at the bottom left of each panel), whereas a nearby phenylalanine changes to a tyrosine (purple residues at the top of each panel), which might add to and perturb the hydrogen-bond network. FIG. 2F shows the effects of restoring the ancestral residues on the slicing activity of drAgo2. Assays were as in FIG. 1B. The graph plots mean cleavage from three experiments (error bars, standard deviation). FIG. 2G shows the effects of restoring the ancestral residues on the pre-miR-451-processing activity of drAgo2. Assays were as in FIG. 1D. The graph plots mean cleavage from three experiments (error bars, standard deviation). The dotted line across the plot indicates the average product observed with the Ago2$^{D-A}$ active-site mutants (FIG. 1D).

FIGS. 3A-3C depict ancestral G-G mismatch improves both pre-miR-451 cleavage and target slicing within zebrafish embryos. FIG. 3A shows sequences of ancestral and amniote pre-miR-451 hairpins. The G35C substitution that occurred in an amniote ancestor is highlighted in red. FIG. 3B is a comparison of binding and cleavage observed for the ancestral (G-G) and amniote (G-C) pre-miR-451 hairpins. Assays and quantification were as in FIG. 2G, but with the indicated Ago2 proteins. As indicted at the side of the gel, the G35C substitution led to a mobility change in the substrate but not products (as the products lacked nucleotide 35). The dotted line across the plot indicates the average product observed with the Ago2$^{D-A}$ active-site mutants (FIG. 1D). FIG. 3C shows effects of a G-G mismatch involving guide position 6 on slicing activity in zebrafish embryos. Assays and quantification were as in FIG. 2F.

FIG. 4A is a schematic showing the in vitro slicing reaction. 5'-cap-labeled target was incubated in reaction buffer with purified miR-430-programed Ago2 and then analyzed on a denaturing gel. FIG. 4B shows very different rates of in vitro slicing observed for the human and zebrafish proteins. These reactions were under single-turnover conditions (1 nM Ago2 and <0.1 nM target). Shown is a phosphorimage of a denaturing polyacrylamide gel that resolved cap-labeled target and sliced product after incubation with the indicated protein for the indicated time. Below each lane is the percentage of target converted to product, reporting the mean from two experiments for each time point ≤50 minutes. FIG. 4C shows multiple-turnover slicing reactions comparing a 150 nt target with a perfectly paired site (G-C target, top left) to one with a C-to-G substitution that placed a G across from the G at position 6 of miR-430 (G-G target, bottom left). Each target was cap-labeled and incubated in excess over miR-430-programed hsAGO2 (10 nM target, 1 nM hsAGO2, slicing buffer of Wee et al. 2012 but with 1.0 mM Mg$^+$, incubation at 37° C. for the indicated time). The graph on the right plots the results, with the two-phase least-squares fit to the data indicating $k_1$=0.94 min$^{-1}$ and $k_2$=0.19 min$^{-1}$ for the G-C target, and $k_1$=2.47 min$^{-1}$ and $k_2$=0.26 min$^{-1}$ for the G-G target.

FIG. 5A is a schematic of the in vivo miR-430-guided slicing assay. Capped target RNA is injected into one-cell embryos, where it becomes polyadenylated (pA) and encounters endogenous miR-430 loaded into either endogenous Ago2 or protein translated from a co-injected Ago2 mRNA. To the extent that Ago2 is capable, it slices the target at the site indicted (arrowhead). Injected embryos are allowed to develop until 4 hpf, at which point RNA is extracted and remaining target and sliced product are resolved and detected on an RNA blot. FIG. 5B shows slicing activities of zebrafish and human proteins in zebrafish embryos. Shown is an RNA blot probing for an injected target with or without a perfectly complementary miR-430 site (perfect site and 10-11 mm, respectively) and with or without co-injection of mRNA for the indicated protein. Below each lane is the percentage of total signal (target plus product bands) represented by product (% cleaved).

FIG. 6A is a cladogram (left) and multiple-sequence alignment (right) comparing a short region of the Ago2 PIWI domain from 11 vertebrate species. Segments of the jawed-fish lineage originally under consideration for the loss of drAgo2 slicing activity are highlighted (red). All residues that vary among these species are in bold, and those identical in Sarcopterygii and lamprey but different in zebrafish are in blue. The two substitutions that were the primary candidates for conferring the loss of slicing are shaded in red in the alignment, with the most parsimonious timing of their occurrence indicated with a red asterisk in the cladogram. FIG. 6B shows a structure of the Ago2 active-site residues and selected neighboring residues, modeling the amino acid changes (E-to-D and F-to-Y) that explain the loss of efficient slicing in zebrafish. Residues were modeled within the context of the hsAGO2 structure (Schirle and MacRae, 2012), substituting the ancestral residues of the human protein (top) with those of zebrafish (bottom). The residues of the catalytic tetrad, including the active-site E that changes to a D, are in green. Also shown is part of the hydrogen-bond network (dashed lines) that positions the E of the ancestral active-site and involves residues shown in blue (Nakanishi et al., 2012). The co-varying F-to-Y residue is in purple, with a potential additional hydrogen bond also shown, which might perturb the hydrogen-bond network in zebrafish. FIG. 6C shows the effect of restoring the ancestral residues on the slicing activity of drAgo2 in zebrafish embryos. Otherwise, this panel is as in FIG. 5B. The graph plots mean values from three experiments (error bars, standard deviation). FIG. 6D is a schematic of the in vitro slicing assay, which uses Ago2 that was affinity-purified based on both its association with miR-430 (green) and its 3×-FLAG tag (pink triangle). After binding to the purified complex, cap-labeled (red filled circle) target is sliced at the site indicated (arrowhead), and labeled product is resolved from target on a denaturing gel. FIG. 6E shows in vitro slicing activities of human and zebrafish proteins, and the effect of restoring the ancestral residues. Shown is a denaturing gel resolving cap-labeled target and product after incubation of limiting target (0.1 nM) with the indicated Ago2 protein (1.0 nM) for the indicated time. Below each lane is the percentage of target converted to product, reporting the mean from two experiments for each time point <500 minutes and the results of a single experiment for the 500-minute time points.

FIG. 7A is a schematic of the in vivo assay for pre-miR-451 binding and cleavage. End-labeled (red asterisk) pre-miR-451 and mRNA encoding a FLAG-tagged Ago2 protein are co-injected into zebrafish embryos at the one-cell stage. As the embryo develops, some pre-miR-451 is loaded into tagged Ago2 and cleaved at the site indicated (arrowhead), and some cleaved RNA is further resected to generate mature miR-451. At 4 hpf, embryos are lysed, and Ago protein translated from the injected mRNA is immunoprecipitated (IP) based on affinity to the 3x-FLAG tag (pink triangle). Co-immunoprecipitating RNAs, including loaded pre-miR-451, mature miR-451, and processing intermediates, are isolated and analyzed on a denaturing gel. FIG. 7B shows the ability of the zebrafish and human proteins to cleave pre-miR-451 in zebrafish embryos. Shown are results of binding-and-cleavage assays for the indicated proteins and their respective catalytically dead variants (D-to-A mutants). Each lane contained RNA co-immunoprecipitated from approximately 300 embryos. Below each lane is the percentage of the loaded pre-miR-451 that was cleaved (calculated using all cleaved species, including fully and incompletely resected cleavage products). FIG. 7C shows effects of restoring the ancestral residues to drAgo2 on pre-miR-451 binding and cleavage. Assays were as in (FIG. 7B), injecting mRNA for the indicated proteins. The graph plots mean values from two experiments (error bars, range). The dashed line represents the background activity, as determined from the cleavage observed for the active-site mutants in (FIG. 7B). FIG. 7D shows ancestral and amniote pre-miR-451 sequences, indicating residues of the mature miR-451 guide RNA (green), the site of Ago2-catalyzed cleavage (arrowhead), and the G-to-C change (blue and red, respectively) that creates a G-C match with miRNA position 6. FIG. 7E shows effects of the position-6 G-C match on pre-miR-451 binding and cleavage efficiency. Assays were as in (C), co-injecting mRNA for the indicated Ago2 proteins with either end-labeled ancestral (G-G) or amniote (G-C) pre-miR-451. The graph plots mean values from two experiments (error bars, range).

FIG. 9A shows effects of a position-6 G-G mismatch on multiple-turnover slicing by hsAGO2 in vitro. Assays were as in FIG. 8B except substrate (5 nM) was in excess over AGO2 (0.5 nM). Results for the G-C matched and G-G mismatched substrates are shown with filled and open symbols respectively, distinguishing the three replicates (circles, squares, triangles). The line for each substrate represents the best fit of the mean values to a biphasic reaction course (Wee et al., 2012), which generated the initial and steady-state rate constants ($k_1$ and $k_2$, respectively, shown ±95% confidence intervals). FIG. 9B is a schematic of the in vitro competitive binding and cleavage assay with long (168-nt) and short (80-nt) cap-labeled miR-430 targets.

FIG. 9C shows effect of the G-G mismatch on competitive binding and cleavage with hsAGO2 in vitro. Assays were as in FIG. 8B except substrates (2.5 nM each) were in excess over AGO2 (0.5 nM). For each substrate pair, the mean difference observed between the percent cleaved for long and short substrates is shown below the gel (fold difference), which was then normalized using the data from the left half of the gel to account for the differences observed for the same site in the long and short contexts (normalized fold difference). FIG. 9D is a model of Argonaute2-catalyzed cleavage of a G-G mismatch substrate compared to a G-C substrate, separating the binding, cleavage, and product release steps.

FIG. 10A shows activities of the zebrafish Ago proteins in zebrafish embryos. Assays were as in FIG. 1B, injecting mRNA for the indicated proteins. Slicing activity was not transferred to drAgo3a and drAgo3b, despite both possessing the full catalytic tetrad (DEDH); drAgo1 and drAgo4 were not tested as they had non-conservative substitutions in the catalytic tetrad (DEDR and DEGR, respectively). FIG. 10B shows an RNA blot probing for a miR-1 target co-injected (200 pg/embryo) with or without hsAGO2 mRNA (100 pg/embryo) and with or without exogenous miR-1 duplex (50 femtomol/embryo). All three biological replicates were run on the same gel. As previously reported (Giraldez et al., 2005; Cifuentes et al., 2010), slicing catalyzed by endogenous drAgo2 was detectable above background (compare lanes without hsAGO2 but with miR-1 duplex to those without miR-1 duplex), although product accumulation increased significantly more when hsAGO2 mRNA was co-injected. Differences between this experiment and that of FIG. 5, which might help explain their differing abilities to detect drAgo2-catalyzed slicing include, 1) the injection of large amounts of exogenous miRNA rather than dependence on the endogenous pool of miR-430, 2) the injection of 20-fold more target mRNA, 3) the use of a target with three sites rather than one site, and 4) the use of a miRNA and target of different sequences, which might enhance cleavage efficiency or yield a product that is more stable in embryos.

FIG. 11A is a summary of results for a domain-swap experiment, with a schematic representation of the domain and linker architecture of Ago2. Residues of the DEDH catalytic tetrad are indicated above the PIWI domain. Bars show the origin of the respective domains of each parental and chimeric construct, indicating domains from hsAGO2 and drAgo2 in blue and green, respectively. The ability of each construct to slice the miR-430 target in zebrafish embryos or to bind and cleave pre-miR-451 in zebrafish embryos is indicated (+ and −). FIG. 11B shows activities of the chimeric constructs, assaying the ability to slice a miR-430 target in zebrafish embryos, as in FIG. 5B. FIG. 11C shows activities of the chimeric constructs, assaying the ability to bind and cleave pre-miR-451 in zebrafish embryos, as in FIG. 7B.

FIG. 12A shows effects of substituting the zebrafish mutations into the human Ago2 protein, assayed as in FIG. 6C. FIG. 12B is a cladogram (left) and multiple sequence alignment (middle) (Tyner et al., 2017) comparing a short region of the Ago2 PIWI domain from all sequenced Teleostei, indicating the phylogenetic classification of each species (right) (Bernardi et al., 2012; Betancur et al., 2013). Spotted gar is also shown as an outgroup. Teleostei fall into four subgroups, the most deeply branching of which (Elopomorpha) had no available sequenced representative. Variable residues are in bold. With the exception of the Perciforme subclade (which has a D-to-E reversion), all sequenced Teleostei possess both the E-to-D and the F-to-Y substitutions (shaded in red).

FIG. 14A shows effects of a position-6 G-G mismatch on multiple-turnover slicing by hsAGO2 in vitro. Assay of one replicate (squares) in the FIG. 9A plot and were as in FIG. 8B except substrate (5 nM) was in excess over AGO2 (0.5 nM).

FIG. 14B shows effects of a position-6 G-G mismatch on multiple-turnover slicing by hsAGO2 in vitro. Shown is the extended FIG. 9A plot to include two additional time points (250 and 500 minutes).

DETAILED DESCRIPTION OF THE INVENTION

Figures 1A, 1B:
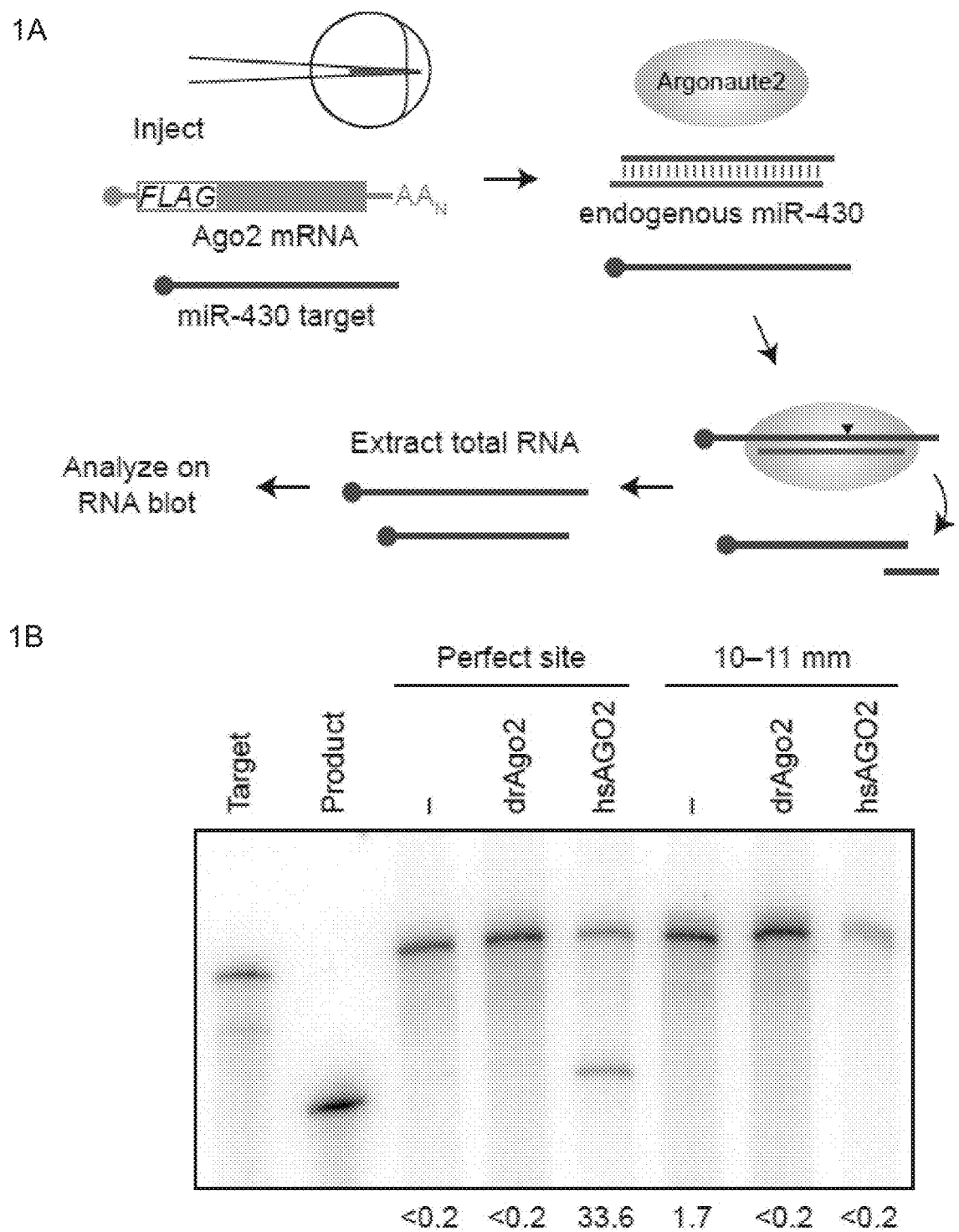
FIGS. 1A-1D depict ineffective slicing, but detectable, pre-miR-451 cleavage by drAgo2 in zebrafish embryos.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, ncbi.nlm.nih.gov/omim/ and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Definitions

For convenience, certain terms employed herein, in the specification, examples and appended claims are collected here. Unless otherwise defined, all technical and scientific terms used herein have the same meaning as commonly understood by one of ordinary skill in the art to which this invention belongs.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage or a phosphorothioate linkages between 5' and 3' carbon atoms.

The terms "RNA", "RNA molecule", and "ribonucleic acid molecule" are used herein interchangeably to refer to a polymer of ribonucleotides. The terms "DNA", "DNA molecule", and "deoxyribonucleic acid molecule" are used herein interchangeably to refer to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA" comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs).

As used herein, the term "microRNA" ("miRNA"), also referred to in the art as "small temporal RNAs" ("stRNAs"), refers to a small (10-50 nucleotide) RNA which is capable of directing or mediating RNA silencing. A "natural miRNA" refers to a microRNA that occurs naturally. An "miRNA disorder" shall refer to a disease or disorder characterized by aberrant expression or activity of a natural miRNA.

As used herein, the term "RNA interference" ("RNAi") (also referred to in the art as "gene silencing" and/or "target silencing", e.g., "target mRNA silencing") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can engineered, for example, to silence the expression of target genes.

In the context of this invention, siRNA comprises double-stranded oligonucleotides, wherein the term "oligonucleotide" refers to an oligomer or polymer of ribonucleic acid or deoxyribonucleic acid. An oligonucleotide refers to a molecule formed by the covalent linkage of two or more nucleotides. The term oligonucleotide generally includes oligonucleosides, oligonucleotide analogues, oligonucleotide mimetics and chimeric combinations of these. In the context of the present invention, a single nucleotide unit may also be referred to as a monomer or unit. In some embodiments, the terms "nucleoside", "nucleotide", "unit" and "monomer" are used interchangeably. It will be recognized that when referring to a sequence of nucleotides or monomers, what is referred to is the sequence of bases, such as, for example A, T (or U), G, or C.

The term "double-stranded RNA" or "dsRNA", as used herein, refers to a duplex structure comprising two anti-parallel and substantially complementary nucleic acid strands. In general, the majority of nucleotides of each strand are ribonucleotides, but as described in detail herein, each or both strands can also include at least one non-ribonucleotide, e.g., a deoxyribonucleotide and/or a modified nucleotide. In addition, as used in this specification, "dsRNA" may include chemical modifications to ribonucleotides, including substantial modifications at multiple nucleotides and including all types of modifications disclosed herein or known in the art.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop", "short hairpin RNA" or "shRNA". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule. For clarity, chemical caps or non-nucleotide chemical moieties conjugated to the 3' end or 5' end of an siRNA are not considered in determining whether an siRNA has an overhang or is blunt ended.

The term "antisense strand" refers to the strand of a dsRNA which includes a region that is substantially complementary to a target sequence. The region that is substantially complementary to the target sequence may be a referred to as a "guide sequence". As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule.

The term "sense strand," as used herein, refers to the strand of a dsRNA that includes a region that is substantially complementary to a region of the antisense strand.

A "target gene" is a gene whose expression is to be selectively inhibited or "silenced." This silencing can be achieved by cleaving the mRNA of the target gene or via translational repression of the target gene.

The term "engineered," as in an engineered RNA precursor, or an engineered nucleic acid molecule, indicates that the precursor or molecule is not found in nature, in that all or a portion of the nucleic acid sequence of the precursor or molecule is created or selected. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "isolated RNA" (e.g., "isolated shRNA", "isolated siRNA", "isolated siRNA-like duplex", "isolated miRNA", "isolated gene silencing agent", or "isolated RNAi agent") refers to RNA molecules which are substantially free of other cellular material, or culture medium when produced by recombinant techniques, or substantially free of chemical precursors or other chemicals when chemically synthesized.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. "Complementary" sequences, as used herein, may also include, or be formed entirely from, non-Watson-Crick base pairs and/or base pairs formed from non-natural and modified nucleotides. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of a dsRNA (e.g., a guide sequence) and a target sequence, as will be understood from the context of their use.

As used herein, a polynucleotide which is "substantially complementary to at least part of" a messenger RNA (mRNA) refers to a polynucleotide that is substantially complementary to a contiguous portion of the mRNA of interest (e.g., encoding a target gene) including a 5' UTR, an open reading frame (ORF), or a 3' UTR. For example, a polynucleotide is complementary to at least a part of a target mRNA if the sequence is substantially complementary to a non-interrupted portion of an mRNA encoding the target mRNA.

"Introducing into a cell," when referring to an oligonucleotide (e.g., a dsRNA, an siRNA, etc.), means facilitating uptake or absorption into the cell, as is understood by those skilled in the art. Absorption or uptake of an oligonucleotide can occur through unaided diffusive or active cellular processes, or by auxiliary agents or devices. The meaning of this term is not limited to cells in vitro; an oligonucleotide may also be "introduced into a cell", wherein the cell is part of a living organism. In such instance, introduction into the cell will include the delivery to the organism. For example, for in vivo delivery, an oligonucleotide can be injected into a tissue site or administered systemically. In vitro introduction into a cell includes methods known in the art such as electroporation and lipofection.

The terms "silence," "inhibit the expression of," "down-regulate the expression of," "suppress the expression of," and the like, insofar as they refer to the target gene of interest, herein refer to the at least partial suppression of the expression of the target gene of interest, as manifested by a reduction of the amount of mRNA which may be isolated or detected from a first cell or group of cells in which the target gene of interest is transcribed and which has or have been treated such that the expression of the target gene of interest is inhibited, as compared to a second cell or group of cells substantially identical to the first cell or group of cells but which has or have not been so treated (control cells).

Alternatively, the degree of inhibition may be given in terms of a reduction of a parameter that is functionally linked to target gene of interest expression, e.g. the amount of protein encoded by the target gene of interest which is produced by a cell, or the number of cells displaying a certain phenotype. In principle, target gene silencing can be determined in any cell expressing the target, either constitutively or by genomic engineering, and by any appropriate assay.

As used herein in the context of target gene expression, the terms "treat," "treatment," and the like, refer to relief from or alleviation of pathological processes which can be mediated by down regulating the target gene of interest. In the context of the present invention insofar as it relates to any of the other conditions recited herein below (other than pathological processes which can be mediated by down regulating the target gene of interest), the terms "treat," "treatment," and the like mean to relieve or alleviate at least one symptom associated with such condition, or to slow or reverse the progression of such condition.

As used herein, the phrases "therapeutically effective amount" and "prophylactically effective amount" refer to an amount that provides a therapeutic benefit in the treatment, prevention, or management of pathological processes that can be mediated by down regulating the target gene of interest or an overt symptom of pathological processes which can be mediated by down regulating the target gene of interest. The specific amount that is therapeutically effective can be readily determined by an ordinary medical practitioner, and may vary depending on factors known in the art, such as, e.g., the type of pathological processes that can be mediated by down regulating the target gene of interest, the patient's history and age, the stage of pathological processes that can be mediated by down regulating target gene of interest expression, and the administration of other anti-pathological processes that can be mediated by down regulating target gene of interest expression.

As used herein, a "pharmaceutical composition" includes a pharmacologically effective amount of an oligonucleotide and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof and are described in more detail below. The term specifically excludes cell culture medium.

As used herein, a "transformed cell" is a cell into which a vector has been introduced from which an oligonucleotide molecule may be expressed.

The methods and kits described herein are administered to any subject of interest, e.g., any mammal. The term "mammal" as used herein includes both humans and non-humans and includes but is not limited to humans, non-human primates, canines, felines, murines, bovines, equines, and porcines. In one aspect the subject is a mouse or rat or monkey or human. In another aspect the subject is a human subject. In some embodiments, the subject is a human in need of treatment for a disease correlated with expression of the targeted gene. For example, the methods can be used to treat diseases and conditions that can be modulated by down regulating target gene expression.

Oligonucleotides

In some embodiments, the siRNA comprises double-stranded oligonucleotides. The oligonucleotides can be synthesized by standard methods known in the art, e.g., by use of an automated DNA synthesizer, such as are commercially available from, for example, Biosearch, Applied Biosystems, Inc. In some aspects, compositions may be provided that include the oligonucleotide as described herein in combination with a physiologically acceptable carrier. In other aspects, compositions may be provided that include the oligonucleotides as described herein in combination with at least one isolated cell (e.g., a mammalian cell, a human cell, etc.).

In some embodiments, the oligonucleotides disclosed herein are useful for modulating the expression of nucleic acid molecules (e.g., modulating the expression of aberrantly expressed target genes) via an antisense mechanism of action. This modulation may be accomplished, for example, by providing oligonucleotides which are complementary to and/or hybridize to one or more target nucleic acid molecules, such as mRNA. In some embodiments, the oligonucleotides of the present invention are complementary to a specific region of a target nucleic acid. In some embodiments, the oligonucleotides of the present invention are capable of hybridizing to a specific region of a target nucleic acid.

As used herein, the phrase "target nucleic acid" is intended to encompass DNA and RNA (including pre-mRNA and mRNA or portions thereof) transcribed from such DNA, and also cDNA derived from such RNA. For example, in some embodiments, the phrase "target nucleic acid" is used to refer to nucleic acids encoding the target (e.g., mRNA), or in particular nucleic acids encoding mutated or aberrantly expressed targets. As used herein, the term "gene product" refers to any biochemical materials resulting from expression of a gene or nucleic acid (e.g., DNA or RNA) and include, but are not limited to mRNA, RNA and/or proteins. For example, in some embodiments, when used with respect to the target gene the phrase gene product refers to mRNA encoded by the target gene.

In some embodiments, the oligonucleotide compounds are complementary to one or more target nucleic acids (e.g., mRNA encoding a target) and interfere with the normal function of the targeted nucleic acid (e.g., by an antisense mechanism of action). In some aspects, the guide or antisense strand of the oligonucleotide has a region of complementarity that is substantially complementary to a target sequence, derived from the sequence of an mRNA formed during the expression of the target gene. The sense strand may include a region that is complementary to the antisense strand, such that the two strands hybridize and form a duplex structure when combined under suitable conditions.

In some embodiments, the functions of DNA to be interfered with may include replication and transcription. In other aspects, the functions of RNA to be interfered with may include functions such as, for example, translocation of the RNA to the site of protein translation, translation of protein from the RNA, splicing of the RNA to yield one or more mRNA species, and catalytic activity which may be engaged in or facilitated by the RNA. In some embodiments, the overall effect of interference with a target nucleic acid function is modulation of the expression of the product of such target nucleic acid.

In some embodiments, the antisense compound or antisense oligonucleotide refers to an oligonucleotide that is at least partially complementary (e.g., 100%, about 99%, 98%, 97.5%, 95%, 90%, 85%, 80%, 75%, 70%, 65%, 60%, 55%, or 50% complementary) to the region of a nucleic acid molecule, and in particular a target nucleic acid such as the mRNA encoding an aberrantly expressed protein or enzyme. In some embodiments, the antisense compound or antisense oligonucleotide is capable of hybridizing to a target nucleic acid, thereby modulating its expression. Consequently, while all antisense compounds can be said to be oligonucleotides, not all oligonucleotides are antisense compounds.

In some embodiments, the oligonucleotide consists of or comprises a contiguous nucleotide sequence of from about 8 to 50 nucleotides in length, such as for example 8 to 30 nucleotides in length, 15 to 25 nucleotides in length, 18 to 28 nucleotides in length or 19, 20, or 21 base pairs in length. In various embodiments, the compounds of the invention do not comprise RNA units or monomers, but rather, for example, comprise DNA units or monomers and/or in some instances other known units or monomers. It is preferred that the compound according to the invention is a linear molecule or is synthesized as a linear molecule. In some embodiments the oligonucleotide is a single stranded molecule, and preferably does not comprise short regions of, for example, at least 3, 4 or 5 contiguous nucleotides, which are complementary to equivalent regions within the same oligonucleotide (i.e., duplexes). In some embodiments the oligonucleotide is a double stranded molecule.

In some embodiments, an oligonucleotide can contain one or more mismatches to the target sequence (e.g., the guide sequence of the oligonucleotide may contain one or more mismatches with respect to the target sequence). In some aspects, the oligonucleotide contains no more than 1, exactly 1, no more than 2, or no more than 3 mismatches. In certain aspects, the antisense strand (e.g., guide or guide sequence or guide strand) of an siRNA contains at least one mismatch to the target sequence. In some embodiments, the position of the mismatch is measured with respect to the 5' end of the strand which serves as the guide sequence (e.g., the guide or guide strand). For example, a mismatch may be located within the seed region of an siRNA. In some aspects, the mismatch may be located within guide positions 2 to 8, or alternatively within guide positions 2 to 7 of the guide sequence. In certain embodiments, a mismatch may be located at position 6 of the guide sequence. In some embodiments, no more than 3 mismatches are located between guide positions 2 to 7 of the guide sequence. In alternative embodiments, no more than 2 mismatches, in some embodiments no more than 1 mismatch, and in some embodiments exactly 1 mismatch, is located between guide positions 2 to 7 of the guide sequence.

In some embodiments, an siRNA contains a mismatch that is designed in view of the target sequence. For example, a target sequence may be identified and a mismatch may be designed within the oligonucleotide in view of the target sequence. In some embodiments, the mismatch may be designed in view of the target sequence so as to improve the targeting and slicing of the siRNA. In some embodiments, the mismatch (e.g., the designed mismatch) may be intentionally inserted into the siRNA, thereby increasing the targeting and slicing efficiency of the siRNA.

In some aspects, the mismatch between a guide sequence of an oligonucleotide and a target sequence may be a guanine-guanine mismatch, a guanine-adenine mismatch, a guanine-uracil mismatch, an adenine-adenine mismatch, an adenine-guanine mismatch, an adenine-cytosine mismatch, a uracil-uracil mismatch, a uracil-guanine mismatch, a uracil-cytosine mismatch, a cytosine-cytosine mismatch, a cytosine-adenine mismatch, or a cytosine-uracil mismatch. In certain aspects, the mismatch between a guide sequence of an oligonucleotide and a target sequence is selected from the group consisting of a guanine-guanine mismatch, a guanine-adenine mismatch, and a guanine-uracil mismatch. In some aspects, the mismatch between a guide sequence of an oligonucleotide and a target sequence is selected from the group consisting of an adenine-adenine mismatch, an adenine-guanine mismatch, and an adenine-cytosine mismatch. n other aspects, the mismatch between a guide sequence of an oligonucleotide and a target sequence is selected from the group consisting of a uracil-uracil mismatch, a uracil-guanine mismatch, and a uracil-cytosine mismatch. In some aspects, the mismatch between a guide sequence of an oligonucleotide and a target sequence is selected from the group consisting of a cytosine-cytosine mismatch, a cytosine-adenine mismatch, and a cytosine-uracil mismatch. For example, the mismatch between a guide sequence of an oligonucleotide and a target sequence may be a guanine-guanine mismatch. In certain embodiments, the mismatch between a guide sequence of an oligonucleotide and a target sequence is a guanine-guanine mismatch and occurs at position 6 of the guide sequence.

It was surprisingly determined that a mismatch located within positions 2 to 7 of the guide sequence of an oligonucleotide provides improved efficacy of siRNAs and shRNAs. In fact, it was identified that a mismatch as described herein differs from previously characterized mismatches in that it can confer a net benefit in target binding and slicing. For example, an oligonucleotide (e.g., an siRNA) having a guide sequence with at least one mismatch with respect to a target sequence may exhibit at least a 2.5 fold higher overall rate for target binding and slicing, as compared to an oligonucleotide having a guide sequence without a mismatch with respect to the target sequence.

Oligonucleotides discussed include otherwise unmodified RNA and DNA as well as RNA and DNA that have been modified. Examples of modified RNA and DNA include modifications to improve efficacy and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. Modified RNA as used herein refers to a molecule in which one or more of the components of the nucleic acid, namely sugars, bases, and phosphate moieties, are different from that which occur in nature, preferably different from that which occurs in the human body.

In some aspects, an oligonucleotide may be an activated oligonucleotide. An "activated oligonucleotide" refers to an oligonucleotide (e.g., siRNA) of the invention that is covalently linked (i.e., functionalized) to at least one functional moiety that permits covalent linkage of the oligonucleotide to one or more conjugated moieties (i.e., moieties that are not themselves nucleic acids or monomers) to form the conjugates herein described. Typically, a functional moiety will comprise a chemical group that is capable of covalently bonding to the oligonucleotide via, for example, a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected (e.g., an $NH_2$ group). In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl. In some embodiments, the functional moiety is self-cleaving. In other embodiments, the functional moiety is biodegradable (see e.g., U.S. Pat. No. 7,087,229).

In some embodiments, oligonucleotides (e.g., siRNAs) of the invention are functionalized at the 5' end in order to allow covalent attachment of the conjugated moiety to the 5' end of the oligonucleotide. In other embodiments, oligonucleotides of the invention can be functionalized at the 3' end. In yet other embodiments, oligonucleotides of the invention can be functionalized at more than one position independently selected from the 5' end and the 3' end.

In some embodiments, activated oligonucleotides of the invention are synthesized by incorporating during the synthesis one or more monomers that is covalently attached to a functional moiety. In other embodiments, activated oligonucleotides of the invention are synthesized with monomers that have not been functionalized, and the oligonucleotide is functionalized upon completion of synthesis. In some embodiments, the oligonucleotides are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligonucleotide via an ester group ($—O—C(O)—(CH_2)_wNH$).

In other embodiments, the oligonucleotides are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligonucleotide via an ester group ($—O—C(O)—(CH_2)_wSH$)

In some embodiments, sulfhydryl-activated oligonucleotides are conjugated with polymer moieties such as polyethylene glycol or peptides (via formation of a disulfide bond).

Activated oligonucleotides containing hindered esters as described above can be synthesized by any method known in the art, and in particular by methods disclosed in International Application WO 2008/034122 and the examples therein In still other embodiments, the oligonucleotides of the invention are functionalized by introducing sulfhydryl, amino or hydroxyl groups into the oligonucleotide by means of a functionalizing reagent substantially as described in U.S. Pat. Nos. 4,962,029 and 4,914,210 (i.e., a substantially linear reagent having a phosphoramidite at one end linked through a hydrophilic spacer chain to the opposing end which comprises a protected or unprotected sulfhydryl, amino or hydroxyl group). Such reagents primarily react with hydroxyl groups of the oligonucleotide. In some embodiments, such activated oligonucleotides have a functionalizing reagent coupled to a 5'-hydroxyl group of the oligonucleotide. In other embodiments, the activated oligonucleotides have a functionalizing reagent coupled to a 3'-hydroxyl group. In yet further embodiments, the oligonucleotide of the invention is functionalized with more than one of the functionalizing reagents as described in U.S. Pat. Nos. 4,962,029 and 4,914,210. Methods of synthesizing such functionalizing reagents and incorporating them into monomers or oligonucleotides are described in U.S. Pat. Nos. 4,962,029 and 4,914,210.

In some embodiments, the 5'-terminus of a solid-phase bound oligonucleotide is functionalized with a dienyl phosphoramidite derivative, followed by conjugation of the deprotected oligonucleotide with, e.g., an amino acid or peptide via a Diels-Alder cycloaddition reaction.

In various embodiments, the incorporation of monomers containing 2'-sugar substitutions, such as a 2'-carbamate substituted sugar or a 2'-(O-pentyl-N-phthalimido)-deoxyribose sugar into the oligonucleotide facilitates covalent attachment of conjugated moieties to the sugars of the oligonucleotide. In other embodiments, an oligonucleotide with an amino-containing linker at the 2'-position of one or more monomers is prepared using a reagent such as, for example, 5'-dimethoxytrityl-2'-O-(e-phthalimidylaminopentyl)-T-deoxyadenosine-3'-N,N-diisopropyl-cyanoethoxy phosphoramidite. (See, e.g., Manoharan, et al., Tetrahedron Letters, (1991) 34:7171.)

In still further embodiments, the oligonucleotides of the invention may have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligonucleotide synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino- Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

In some embodiments, the oligonucleotide is chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated by reference. Specific examples of oligonucleotide compounds useful in this invention include oligonucleotides containing modified backbones or no natural internucleoside linkages. As defined in this specification, oligonucleotides having modified backbones include those that retain a phosphorus atom in the backbone and those that do not have a phosphorus atom in the backbone. In some aspects, modified oligonucleotides that do not have a phosphorus atom in their internucleoside backbone can also be considered to be oligonucleosides.

In some embodiments, modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

In some aspects, modified oligonucleotide backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other certain oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In some aspects in PNA compounds, the sugar backbone of an oligonucleotide is replaced with an amide containing backbone, for example, an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teachings of PNA compounds can be found in Nielsen et al., Science, 1991, 254, 1497-1500.

In other embodiments of the invention, oligonucleotides have phosphorothioate backbones and oligonucleosides with heteroatom backbones, and in particular—$CH_2$—NH—$CH_2$—, —$CH_2$—$N(CH_3)$—O—$CH_2$— [known as a methylene (methylimino) or MMI backbone], —$CH_2$—O—N$(CH_3)$—$CH_2$—, —$CH_2$—$N(CH_3)$—$N(CH_3)$—$CH_2$—and —$N(CH_3)$—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. Other aspects include siRNAs having morpholino backbone structures of the above-referenced U.S. Pat. No. 5,034,506.

Modified oligonucleotides may also contain one or more substituted sugar moieties. In some embodiments, oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other examples include, $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other aspects, siRNAs comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In some embodiments, a modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxy-alkoxy group. In other aspects, a modification includes 2'-dimethylaminooxyethoxy, i.e., a $O(CH_2)_2ON(CH_3)_2$ group, also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$.

In some embodiments, modifications include 2'-methoxy (2'-$OCH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Additional nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, those disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993.

In other embodiments, modifications of the oligonucleotide involve chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-5-tritylthiol (Manoharan et al., Ann. N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937). In some aspects, various conjugates will assist in targeting cells. Such conjugates include, but are not limited to, mannose and folate conjugates.

In some embodiments, it is not necessary for all positions in a given compound to be uniformly modified. In certain aspects, more than one of the aforementioned modifications may be incorporated in a single compound or even at a single nucleoside within an oligonucleotide. In some embodiments, oligonucleotide compounds are chimeric compounds. "Chimeric" oligonucleotide compounds or "chimeras," in the context of this invention, are oligonucleotide compounds, particularly oligonucleotides, which contain two or more chemically distinct regions, each made up of at least one monomer unit, i.e., a nucleotide in the case of an oligonucleotide compound. In some aspects, these oligonucleotides typically contain at least one region wherein the oligonucleotide is modified so as to confer upon the oligonucleotide increased resistance to nuclease degradation, increased cellular uptake, and/or increased binding affinity for the target nucleic acid. In certain aspects, an additional region of the oligonucleotide may serve as a substrate for enzymes capable of cleaving RNA:DNA or RNA:RNA hybrids. For example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Cleavage of the RNA target can be routinely detected by gel electrophoresis and, if necessary, associated nucleic acid hybridization techniques known in the art.

In certain embodiments, the oligonucleotide may be modified by a non-ligand group. In some aspects, a number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Lett., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). In some aspects, typical conjugation protocols involve the synthesis of oligonucleotides bearing an aminolinker at one or more positions of the sequence. The amino group is then reacted with the molecule being conjugated using appropriate coupling or activating reagents. In some aspects, the conjugation reaction may be performed either with the oligonucleotide still bound to the solid support or following cleavage of the oligonucleotide in solution phase. Purification of the oligonucleotide conjugate by HPLC may provide the pure conjugate.

Targets

In some embodiments, the oligonucleotides (e.g., the siRNAs) described herein can be used to downregulate or silence the translation (i.e., expression) of a gene of interest. Genes of interest include, but are not limited to, genes associated with viral infection and survival, genes associated with metabolic diseases and disorders (e.g., liver diseases and disorders), genes associated with tumorigenesis and cell transformation, angiogenic genes, immunomodulator genes, such as those associated with inflammatory and autoimmune responses, ligand receptor genes, and genes associated with neurodegenerative disorders.

In certain embodiments, the oligonucleotides described herein are capable of modulating, or in some embodiments down-regulating (e.g. reducing or eliminating) the expression of a target (e.g., down-regulating aberrantly expressed target at the mRNA level). In this regards, the oligonucleotides of the invention can affect the inhibition of the target, typically in a mammalian cell such as a human cell (e.g., an A549 cell, a HeLa cell, a hepatocyte cell, or in a chondrocyte). In some embodiments, the oligonucleotides of the invention hybridize to the target nucleic acid (e.g., mutated or aberrantly expressed target mRNA) and affect inhibition or reduction of expression of at least 10% or 20% compared to the normal expression level (e.g., such as the expression level in the absence of the oligonucleotide or conjugate). For example, the oligonucleotides disclosed herein may affect at least about a 30%, 40%, 50%, 60%, 70%, 80%, 90%, 95%, 97.5%, 98%, 99% or 100% reduction or inhibition of the expression of the target compared to the normal expression level of the target seen an individual carrying a target mutant allele. In some embodiments, such modulation is evident upon exposing a targeted cell or tissue to a concentration of about 0.01 nM-25 nM (e.g., a concentration of about 0.8 nM-20 nM) of the compound of the invention. In the same or a different embodiment, the inhibition of expression of the target nucleic acid (e.g., mRNA encoding mutated target) is less than 100% (e.g., such as less than about 98% inhibition, less than about 95% inhibition, less than about 90% inhibition, less than about 80% inhibition or less than about 70% inhibition). In some embodiments, the oligonucleotides disclosed herein are capable of modulating expression of the target at the mRNA level (e.g., by targeting and hybridizing to mRNA encoding mutated or aberrantly expressed target). Modulation of expression (e.g., at the mRNA level) can be determined by measuring protein levels or concentrations (e.g., by SDS-PAGE followed by Western blotting using suitable antibodies raised against the target protein). Alternatively, modulation of expression (e.g., at the mRNA level) can be determined by measuring levels or concentrations of mRNA, (e.g., by Northern blotting or quantitative RT-PCR). When measuring expression via the evaluation of mRNA levels or concentrations, the degree of down-regulation when using an appropriate dosage or concentration of an oligonucleotide (e.g., about 0.01 nM-25 nM, or about 0.8 nM-20 nM), can be greater than about 10%, from about 10-20%, greater than about 20%, greater than about 25%, or greater than about 30% relative to the normal levels or concentrations observed in the absence of the oligonucleotide, conjugate or composition of the invention.

In the context of the present invention, the terms "modulating" or "modulation" can mean one or more of an increase (e.g., stimulation or upregulation) in the expression of a gene or gene product (e.g., target mRNA), a decrease (e.g., downregulation or inhibition) in the expression of a gene or gene product (e.g., target mRNA), and a change in the relative expression between two or more gene products (e.g., a reduction in the expression of mutant target relative to the expression of wild-type target). In some contexts described herein, downregulation and inhibition are the preferred forms of modulation, in particular as it relates to modulating the expression of mutated target. In some contexts described herein, the term "expression" means the process by which information from a gene or nucleic acid (e.g., DNA) is used in the synthesis of gene products (e.g., mRNA, RNA and/or proteins) and includes, but is not limited to, one or more of the steps of replication, transcription and translation. The steps of expression which may be modulated by the oligonucleotides of the present invention may include, for example, transcription, splicing, translation and post-translational modification of a protein.

As it relates to targeting, modulation and expression, the term "target" broadly can refer to any target gene or its gene product (e.g., pre-mRNA, mature mRNA, cDNA, or protein) and can include both mutated and wild-type forms, isoforms and variants thereof. The term "wild-type" as it describes target, refers to the most frequently observed target allele, nucleotide sequence, amino acid sequence, or phenotype in a subject or population. The term "mutated" as it describes target refers to an altered allele, nucleotide sequence, amino acid sequence, or phenotype in a subject or population, for example, transition and transversion point mutations that result in the replacement of a single base nucleotide with another nucleotide of the genetic material (e.g., DNA or RNA).

In some embodiments, the oligonucleotides of the present invention are capable of targeting specific nucleic acids. Targeting in the context of the antisense oligonucleotides described herein to a particular nucleic acid can be a multi-step process. The process usually begins with the identification of a nucleic acid sequence whose function is to be modulated. This may be, for example, a nucleic acid (e.g., mRNA) whose expression is associated with a particular disorder or disease state. In some embodiments, the target nucleic acid (e.g., mRNA) encodes a target. For example, the target nucleic acid may comprise a region or fragment of the nucleic acid gene encoding the a mutation, and the oligonucleotide targeting such region complement to and/or hybridize to the nucleic acids encoding the target mRNA. Alternatively, in some embodiments the target nucleic acid encodes a particular region of the target gene (or the corresponding mRNA gene product thereof) which encodes the mutation. The targeting process also can include a determination of a site or sites within the target gene for the antisense interaction to occur such that one or more desired effects will result. The one or more desired effects can include, for example, modulation of expression of a gene product (e.g., wild-type and/or mutant mRNA or protein), selective binding (e.g., increased binding affinity) for the target site relative to other sites on the same gene or mRNA or on other genes or mRNAs, sufficient or enhanced delivery to the target, and minimal or no unwanted side effects. In some embodiments, a preferred targeted nucleic acid or mRNA site encodes the target mutation and/or the region surrounding or adjacent to such mutation.

The oligonucleotides described herein may be delivered to one or more of an animal, a mammal, a human, or a cell. Targeted cell types may, in some embodiments, include hepatocyte cells, chondrocyte cells, HeLa cells or A549 cells. In certain embodiments, the oligonucleotide concentration used (e.g., in A549 cells) may be about 0.25 nM, 0.5 nM, 1 nM, 5 nM, 40 nM, 100 nM, 200 nM, 250 nM or more. The oligonucleotide concentration used may, in some embodiments be 25 nM (e.g., in chondrocyte cells). The oligonucleotide concentration used may, in some embodiments be 1 nM (e.g., in chondrocyte cells). In the absence of a transfection reagent (e.g., using gymnotic delivery) an oligonucleotide concentration between about 1 μM-25 μM (e.g., such as about 504) may be used to downregulate the target gene.

In certain embodiments, the oligonucleotides disclosed herein may be periodically administered to a subject (e.g., administered intravenously or subcutaneously to a human on a daily, weekly, monthly, quarterly, semi-annually or annual basis) at a dose of about 0.1 to about 20 mg/kg (e.g., administered in daily or weekly doses of at least about 01 mg/kg, 0.25 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 6.0 mg/kg, 7.5 mg/kg, 8.0 mg/kg, 10 mg/kg, 12.5 mg/kg, 15 mg/kg or 20 mg/kg). It should be noted that in some embodiments the determination of the appropriate concentration of oligonucleotide used to treat the cell may be performed in an in vitro cell assay using a transfection reagent (e.g., LIPOFECTIN).

In some embodiments, the oligonucleotides described herein are potent inhibitors of a target (i.e., are capable of modulating the expression of the target in a cell or tissue upon exposing such cell or tissue to a relatively low concentration of the oligonucleotide). In some embodiments, the oligonucleotides are capable of reducing or otherwise inhibiting the expression of a target at relatively low concentrations of such oligonucleotide. For example, in some embodiments an oligonucleotide may inhibit expression of a target by a cell at a relatively low concentration (e.g., an $IC_{50}$ of less than about 5 nM as determined by a transfection assay, or an $IC_{50}$ of less than about 4 nM, such as less than 2 nM). As used herein, the term "$IC_{50}$" refers to the concentration of an oligonucleotide that is sufficient to inhibit an objective parameter (e.g., target protein expression) by about fifty percent. In certain embodiments, the antisense oligonucleotides disclosed herein are characterized as selectively inhibiting the expression of mutant target protein relative to the expression of wild-type target protein. Accordingly, an oligonucleotide may be characterized as inhibiting the expression of mutant target protein at a lower concentration (e.g., about two-fold lower) relative to the concentration required to inhibit expression of a wild-type target protein. For example, the antisense oligonucleotides may demonstrate at least a two-fold difference in the $IC_{50}$ for the mutant and wild-type target proteins (e.g., at least about a 2.5-, 3-, 4-, 5-, 6-, 7-, 8-, 9- or 10-fold difference in the $IC_{50}$ required to inhibit expression of the target mutant protein relative to the normal or wild-type protein in a mammal).

The invention therefore provides methods of modulating (e.g., downregulating or inhibiting) the expression of a target protein and/or target mRNA. In some embodiments, the target protein and/or target mRNA is an aberrantly expressed or mutated target protein and/or target mRNA. Such methods comprise administering the oligonucleotide or conjugate according to the invention to a cell (or otherwise contacting such cell with such oligonucleotide or conjugate) to downregulate or inhibit the expression of the target protein and/or mRNA in said cell. In some embodiments, the cell can be an in vitro or in vivo mammalian cell, such as a human cell. For example, an oligonucleotide of the present invention that targets a mutated target gene and specifically hybridizes to the gene product thereof (e.g., mutated target mRNA) may modulate the expression of mutated target. The oligonucleotides of the present invention may modulate the expression of wild-type and/or mutated target alleles in patients. The administration to the patient (e.g., human or mammalian), subject (e.g., human or mammalian), and/or cell (e.g., human or mammalian) may occur in vivo, ex vivo, or in vitro. For example, in some embodiments, the oligonucleotide in a pharmaceutically acceptable formulation and/or in a pharmaceutically acceptable carrier or delivery vehicle may be administered directly into the patient's or subject's body, by methods described herein. Alternatively, in some embodiments, the oligonucleotide may be administered to cells after they are removed and before they are returned to the patient's or subject's body. In some embodiments, the cells may be maintained under culture conditions after they are removed and before they are returned to the patient's or subject's body.

The phrase "target nucleic acid", as used herein refers to the nucleic acids (e.g., mRNA) encoding the target (e.g., mammalian or non-mammalian target), and in particular refers to the nucleic acids (e.g., mRNA) encoding mutated or aberrantly expressed target. Suitable target nucleic acids include nucleic acids encoding the target or naturally occurring variants thereof, and RNA nucleic acids derived therefrom, preferably mRNA, such as pre-mRNA, although preferably mature mRNA. In some embodiments (e.g., when used in a research or diagnostic context) the "target nucleic acid" may be a cDNA or a synthetic oligonucleotide derived from the above DNA or RNA nucleic acid targets. The oligonucleotides according to the invention are capable of hybridizing to the target nucleic acid or to the gene product of such target nucleic acid. It will be recognized that in some embodiments the target nucleic acid sequence is a cDNA sequences and as such, corresponds to the mature mRNA target sequence, although uracil may be replaced with thymidine in the cDNA sequences.

The term "naturally occurring variant thereof" refers to variants of the target polypeptide or nucleic acid sequence which exist naturally within the defined taxonomic group, such as mammalian, such as mouse, monkey, and preferably human. In alternative embodiments, the defined taxonomic group is non-mammalian. Naturally occurring variants may also include variants derived from alternative splicing of the target mRNA. When referenced to a specific polypeptide sequence the term also includes naturally occurring forms of the protein which may therefore be processed, for example, by co- or post-translational modifications (e.g., signal peptide cleavage, proteolytic cleavage, glycosylation, etc.)

In some embodiments, a target (e.g., a target gene) encodes transmembrane protease, serine 6 (Tmprss6). In some embodiments, inhibiting expression of Tmprss6 is useful for the treatment of β-thalassemia and iron overload disorders. In some embodiments, a target gene encodes a complement factor such as C5. In some embodiments, inhibiting expression of a complement factor, e.g., C5, is useful for treatment of complement-mediated diseases such as paroxysmal nocturnal hemoglobinuria (PNH), atypical hemolytic-uremic syndrome (aHUS), or neuromyelitis optica. In some embodiments a target gene encodes angiopoietin-like 3 (ANGPTL3). In some embodiments inhibiting expression of ANGPTL3 is useful for the treatment of genetic forms of mixed hyperlipidemia and severe hypertriglyceridemia. In some embodiments a target gene encodes apolipoprotein C3 (apoC3). In some embodiments inhibiting expression of apoC3 is useful for the treatment of hypertriglyceridemia. In some embodiments a target gene encodes glycolate oxidase. In some embodiments, inhibiting expression of glycolate oxidase is useful for treatment of primary hyperoxaluria type 1. In some embodiments, any of the oligonucleotides described herein may be administered in nanoparticles, e.g., lipid nanoparticles In some embodiments, target genes of interest include, but are not limited to, genes associated with viral infection and survival, genes associated with metabolic diseases and disorders (e.g., liver diseases and disorders), genes associated with tumorigenesis and cell transformation, angiogenic genes, immunomodulator genes, such as those associated with inflammatory and autoimmune responses, ligand receptor genes, and genes associated with neurodegenerative disorders.

In some embodiments, genes associated with viral infection and survival include those expressed by a virus in order to bind, enter and replicate in a cell. In some aspects, viral sequences are associated with chronic viral diseases, such as sequences of Hepatitis viruses, Human Immunodeficiency Virus (HIV), Herpes viruses, and Human Papilloma Viruses (HPV). In some aspects, hepatitis viral nucleic acid sequences that can be silenced include, but are not limited to, nucleic acid sequences involved in transcription and translation (e.g., En1, En2, X, P) and nucleic acid sequences encoding structural proteins (e.g., core proteins including C and C-related proteins; capsid and envelope proteins including S, M, and/or L proteins, or fragments thereof). In some aspects, Hepatits C nucleic acid sequences that can be silenced include, but are not limited to, serine proteases (e.g., NS3/NS4), helicases (e.g. NS3), polymerases (e.g., NS5B), and envelope proteins (e.g., E1, E2, and p7). In some embodiments, silencing of sequences that encode genes associated with viral infection and survival can be used in combination with the administration of conventional agents used to treat the viral condition.

In some embodiments, genes are associated with metabolic diseases and disorders (e.g., disorders in which the liver is the target and liver diseases and disorders). One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. In certain aspects, silencing of sequences that encode genes associated with metabolic diseases and disorders can conveniently be used in combination with the administration of conventional agents used to treat the disease or disorder.

In some embodiments, gene sequences associated with tumorigenesis and cell transformation include: translocation sequences, such as MLL fusion genes, BCR-ABL, TEL-AML1, EWS-FLI1, TLS-FUS, PAX3-FKHR, BCL-2, AML1-ETO and AML1-MTG8; overexpressed sequences, such as multidrug resistance genes, cyclins, beta-Catenin, telomerase genes, c-MYC, N-MYC, BCL-2, ERBB1 and ERBB2; and mutated sequences such as RAS. In certain aspects, silencing of sequences that encode DNA repair enzymes find use in combination with the administration of chemotherapeutic agents. In some aspects, genes encoding proteins associated with tumor migration are also target sequences of interest, for example, integrins, selectins and metalloproteinases. The foregoing examples are not exclusive. Any whole or partial gene sequence that facilitates or promotes tumorigenesis or cell transformation, tumor growth or tumor migration can be included as a template sequence In some aspects, angiogenic genes are able to promote the formation of new vessels, for example, Vascular Endothelial Growth Factor (VEGF) or VEGFr. siRNA sequences that target VEGFr.

In some aspects, immunomodulator genes are genes that modulate one or more immune responses. Examples of immunomodulator genes include cytokines such as growth factors (e.g., TGF-α, TGF-β, EGF, FGF, IGF, NGF, PDGF, CGF, GM-CSF, SCF, etc.), interleukins (e.g., IL-2, IL-4, IL-12, IL-15, IL-18, IL-20, etc.), interferons (e.g., IFN-α, IFN-β, IFN-γ, etc.) and TNF. In some aspects, Fas and Fas Ligand genes are also immunomodulator target sequences of interest. In certain aspects, genes encoding secondary signaling molecules in hematopoietic and lymphoid cells are also considered target genes, for example, Tec family kinases, such as Bruton's tyrosine kinase (Btk).

In some embodiments, cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g., inhibit, activate, etc.) the physiological pathway that the receptor is involved in (e.g., glucose level modulation, blood cell development, mitogenesis, etc.). Examples of cell receptor ligands include cytokines, growth factors, interleukins, interferons, erythropoietin (EPO), insulin, glucagon, G-protein coupled receptor ligands, etc.). In some aspects, templates coding for an expansion of trinucleotide repeats (e.g., CAG repeats), find use in silencing pathogenic sequences in neurodegenerative disorders caused by the expansion of trinucleotide repeats, such as spinobulbular muscular atrophy and Huntington's Disease.

In some embodiments, the invention provides a method for inhibiting the expression of a target gene in a subject. For example, in certain instances, expression of a target gene is suppressed by at least about 5%, 10%, 15%, 20%, 25%, 30%, 35%, 40%, 45%, or 50% by administration of the oligonucleotide of the invention. In some embodiment, a target gene is suppressed by at least about 60%, 70%, or 80% by administration of the oligonucleotide of the invention. In some embodiments, a target gene is suppressed by at least about 85%, 90%, or 95% by administration of the oligonucleotide of the invention.

Pharmaceutical Compositions

The oligonucleotides (e.g., siRNAs) of the invention may be used in pharmaceutical formulations and compositions. Suitably, such compositions comprise a pharmaceutically acceptable solvent, such as water or saline, diluent, carrier, salt or adjuvant. PCT/DK2006/000512 provides suitable and preferred pharmaceutically acceptable diluent, carrier and adjuvants. Suitable dosages, formulations, administration routes, compositions, dosage forms, combinations with other therapeutic agents, pro-drug formulations are also provided in PCT/DK2006/000512.

The present invention also includes pharmaceutical compositions and formulations which include the oligonucleotides (e.g., siRNAs) of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial (e.g., intrathecal or intraventricular, administration).

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999.

Compositions and formulations for oral administration include powders or granules, microparticulates, nanoparticulates, suspensions or solutions in water, saline or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate, Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), U.S. Ser. No. 09/108,673 (filed Jul. 1, 1998), U.S. Ser. No. 09/256,515 (filed Feb. 23, 1999), U.S. Ser. No. 09/082,624 (filed May 21, 1998) and U.S. Ser. No. 09/315,298 (filed May 20, 1999).

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances, which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

In another aspect, methods are provided to target a compound of the invention to a specific tissue, organ or location in the body. Exemplary targets include liver, lung, kidney, heart, and atherosclerotic plaques within a blood vessel. Methods of targeting compounds are well known in the art. In one embodiment, the compound is targeted by direct or local administration. For example, when targeting a blood vessel, the compound is administered directly to the relevant portion of the vessel from inside the lumen of the vessel, e.g., single balloon or double balloon catheter, or through the adventitia with material aiding slow release of the compound, e.g., a pluronic gel system as described by Simons et al., Nature (1992) 359: 67-70. Other slow release techniques for local delivery of the compound to a vessel include coating a stent with the compound. Methods of delivery of the oligonucleotides to a blood vessel are disclosed in U.S. Pat. No. 6,159,946.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in International Applications WO 1993/24510 and WO 1994/26764 and in U.S. Pat. No. 5,770,713.

The term "pharmaceutically acceptable salts" refers to physiologically and pharmaceutically acceptable salts of the compounds of the invention (i.e., salts that retain the desired biological activity of the parent compound and do not impart undesired toxicological effects thereto). For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Applications

The oligonucleotides (e.g., siRNAs) of the invention may be utilized as research reagents for, for example, diagnostics, therapeutics and prophylaxis. In research, such oligonucleotides may be used to specifically inhibit the synthesis of a target gene (typically by degrading or inhibiting the mRNA and thereby prevent protein formation) in cells and experimental animals thereby facilitating functional analysis of the target or an appraisal of its usefulness as a target for therapeutic intervention.

In diagnostics the oligonucleotides may be used to detect and quantitate target gene expression in cell and tissues by northern blotting, in-situ hybridisation or similar techniques.

For therapeutics, an animal or a human, suspected of having a disease or disorder, which can be treated by modulating the expression of the target gene is treated by administering oligonucleotides in accordance with this invention. Further provided are methods of treating a mammal, such as treating a human, suspected of having or being prone to a disease or condition, associated with expression of the target gene by administering a therapeutically or prophylactically effective amount of one or more of the oligonucleotides or compositions of the invention. The oligonucleotide, a conjugate or a pharmaceutical composition according to the invention is typically administered in an effective amount.

The invention also provides for the use of the compound or conjugate of the invention as described for the manufacture of a medicament for the treatment of a disorder as referred to herein, or for a method of the treatment of a disorder as referred to herein.

The invention also provides for a method for treating a disorder as referred to herein said method comprising administering a compound according to the invention as herein described, and/or a conjugate according to the invention, and/or a pharmaceutical composition according to the invention to a patient in need thereof.

Medical Indications

The oligonucleotides (e.g., siRNAs) and other compositions according to the invention can be used for the treatment of conditions associated with over expression or expression of mutated version of the target gene. The invention further provides use of a compound of the invention in the manufacture of a medicament for the treatment of a disease, disorder or condition as referred to herein.

Generally stated, one aspect of the invention is directed to methods of treating a mammal suffering from or susceptible to conditions associated with abnormal levels or aberrant expression of the target gene, comprising administering to the mammal a therapeutically effective amount of an oligonucleotide targeted to the gene product of a mutated or naturally occurring variant of the target gene (e.g., mRNA encoding a mutated target gene). The disease or disorder, as referred to herein, may, in some embodiments be associated with a mutation in the target gene or a gene whose protein product is associated with or interacts with the target. Therefore, in some embodiments, the target mRNA is a mutated form of the target mRNA.

One aspect of the invention is directed to the use of an oligonucleotide or a conjugate for the preparation of a medicament for the treatment of a disease, disorder or condition as referred to herein.

The methods of the invention are preferably employed for treatment or prophylaxis against diseases caused by abnormal levels of a target gene. Alternatively stated, in some embodiments, the invention is furthermore directed to a method for treating abnormal levels of a target gene, said method comprising administering an oligonucleotide of the invention, or a conjugate of the invention or a pharmaceutical composition of the invention to a patient in need thereof.

The invention also relates to an oligonucleotide, a composition or a conjugate as defined herein for use as a medicament.

The invention further relates to use of a compound, composition, or a conjugate as defined herein for the manufacture of a medicament for the treatment of abnormal levels of a target gene or expression of mutant forms of a target gene (such as allelic variants, such as those associated with one of the diseases referred to herein).

Moreover, the invention relates to a method of treating a subject suffering from a disease or condition such as those referred to herein.

A patient who is in need of treatment is a patient suffering from or likely to suffer from the disease or disorder.

In some embodiments, the term "treatment" as used herein refers to both treatment of an existing disease (e.g. a disease or disorder as herein referred to), or prevention of a disease, (i.e., prophylaxis). It will therefore be recognized that treatment as referred to herein may, in some embodiments, be prophylactic.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of a target gene is treated by administering oligonucleotides in accordance with this invention. The oligonucleotides of the invention can be utilized in pharmaceutical compositions by adding an effective amount of an oligonucleotide to a suitable pharmaceutically acceptable diluent or carrier.

The antisense compounds of the invention are useful for research and diagnostics, because these compounds hybridize to nucleic acids encoding a target gene, enabling sandwich and other assays to easily be constructed to exploit this fact. Hybridization of the oligonucleotides of the invention with a nucleic acid encoding the target gene can be detected by means known in the art. Such means may include conjugation of an enzyme to the oligonucleotide, radiolabelling of the oligonucleotide or any other suitable detection means. Kits using such detection means for detecting the level of target protein or mRNA in a sample may also be prepared.

Teleost Cells

In some embodiments, the invention described herein relates to a teleost cell (e.g., a zebrafish cell). In some embodiments, a genetically modified teleost (e.g., a zebrafish) includes at least one teleost cell as described herein. In some embodiments, a genetically modified teleost or teleost cell may be generated using any genome editing system known in the art, such as CRISPR/Cas or TALENS. A teleost cell may comprise a nucleic acid that encodes an Argonaute polypeptide that has increased target slicing ability as compared to the Argonaute2 (Ago2) polypeptide that is native to the teleost cell or organism.

In some aspects, the present disclosure identifies that the Ago2 polypeptides that are naturally expressed by teleosts contain an aspartate (D) at a position that is occupied by an active-site glutamate (E) in non-teleost species (e.g., human, mouse, chicken) and a tyrosine (Y) at a position that is occupied by a phenylalanine (F) in non-teleost species (e.g., human, mouse, chicken). For example, as depicted in FIG. 2D, the partial sequence of zebrafish Ago2 (SEQ ID NO: 1) contains an aspartate at position 16 and a tyrosine at position 45, as does the homologous sequence in other teleost species listed (Medaka, Tetraodon, Fugu): PSRYCATVRVQQHRQ-DIIQDLATMVRELLIQFYKSTRFKPTRIIYYRD-GISEGQFN QVL (SEQ ID NO: 1). In contrast, the homologous Ago2 polypeptide sequences present in the other organisms listed in FIG. 2D contain a glutamate at position 16 and a phenylalanine at position 45. Table 1 provides the Refseq, Genbank, or Ensembl accession numbers (and, where applicable, version numbers) of the nucleic acid sequences that encode the Ago2 polypeptide native to each listed organism.

TABLE 1

| | |
|---|---|
| Human | REFSEQ accession NM_012154.3 |
| Mouse | REFSEQ accession NM_153178.4 |
| Chicken | Ensembl ENSGALT00000026092 |
| Frog | REFSEQ accession NM_001093519.1 |
| Coelacanth | Ensembl ENSLACT00000001439 |
| Zebrafish | REFSEQ accession NM_001302222.1 |
| Medaka | Ensembl ENSORLT00000005806 |
| Tetraodon | Genbank accession CAAE01015029.1 |
| Fugu | REFSEQ accession XM_003969270.2 |
| Gar | REFSEQ: accession XM_015357469.1 |
| Lamprey | Ensembl: ENSPMAT00000009610 |

In some aspects, the sequence of zebrafish Ago2 polypeptide (isoform 1) has RefSeq accession/version number protein accession number NP_001289151.1 and is as follows:

(SEQ ID NO: 2)
MYPIGAAGATELFQGRPSSGSDVSAPASPPAPQEYVEKPPQRPDFGTMGR

TIKLQANFFEMEIPKLEVYHYEIDIKPEKCPRGVNREIVEHMVQHFKTQI

FGDRKPVYDGRKNLYTAMPLPIGRDKVELEVTIPGEGKDRSFKVAIKWMS

CVSLQALHEALSGRLPNIPFETIQALDVVMRHLPSMRYTPVGRSFFTPSE

GCSNPLGGGREVWFGFHQSVRPSLWKMMLNIDVSATAFYKAQPVIEFMCE

VLDEKSIEEQQKPLTDSQRVKFTKEIKGLKVEITHCGQMKRKYRVCNVTR

RPASHQTFPLQQENGQTIECTVAQYFKDKYKLVLRYPHLPCLQVGQEQKH

TYLPLEVCNIVAGQRCIKKLTDNQTSTMIRATARSAPDRQDEISKLMRSA

NFNTDPYVREFGVMVRDDMTEVNGRVLQAPSILYGGRNKAIATPVQGVWD

MRNKQFHTGIEIKVWAIACFAPQRQCTELLLKAFTDQLRKISRDAGMPIQ

GQPCFCKYAQGADSVEPMFKHLKYTYQGLQLVVVILPGKTPVYAEVKRVG

DTVLGMATQCVQVKNVQKTTPQTLSNLCLKINVKLGGVNNILLPQGRPLV

FQQPVIFLGADVTHPPAGDGKKPSIAAVVGSMDAHPSRYCATVRVQQHRQ

<u>D</u>IIQDLATMVRELLIQFYKSTRFKPTRII<u>Y</u>YRDGISEGQFNQVLQHELLA

IREACIKLEKDYQPGITFVVVQKRHHTRLFCMDRNERVGKSGNIPAGTTV

DTKITHPFEFDFYLCSHAGIQGTSRPSHYHVLWDDNHFTSDELQVLTYQL

CHTYVRCTRSVSIPAPAYYAHLVAFRARYHLVDKEHDSAEGSHTSGQSNG

RDQQALAKAVQIHQDTLRTMYFA.

It will be appreciated that position 16 of SEQ ID NO: 1 is position 651 in the full length zebrafish Ago2 polypeptide of SEQ ID NO: 2, and position 45 of SEQ ID NO: 1 is position 680 in the full length zebrafish Ago2 polypeptide of SEQ ID NO: 2. As described herein, native zebrafish Ago2 polypeptide has reduced target sequence slicing efficiency as compared to Ago2 polypeptides expressed by non-teleost species (e.g., mammals, humans, etc.).

In some embodiments, the nucleic acid is the native Ago2 gene of the cell, but it has been genetically modified to include one or more modifications. In certain embodiments, altering the amino acid at position 16 of SEQ ID NO: 1 to glutamate or altering the amino acid at position 45 of SEQ ID NO: 1 to phenylalanine within the zebrafish Ago2 polypeptide increases the target slicing efficiency of zebrafish Ago2 polypeptide. As described in the Examples, Zebrafish Ago2 polypeptides that contained the double substitution drAgo2$^{DY-EF}$ were shown to have activity that approaches that of the human Ago2 protein.

In some embodiments, the genetic modifications to the nucleic acid include modifying the nucleic acid to encode an Ago polypeptide with a glutamate at position 16 of SEQ ID NO: 1, modifying the nucleic acid to encode an Ago polypeptide with a phenylalanine at position 45 of SEQ ID NO: 1, or modifying the nucleic acid to encode an Ago polypeptide with a glutamate at position 16 of SEQ ID NO: 1 and a phenylalanine at position 45 of SEQ ID NO: 1. In other aspects, the nucleic acid encodes a variant of the Ago2 polypeptide that is native to the cell. The variant Ago polypeptide may include a glutamate at position 16 of SEQ ID NO: 1, a phenylalanine at position 45 of SEQ ID NO: 1, or a glutamate at position 16 of SEQ ID NO: 1 and a phenylalanine at position 45 of SEQ ID NO: 1. In some embodiments, one allele or both alleles of the native Ago2 gene have been modified to encode an Ago2 polypeptide having a glutamate at position 16 of SEQ ID NO: 1, a phenylalanine at position 45 of SEQ ID NO: 1, or a glutamate at position 16 of SEQ ID NO: 1 and a phenylalanine at position 45 of SEQ ID NO: 1.

In some aspects, the nucleic acid encodes a polypeptide that is at least 90%, at least 95%, at least 96%, at least 97%, at least 98%, at least 99%, or more identical to a naturally occurring Ago2 polypeptide or a teleost Ago2, where the polypeptide has a glutamate at position 16 of SEQ ID NO: 1, a phenylalanine at position 45 of SEQ ID NO: 1, or has a glutamate at position 16 of SEQ ID NO: 1 and a phenylalanine at position 45 of SEQ ID NO: 1. In certain aspects, the polypeptide includes a sequence that is not found in nature.

In some aspects, a polypeptide (e.g., an Argonaute polypeptide) is at least 90%, at least 95%, at least 96%, at least 97%, at least 98%, at least 99%, or more identical to a naturally occurring Ago2 polypeptide or to a teleost Ago2. In certain aspects, the Argonaute polypeptide is identical to a naturally occurring Ago2 polypeptide, which in some aspects may be encoded by a nucleic acid having an accession number listed in Table 1. In some aspects, a polypeptide is at least 90%, at least 95%, at least 96%, at least 97%, at least 98%, at least 99%, or more identical to a naturally occurring Ago2 polypeptide or to a teleost Ago2, where the polypeptide has a glutamate at position 16 of SEQ ID NO: 1, a phenylalanine at position 45 of SEQ ID NO: 1, or has a glutamate at position 16 of SEQ ID NO: 1 and a phenylalanine at position 45 of SEQ ID NO: 1.

In some embodiments, a genetically modified teleost has at least 90%, at least 95%, at least 99%, or more of the cells expressing an Ago2 polypeptide that is native to a non-teleost organism (e.g., a non-teleost fish, a mammal, or a bird). In alternative embodiments, a genetically modified teleost has at least 90%, at least 95%, at least 99%, or more of the cells expressing a polypeptide that is at least 90%, at least 95%, at least 96%, at least 97%, at least 98%, at least 99%, or more identical to a naturally occurring Ago2 polypeptide.

In some aspects, a nucleic acid is operably linked to an expression control element capable of directing transcription in the teleost cell. The expression control element may include an inducible promoter that is functional in the cell. In some aspects, the nucleic acid is a DNA segment that is integrated into the genome of the cell. In some aspects, the nucleic acid encodes a mammalian, avian, amphibian, reptile, coelacanth, or non-teleost fish Ago2 polypeptide.

In some embodiments, a teleost cell includes (i) a non-endogenous nucleic acid segment that can be transcribed to yield a shRNA that has sequence complementarity to mRNA of a gene, or (ii) a siRNA. In some aspects, the non-endogenous nucleic acid segment is operably linked to an expression control element capable of directing transcription in the cell. In some embodiments, the promoter is an RNA polymerase III promoter. The expression control element includes, for example, an inducible promoter. In some aspects, the nucleic acid segment can be transcribed to yield a shRNA that is integrated into the genome of the cell. In some aspects, the gene is an endogenous gene of the cell.

In some aspects, an expression vector may include a nucleic acid described herein. In certain aspects, a cell may include an expression vector described herein or a nucleic acid described herein. In some aspects, the nucleic acid or vector may be integrated into genome of the cell. In some aspects, a cell (e.g., a teleost cell, a zebrafish cell, etc.) may include a polypeptide described herein. In some aspects, a non-human organism (e.g., a teleost, a zebrafish) includes a nucleic acid, an expression vector, a polypeptide, or a cell that is described herein.

In some embodiments, methods are provided for producing a genetically modified teleost cell that has an increased target slicing ability as compared to an otherwise identical non-genetically modified teleost cell. In certain embodiments, the method includes (a) providing a teleost cell, and (b) modifying the teleost cell so as to cause it to express an Argonaute polypeptide that has increased target slicing ability as compared to the Argonaute2 (Ago2) polypeptide that is native to the cell.

In some aspects, step (b) includes introducing into the teleost cell a nucleic acid that comprises a sequence that encodes the Argonaute polypeptide. In certain aspects, the sequence that encodes the Argonaute polypeptide is operably linked to an expression control element capable of directing transcription in the teleost cell. In other aspects, step (b) includes modifying at least one allele of the endogenous Ago2 gene in the cell so that it encodes an Argonaute polypeptide that has increased target slicing ability as compared to the Ago2 polypeptide that is native to the cell. The Argonaute polypeptide may be native to a non-teleost (e.g., a mammalian or avian Ago2 polypeptide).

In some embodiments, expression of a target sequence in a teleost cell or in a teleost is modulated or inhibited. In certain aspects, a teleost cell or a teleost, such as described herein, is provided. In certain aspects, the teleost cell or teleost is contacted with a siRNA. The siRNA may include a guide strand that is complementary to the target sequence. In alternative aspects, the teleost cell or teleost is provided and a shRNA is expressed. The shRNA may include a guide strand that is complementary to the target sequence in the cell. In some embodiments, the guide strand includes a mismatch with respect to the target sequence. The mismatch may be located within nucleotides 2 to 7 of the guide sequence, or in alternative aspects, may be located at position 6. In certain embodiments, the mismatch may be a guanine-guanine mismatch.

In some embodiments, the function of a gene in a teleost cell or in a teleost may be examined. In certain aspects, a teleost cell or a teleost, such as described herein, is provided. In some aspects, the teleost cell or teleost is contacted with a siRNA. The siRNA may include a guide strand that is complementary to the target sequence. In some aspects, at least one phenotype of the cell (e.g., a cell of the teleost) is observed, thereby examining the function of the gene. In alternative aspects, the teleost cell or teleost is provided and a shRNA is expressed. The shRNA may include a guide strand that is complementary to the target sequence in the cell (e.g., a cell of the teleost). In some aspects, at least one phenotype of the cell (e.g., a cell of the teleost) is observed, thereby examining the function of the gene.

In certain embodiments, the target sequence is or encodes a homolog of a mammalian sequence characterized in that mutation of, or altered expression or activity of, the mammalian sequence is associated with a condition. In some aspects, inhibition of the target sequence will result in a phenotype that corresponds to a phenotype characteristic of a mammalian condition.

In some embodiments, the teleost cell or teleost is contacted with a test agent. The effect of the agent on the phenotype of the teleost or teleost cell may then be evaluated. In some aspects, the test agent may be identified as a candidate therapeutic agent. The test agent may be a candidate therapeutic agent for treating a condition if the test agent reduces the severity of the phenotype.

In some embodiments the teleost is a fish species that is used as a food for humans or in animal feed, e.g., a salmon, trout, herring, perch, tuna, cod, mackerel, flounder, or bass. In some embodiments the teleost is an aquarium fish. In some embodiments, RNAi may be used in a teleost as described herein to identify genes that confer susceptibility to a pathogen. In some embodiments, RNAi may be used in a teleost as described herein to identify genes that confer improved properties. Such improved properties may include increased resistance to a pathogen, increased ability to withstand unfavorable environmental conditions, decreased ability to take up or concentrate environmental toxins, etc.

It should be appreciated that wherever the present disclosure describes compositions or methods relating to a teleost cell or teleost, the teleost cell or teleost may be of any species of teleost. In some embodiments, the teleost is a zebrafish (*Danio rerio*). In some embodiments, the teleost is a medaka (*Oryzias latipes*). Zebrafish and medaka are useful, e.g., model organisms for the study of mammalian (e.g., human) biology and disease. In some embodiments, RNAi may be used in a teleost as described herein to generate a model of a mammalian condition. For example, RNAi may be used to inhibit expression of a homolog of a mammalian gene whose reduced function is at least in part responsible for causing a condition. In some embodiments, the resulting teleost having reduced expression of a target gene has a disease-related phenotype. In some embodiments, the resulting teleost having reduced expression of a target gene and a disease-related phenotype may be used in screening to, e.g., identify test agents that reduce the severity of the phenotype. Such agents may be candidate agents to treat the disease.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

Specific examples of these methods are set forth below in the Examples.

EXAMPLES

Introduction

Diverse RNA-silencing pathways play important roles in transposon silencing, viral defense, heterochromatin formation, and posttranscriptional repression of cellular genes (Tomari and Zamore, 2005; Malone and Hannon, 2009). In the simplest of these pathways, RNA interference (RNAi), a Dicer endonuclease cleaves long, double-stranded RNA (dsRNA) into small interfering RNAs (siRNAs) that associate with an Argonaute (Ago) protein to guide the Ago-catalyzed slicing of transcripts with extensive pairing to the siRNA (Tolia and Joshua-Tor, 2007). The RNAi pathway arose early in eukaryotic evolution and has been retained by most eukaryotic lineages (Shabalina and Koonin, 2008). Some lineages also have derivative silencing pathways that are more elaborate and involve other types of guide RNAs, such as Piwi-interacting RNAs (piRNAs), which derive from single-stranded rather than dsRNA (Weick and Miska, 2014; Iwasaki et al., 2015), or microRNAs (miRNAs), which derive from short hairpins rather than long dsRNA (Bartel, 2004). Despite their differences, the RNA-silencing pathways have each retained at their core a silencing complex that contains a short (20-32-nt) RNA associated with an Argonaute homolog. Within this complex, the RNA provides sequence specificity through direct pairing with target transcripts, and the Argonaute homolog either slices the target precisely between the nucleotides that pair to residues 10 and 11 of the guide RNA (Tuschl, 2001; Song et al., 2004) or recruits other proteins to promote other types of repression (Weick and Miska, 2014; Iwasaki et al., 2015; Jonas and Izaurralde, 2015).

The miRNA pathway is the dominant RNA-silencing pathway of mammalian somatic cells. Indeed, most cellular mRNAs are conserved regulatory targets of conserved mammalian miRNAs (Friedman et al., 2009). The miRNA silencing complex targets these mRNAs at sites that fall primarily in 3' untranslated regions (3' UTRs) and perfectly pair to nucleotides 2-7 of the miRNA, known as the miRNA seed (Bartel, 2009). Pairing to the seed region is insufficient to trigger slicing of the mRNA target and instead destabilizes the mRNA through an interaction between Ago and a glycine-tryptophan-repeat (GW) protein that recruits factors that accelerate poly(A)-tail shortening, triggering subsequent decapping and degradation of the mRNA (Jonas and Izaurralde, 2015). An additional but minor component of repression occurs through translational repression (Eichhorn et al., 2014).

Although the vast majority of miRNA regulatory sites in mammalian mRNAs have little more than seed pairing, some have the extensive complementarity required for Argonaute-catalyzed slicing. For example, in mouse embryos, miR-196 directs the cleavage of the HoxB8 3' UTR at a site that has near-perfect complementarity to miR-196 and is conserved throughout most vertebrate species, including zebrafish (Yekta et al., 2004). To date, however, only 21 cleavage targets of mammalian miRNAs have been found (Davis et al., 2005; Shin et al., 2010; Hansen et al., 2011). Moreover, despite a high degree of homology among the four mammalian Argonaute proteins (Ago1, Ago2, Ago3, and Ago4), only Ago2 has retained slicing activity (Liu et al., 2004; Meister et al., 2004). Restoring activity to the other three paralogs requires a combination of changes that either restore the residues of the DEDH catalytic tetrad within the PIWI domain (Ago1 and Ago4), restore two structural elements (NTI and NTII) in the N domain (Ago1, Ago3, and Ago4), restore a short sequence cluster in the PIWI domain (Ago1), or remove a short insertion close to the glutamate of the catalytic center (Ago4) (Faehnle et al., 2013; Hauptmann et al., 2013; Nakanishi et al., 2013; Hauptmann et al., 2014).

The ability to slice rare extensively paired miRNA targets is not the only reason that Ago2 has retained its ability to cleave RNA. This activity is also required for the unusual biogenesis of miR-451, a miRNA conserved among vertebrates (Cheloufi et al., 2010; Cifuentes et al., 2010; Yang and Lai, 2010; Yang et al., 2010). Most metazoan miRNAs are produced from the successive cleavage by Drosha and Dicer, two endonucleases with dual RNase III domains (Kim, 2005). Drosha first cleaves both strands near the base of the stem to liberate the pre-miRNA hairpin from the primary transcript, and then Dicer cleaves both strands near the loop to generate the miRNA duplex, which contains the mature miRNA paired with 2-nt 3' overhangs to an RNA segment from the other arm of the hairpin. This duplex is then loaded into Ago such that the miRNA strand ultimately becomes the guide RNA, and the other strand is discarded. In mammals, fish, and presumably other vertebrate species, miR-451 biogenesis is unusual in that the pre-miR-451 hairpin, with its stem of only 17 bp, is too short to be cleaved by Dicer and is instead loaded into Ago, which cleaves the strand opposite the miRNA strand in an activity analogous to mRNA slicing (Cheloufi et al., 2010; Cifuentes et al., 2010; Yang and Lai, 2010). Following this cleavage, 3' exonucleolytic resection generates the mature miR-451 miRNA (Yoda et al., 2013). Because miR-451 activity is required for proper erythropoiesis (Patrick et al., 2010; Rasmussen et al., 2010), mice with Ago2 mutations that abrogate slicing are anemic, as are fish lacking the full-length Ago2 protein (Cheloufi et al., 2010; Cifuentes et al., 2010).

In some mammals, Ago2-catalzed slicing also plays a critical role in the RNAi pathway. Although this pathway is not typically found in somatic cells, endogenous siRNAs are observed in certain mouse cells, including oocytes, embryonic stem cells, and male germ cells (Babiarz et al., 2008; Tam et al., 2008; Watanabe et al., 2008; Song et al., 2011). The pathway is important in mouse oocytes; disabling the Ago2 active site desilences transposon expression, causing meiotic defects and female sterility (Stein et al., 2015). However, whether RNAi plays such a critical role in other mammals is unclear, as the Dicer isoform primarily responsible for the production of murine siRNAs does not appear to be present outside of the Muridae family (Flemr et al., 2013).

Regardless of why Ago2 has retained slicing activity, be it to cleave a few miRNA targets, to enable miR-451 biogenesis, or to perform RNAi-mediated transposon control, the widespread presence of this activity in mammalian cells has greatly benefited biomedical research. Indeed, the ability of artificial siRNAs to direct mRNA slicing, discovered 15 years ago (Elbashir et al., 2001a), has transformed the way that biologists study mammalian gene function. The reason that these artificial siRNA duplexes are so effective is that they resemble endogenous miRNA duplexes and thereby become incorporated into the Ago2 silencing complex to direct the slicing of target mRNAs. For previously unknown reasons, however, RNAi is not an effective tool for gene-knockdown experiments in zebrafish (Oates et al., 2000; Mangos et al., 2001; Zhao et al., 2001; Gruber et al., 2005; Kelly and Hurlstone, 2011).

We discovered why RNAi is so ineffective in zebrafish: Two point substitutions that apparently occurred in a teleost ancestor ~0.3 billion years ago crippled the slicing activity of zebrafish Ago2 (drAgo2). The crippling effect of these substitutions raised the question of how these fish are able to produce sufficient miR-451, which requires Ago2-catalyzed cleavage for its biogenesis. When answering this question, we found that a G-G mismatch involving position 6 of the miRNA substantially enhances both the cleavage of fish pre-miR-451 and the slicing of bound target transcripts. Our results indicate how RNAi might be restored to zebrafish and reveal an unanticipated feature of guide-RNA pairing, showing that non-Watson-Crick seed geometry is optimal for slicing bound target.

Example 1

Ineffective Slicing but Detectable Pre-miR-451 Cleavage in Zebrafish

Although evidence for slicing activity has been observed in zebrafish embyros injected with a miRNA duplex and complementary substrate (Cifuentes et al., 2010; Giraldez et al., 2005), efforts to detect endogenous miR-196-directed cleavage at the extensively paired site within the HoxB8 mRNA were unsuccessful in zebrafish (S. Yekta & D. P. B, unpublished results). A potential reason for this discrepancy was that the injection experiment looked for cleavage products in early embryos, whereas the attempts to detect endogenous miR-196-directed cleavage looked later in development. To investigate this possibility, we assayed for miR-430-directed cleavage in zebrafish embyros (FIG. 1A). RNA with perfect complementarity to the dominant isoform of miR-430 was injected into single-cell zebrafish embryos. Embryos were then harvested at 4 hours post-fertilization (4 hpf), a stage at which miR-430 dominates the endogenous miRNA pool, and total RNA was extracted and analyzed on RNA blots. No cleavage was detected, even when an mRNA encoding additional zebrafish Ago2 (drAgo2) was co-injected into the one-cell embryo (FIG. 1B). In contrast, cleavage was readily detected when mRNA for human Ago2 (hsAGO2) was co-injected, provided that the RNA did not have mismatches at the cleavage site (10-11 mm), which confirmed that the conditions within the embryo were conducive to authentic slicing (FIG. 1B).

We attempted to reconcile these results with those previously reported using an injected miRNA duplex and complementary target. A perfect or mismatched target was co-injected with or without miR-1 duplex alone, as was done previously (Cifuentes et al., 2010; Giraldez et al., 2005). In addition, we tried injecting additional drAgo2 mRNA and also injected hsAGO2 mRNA as a positive control.

Figure 1C:
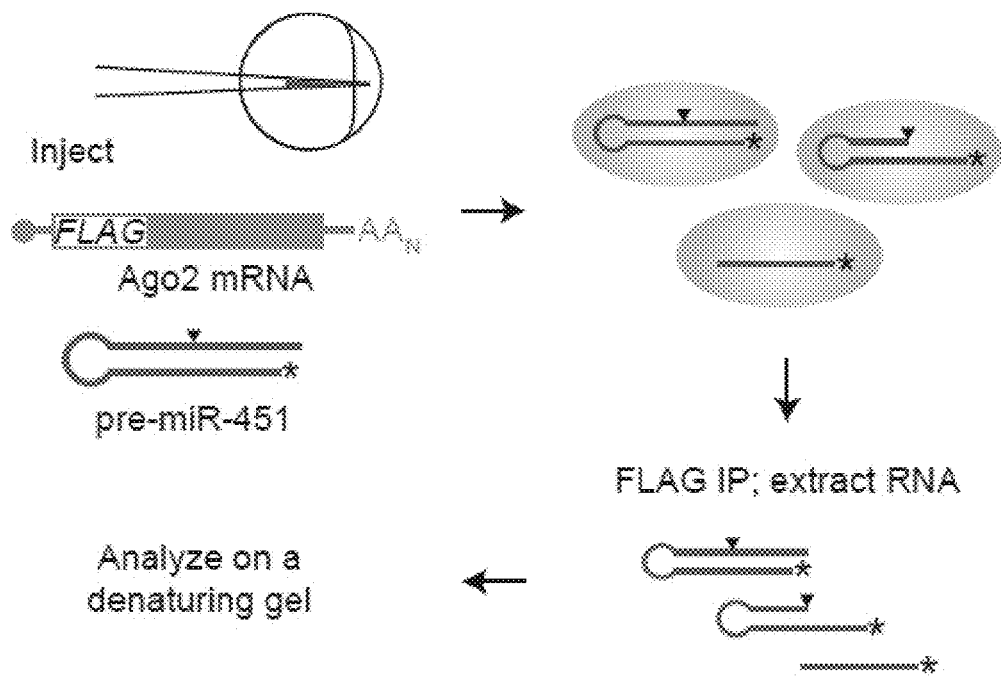
Figure 1D:
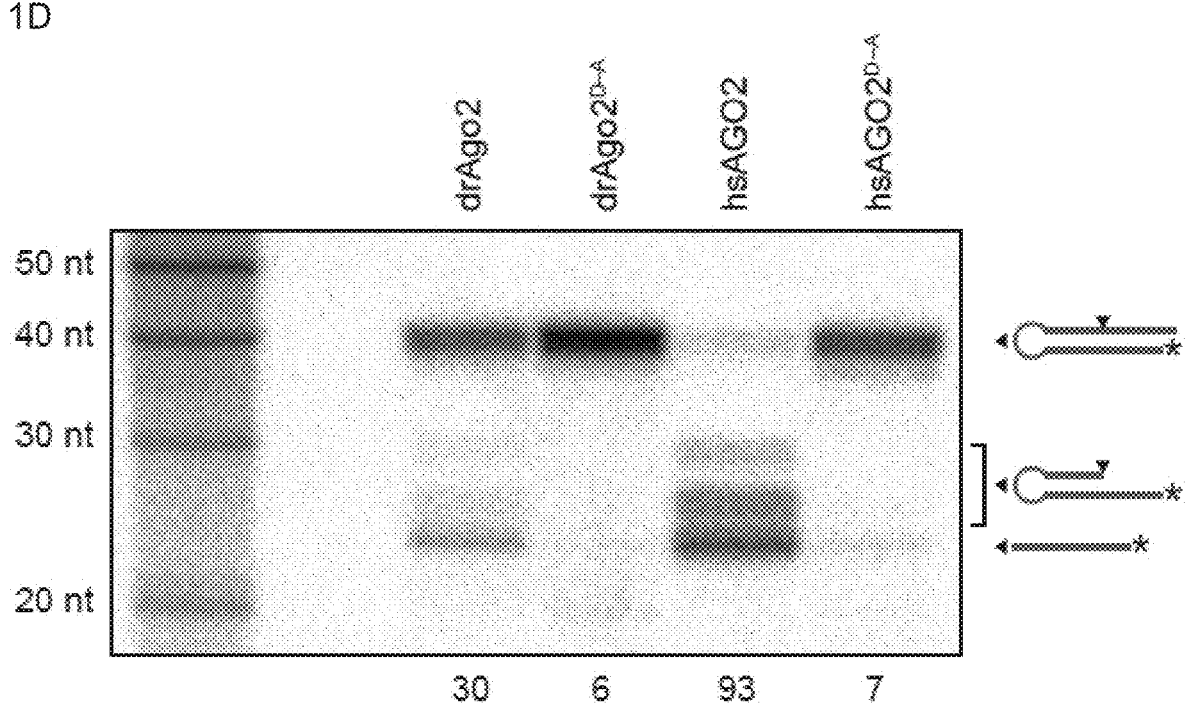

The inability to observe drAgo2-catalyzed slicing explained why no endogenous products of slicing have been reported in zebrafish, why RNAi is described as impractical, inviable, and unreliable for knocking down gene expression in zebrafish (Kelly and Hurlstone, 2011), and perhaps why morpholino antisense reagents have instead been so popular. This ineffective slicing was nonetheless surprising, because a reaction analogous to slicing is required for miR-451 biogenesis in zebrafish (Cifuentes et al., 2010), which prompted us to examine the ability of drAgo2 to process pre-miR-451. Accordingly, we developed an assay for pre-miR-451 binding and cleavage, in which mRNA for tagged Ago2 was co-injected with 5' end-labelled pre-miR-451 into single-cell embryos. RNA co-purifying with Ago2 was then isolated and analyzed on a denaturing gel (FIG. 1C). Consistent with the genetic results (Cifuentes et al., 2010), drAgo2 was able to bind and cleave pre-miR-451 (FIG. 1D). However, cleavage was not as efficient as that observed with hsAGO2 (FIG. 1D). Interestingly, some mature miR-451 was also observed with Ago2 active-site mutants (Ago$^{D-A}$, in which a critical aspartate was changed to alanine REF), presumably through cleavage by another endonuclease in the loop of the injected pre-miRNA (FIG. 1D). However, the amount of cleaved pre-miR-451 associated with drAgo2 was substantially greater, which indicated that drAgo2 was indeed able to cleave the pre-miRNA, albeit at lower efficiency than observed for hsAGO2.

Two Substitutions in a Teleost Ancestor Explain the Loss of Efficient Slicing

Figures 2A, 2B, 2C:
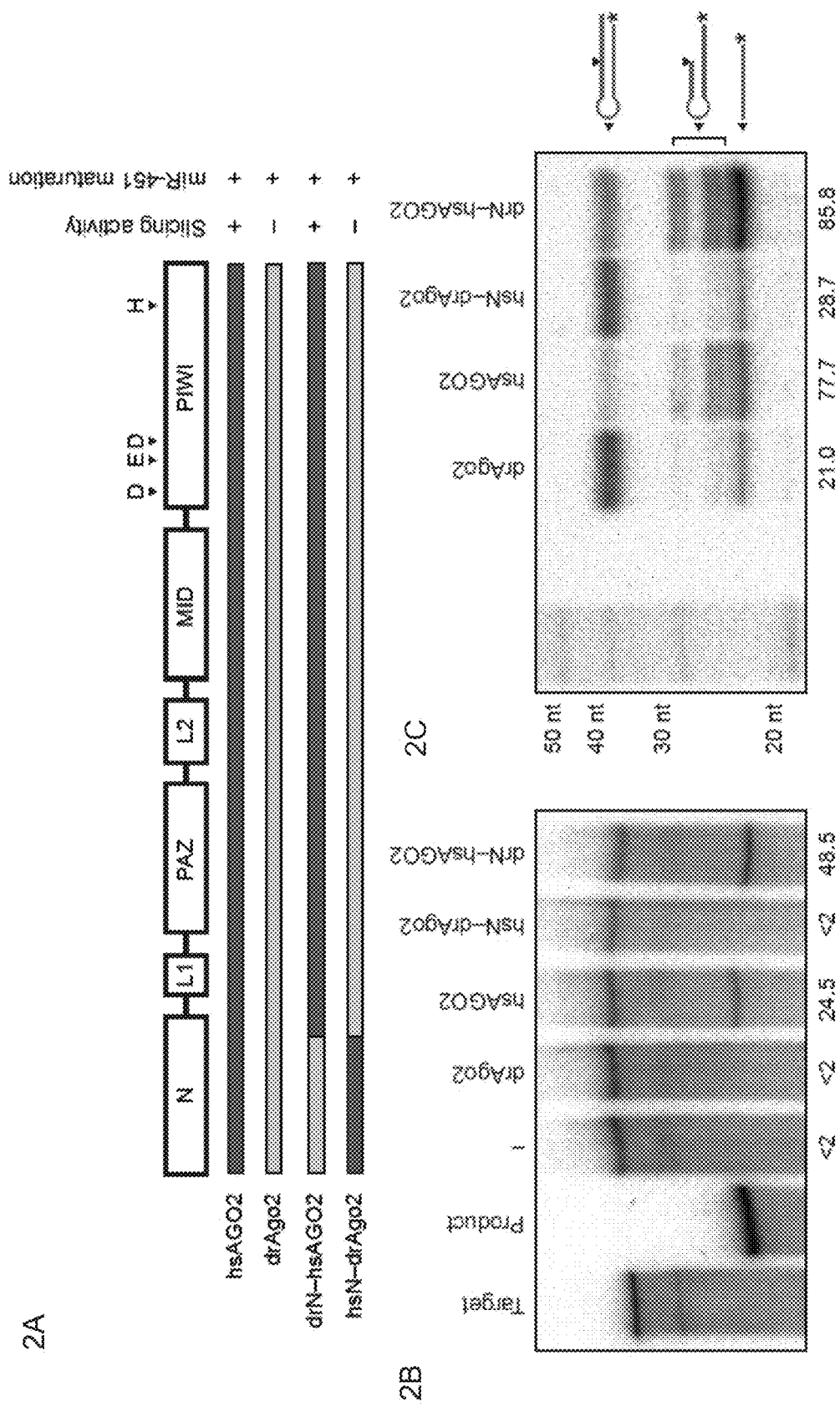

A search for differences that might explain the loss of efficient slicing in zebrafish showed that drAgo2 and hsAGO2 differ mainly in their amino-terminal N domains. Because changes in the N domains help explain the loss of slicing activity of hsAgo1, hsAgo3, and hsAgo4 (Faehnle et al., 2013; Hauptmann et al., 2013; Hauptmann et al., 2014; Nakanishi et al., 2013), we swapped the N domains of drAgo2 and hsAGO2 and examined the activity of these chimeric proteins (FIG. 2A). drAgo2 with a human N domain was not substantially better at either slicing or pre-miR-451 binding and cleavage, and hsAGO2 with the zebrafish N domain had no worse activity in these assays (FIG. 2B, FIG. 2C). These results indicated that differences outside the drAgo2 N domain were inhibiting endonuclease activity.

To search for the key differences outside the N domain, we compared Ago2 sequences from 11 vertebrate species. Assuming the most parsimonious evolutionary scenario, in which 1) slicing was lost only once in the vertebrate clade and 2) mammals have retained the ancestral slicing activity that is present in invertebrates and throughout most eukaryotes, we surmised that slicing must have been lost at some point in the jawed-fish lineage that gave rise to zebrafish, after the common ancestor of humans and zebrafish (FIG. 2D, highlighted lineage of cladogram). By this reasoning, the substitution that compromised slicing would be at a position that is identical in lamprey and the Sarcopterygii (Ceolacanth and tetrapods) but differs in zebrafish. A focus on positions outside the N domain narrowed the candidates to 20, all of which had conservative amino acids changes, and most of which were on the surface of the protein. Of the few in the protein interior, the two best candidates for explaining the loss of efficient slicing were near the active site (FIG. 2E). Indeed, one was the glutamate (E) previously found to complete a DEDH catalytic tetrad (Nakanishi et al., 2012). In zebrafish and other representatives of the teleost clade, this active-site glutamate changed to an aspartate (D), a potentially benign substitution, as it retained an acidic side chain. The second was a nearby residue that changed from phenylalanine (F) to tyrosine (Y) in zebrafish and other representatives of the teleost clade, also a potentially benign substitution.

Figure 2F:
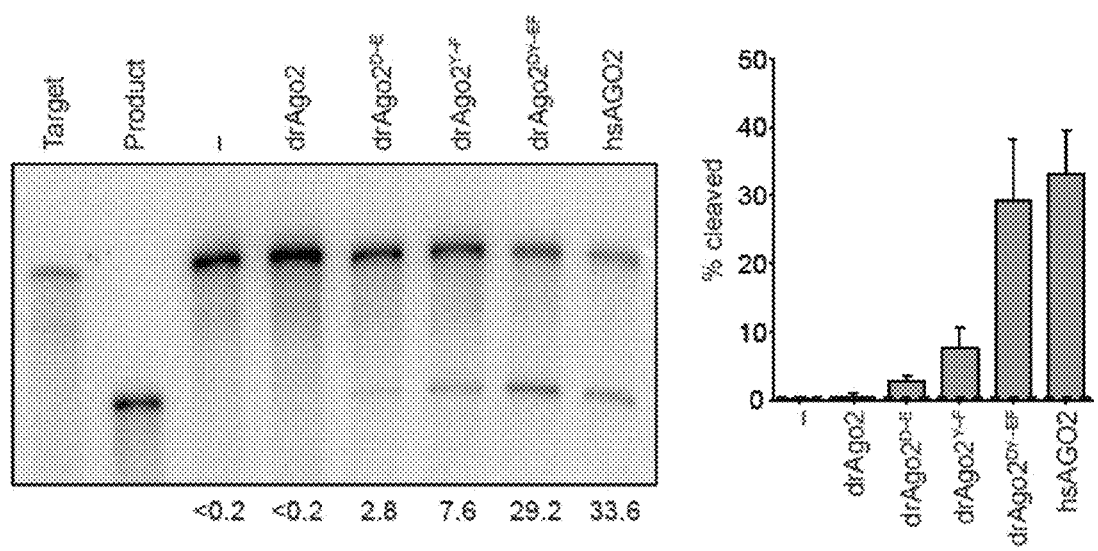
Figure 2G:
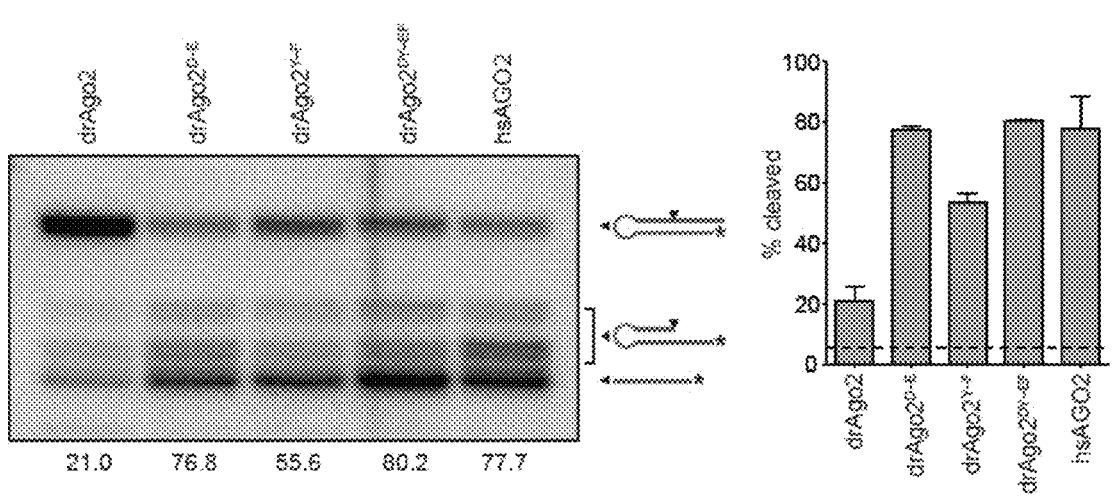

To test the effect of these two substitutions, we made mRNAs that encoded drAgo2 proteins that contained either of the single or the double substitution, drAgo2$^{D-E}$, drAgo2$^{Y-F}$, and drAgo2$^{DY-EF}$, and examined the endonuclease activity of these proteins for both in vivo slicing and pre-miR-451 cleavage. Each of the single substitutions imparted detectable slicing activity to the zebrafish protein, and the double substitution imparted activity that approached that of the human protein (FIG. 2F). Moreover, the reciprocal human-to-zebrafish substitutions within hsAGO2 eliminated detectable slicing activity. Analogous results were observed for pre-miR-451 cleavage, except the drAgo2$^{D-E}$ single substitution on its own was sufficient to approach the hsAGO2 activity, perhaps because of a narrower dynamic range for this assay (FIG. 2G). Together, these results showed that E-to-D and F-to-Y substitutions were both responsible for the loss of detectable slicing in zebrafish embryos.

With the exception of a presumed D-to-E reversion in a Perciformes subclade, both the E-to-D and F-to-Y substitutions were present in all teleost species examined, including representatives of three of the four teleost subgroups, which included the vast majority of the extant teleost fish and all of those that have been sequenced (Broughton et al., 2013). Because these substitutions did not extend to more basal jawed fish, represented by gar (FIG. 2D), they presumably occurred approximately 300,000,000 years ago, in a common ancestor of most extant teleosts.

An Ancestral G-G Mismatch within Pre-miR-451 Enhances Cleavage

The observation that drAgo2 catalyzed detectable pre-miR-451 cleavage in the embryo yet did not catalyze detectable slicing prompted us to explore the differences between the substrates of these two cleavage reactions. Apart from the loop, the most prominent structural difference was at miRNA position 6, which was paired to a C in the slicing substrate but formed a G-G mismatch with G35 in the zebrafish pre-miR-451 hairpin. Interestingly, G35 changed to a C in an amniote ancestor that gave rise to reptiles, birds, and mammals, thereby changing the ancestral G-G mismatch to a Watson-Crick pair (FIG. 3A), as occurs in our slicing substrate. Although C35 has been retained within most amniote lineages, it changed again in some, most often to a U, but occasionally back to a G. For example, all three possibilities are observed within primates, with humans and most other apes acquiring the U, gibbons retaining the C, and old-world monkeys reverting back to the G. Structure-function studies of human pre-miR-451 show that changing U35 to either a G or an A slightly enhances miR-451 activity in HeLa cells (Yang et al., 2012). This increased activity corresponds to increased miR-451 accumulation, which is attributable to more efficient resection of cleaved pre-miR-451 (Yang et al., 2012). These experiments comparing the human G-U wobble to the G-G and G-A mismatches at positions 6 and 35, respectively, establish an interesting tolerance for mismatches at this position, raising the question of how the G-C Watson-Crick match, which is found in most amniotes but untested in previous studies, might compare with the ancestral G-G mismatch.

Figures 3B, 3C:
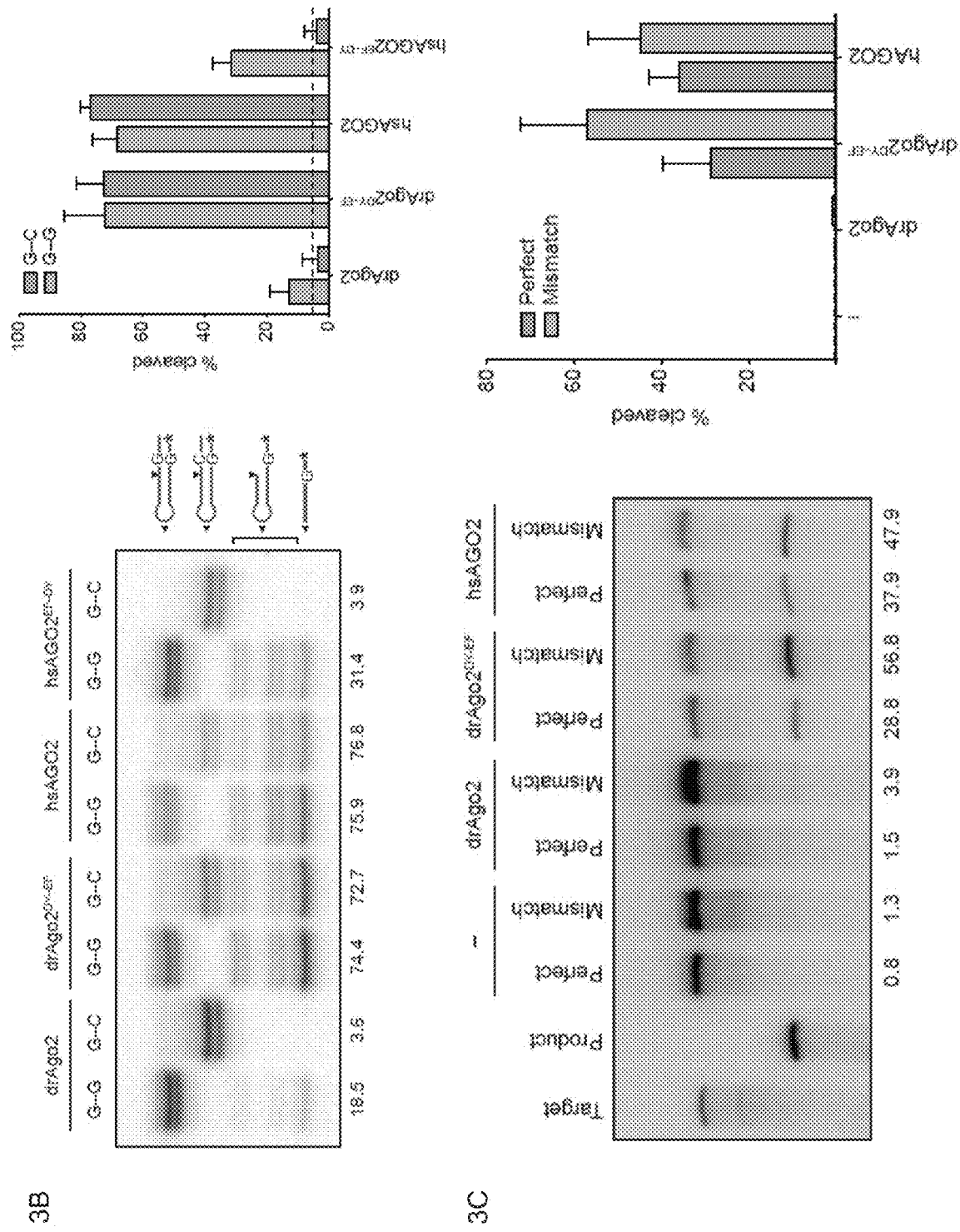

To answer this question, we tested ancestral and amniote pre-miR-451 structures in our assay for pre-miR-451 binding and cleavage, and found that drAgo2 had a surprising preference for the mismatch of the ancestral structure (FIG. 3B). Indeed, although drAgo2 could bind the G-C structure, cleavage did not exceed the background level observed for the D-to-A active-site mutants (FIG. 1D, FIG. 3B). The same result was observed for the hsAGO2 with the zebrafish substitutions hsAGO2$^{EF-DY}$ (FIG. 3B). However, drAgo2$^{DY-EF}$, which had the key substitutions reverted to the ancestral residues, and wild-type hsAGO2 did not distinguish between the G-G and G-C structures, perhaps again reflecting a limited dynamic range of this assay. We speculate that the benefit of retaining a G-G mismatch allowed the teleost Argonaute2 to retain the ability to process enough pre-miR-451 to avoid erythropoiesis defects despite having lost the ability to perform efficient slicing.

A G-G Mismatch at Position 6 of the Guide RNA Enhances Slicing

Intrigued by the strong benefit of the G-G mismatch for drAgo2-catalyzed pre-miR-451 cleavage, we tested whether an analogous mismatch might also enhance target slicing. Indeed, altering the injected miR-430 slicing target, substituting a G for the C in that normally pairs to G6 of miR-430, led to detectable drAgo2-catalzyed slicing in the zebrafish embryo (FIG. 3C). Slicing by the drAgo2$^{DY-EF}$ and hsAGO2 might also have increased with the G-G mismatch, although variability in the assay made this potential improvement difficult to ascertain with confidence.

Figure 4A:
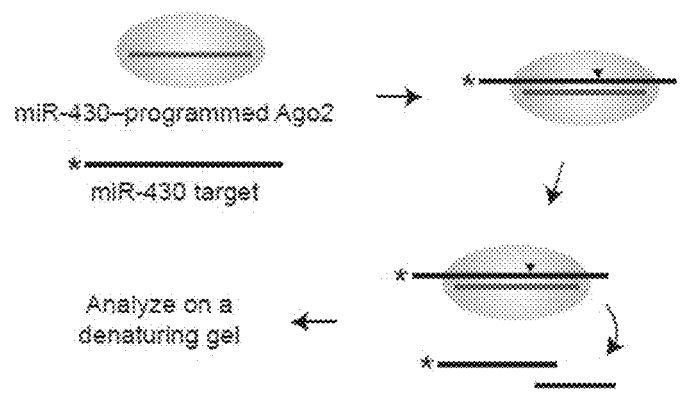
FIGS. 4A-4C depict in vitro slicing reactions quantify both the detrimental effects of the teleost Ago2 substitutions and beneficial effects of the G-G target mismatch.
Figure 4B:
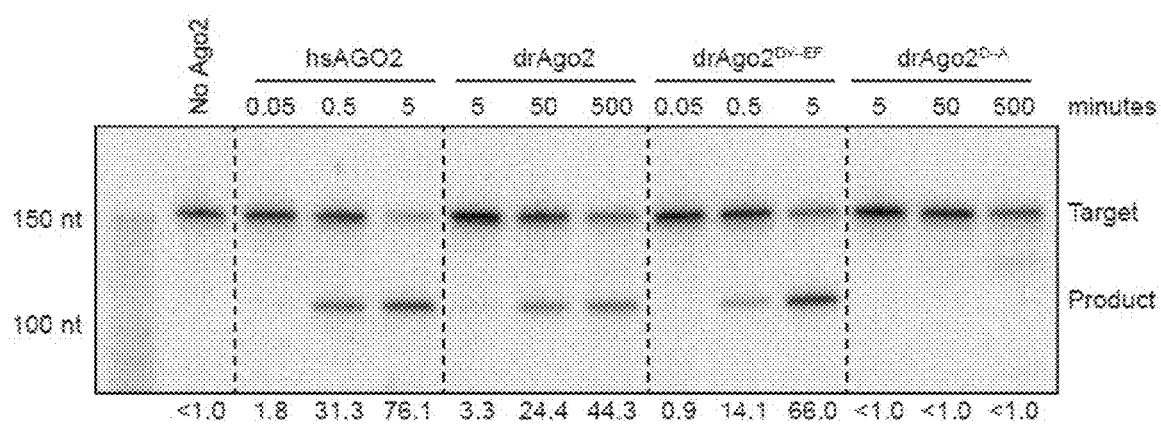

Detectable drAgo2-catalzyed slicing of the substrate that had the G-G mismatch suggested that drAgo2-catalzyed slicing of a perfectly paired substrate might also be detected with a more sensitive assay. Accordingly, we adapted the protocol of Flores-Jasso et al. (2013) to purify the different Ago2 proteins loaded with miR-430 and then measured their ability to slice an end-labeled, perfectly paired substrate in vitro (FIG. 4A). In this more sensitive assay, drAgo2-catalyzed slicing was detectable but >100-fold slower than hsAGO2-catalyzed slicing (FIG. 4B, compare the 24% reacted for drAgo2 at 50 minutes with the 31% reacted for hsAGO2 at 0.5 minutes). As expected, this slicing activity was largely restored when using the repaired zebrafish protein and abolished when mutating another active-site residue (FIG. 4B, drAgo2$^{DY-EF}$ and drAgo2$^{D-A}$, respectively).

Figure 4C:
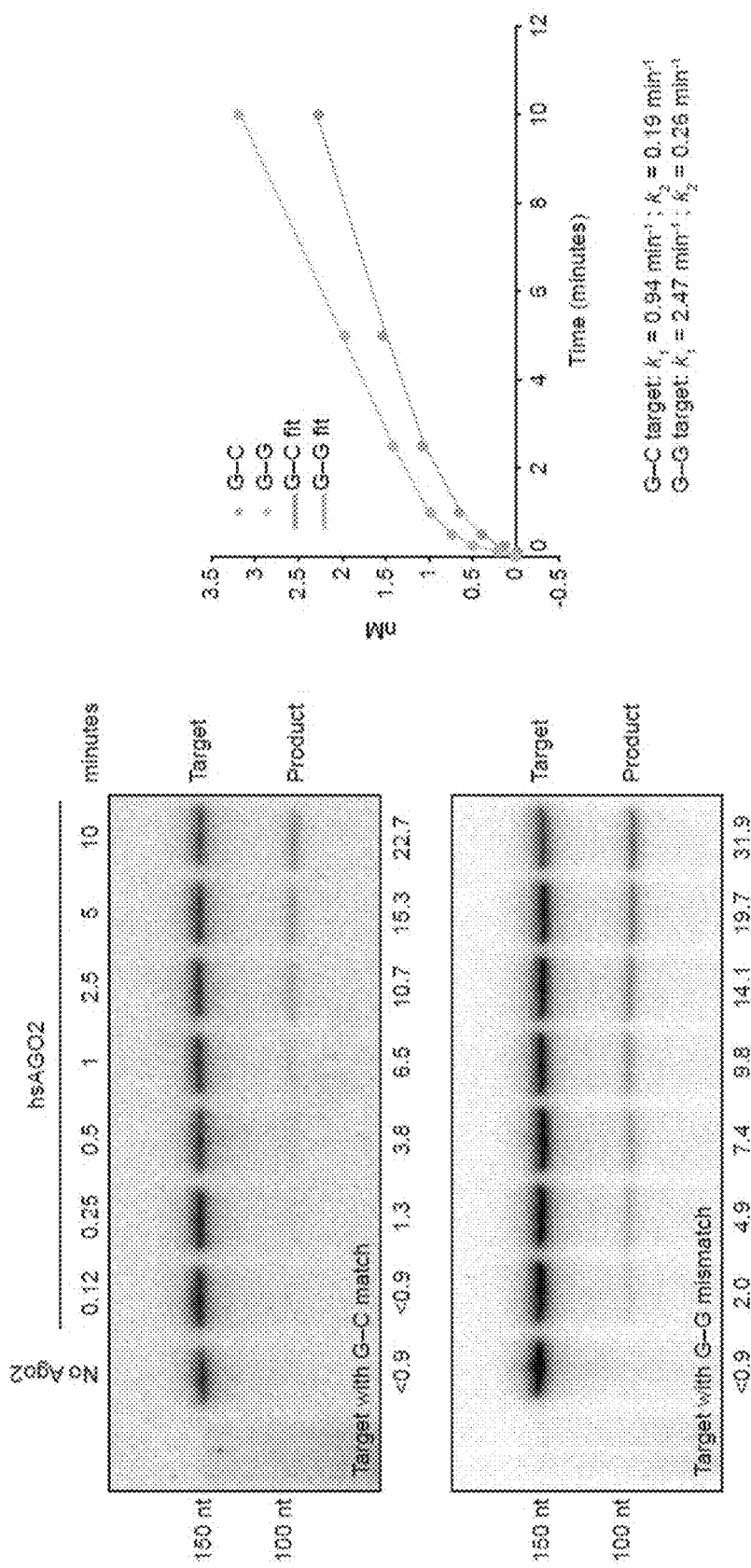

We next tested the effects of the G-G mismatch on slicing by hsAGO2 loaded with miR-430, performing multiple-turnover reactions and comparing a target with a perfectly paired site to one with a single-nucleotide substitution that created a G-G mismatch with position 6 of miR-430. For both targets, accumulation of product was biphasic, with an initial burst of rapid slicing that proceeded until the product concentration approached the enzyme concentration, which was the behavior expected for rate-limiting product release (FIG. 4C). The initial rate ($k_1$) was 2.5-fold higher for the substrate with the G-G mismatch, which implied that under these conditions, this mismatch increased the overall rate of target binding and slicing. In addition, the second rate for this substrate was also somewhat faster than that of the fully matched substrate ($k_2$=0.26 and 0.19 min$^{-1}$, respectively), which implied that following miR-430-guided slicing, the G-G mismatch had a favorable effect on the rate-limiting step of product release.

siRNAs and shRNAs are important research tools for gene-knockdown studies, and siRNAs are showing promise in the clinic. In the current design of siRNAs (and shRNAs), pairing to the last few nucleotides of the guide is considered unimportant (Elbashir et al., 2001), as is pairing to the first nucleotide of the guide, which is bound to Ago2 in a configuration that prevents pairing to the mRNA (Ma et al., 2005; Parker et al., 2005). However, the remainder of the guide is typically perfectly complementary to the target mRNA. Perfect pairing to the seed region of the guide RNA (nucleotides 2-8) is considered particularly important for the initial recognition of the target transcript, while pairing to the central region (nucleotides 9-12) is considered particularly important for slicing (Salomon et al., 2015; Wee et al., 2012). Knowledge that mismatches between the guide and target can enhance product dissociation rates and thereby potentially increase the multiple turnover rate of slicing (Wee et al., 2012) is not typically exploited to improve these reagents, perhaps out of concern that the benefits of multiple-turnover would be offset by less efficient target binding or slicing. We have discovered that a G-G mismatch at position 6 of the guide differs from previously characterized mismatches in that it can confer a net benefit in target binding and slicing. Therefore, designing a G-G mismatch at guide position 6 will improve the efficacy of siRNAs and shRNAs.

In the context of the miR-430 guide, this mismatch also modestly improved the multiple-turnover slicing rate, and we propose that it would enhance multiple turnover more substantially when placed in contexts for which release of the perfectly paired 3' cleavage fragment more severely limited multiple turnover. This strategy for enhancing turnover is expected to be particularly useful for improving siRNAs with nucleotide modifications that help protect them from nucleases, as these modifications often also enhance pairing stability, which slows turnover.

A G-G mismatch at position 6 of the guide is unusual in conferring a net benefit in target binding and slicing. Other mismatches or wobbles at position 6 may provide similar benefits. In addition, mismatches or wobbles at one or more other positions might provide this previously unanticipated improved efficacy.

Example 2

Ineffective Slicing in Zebrafish

Figure 5A:
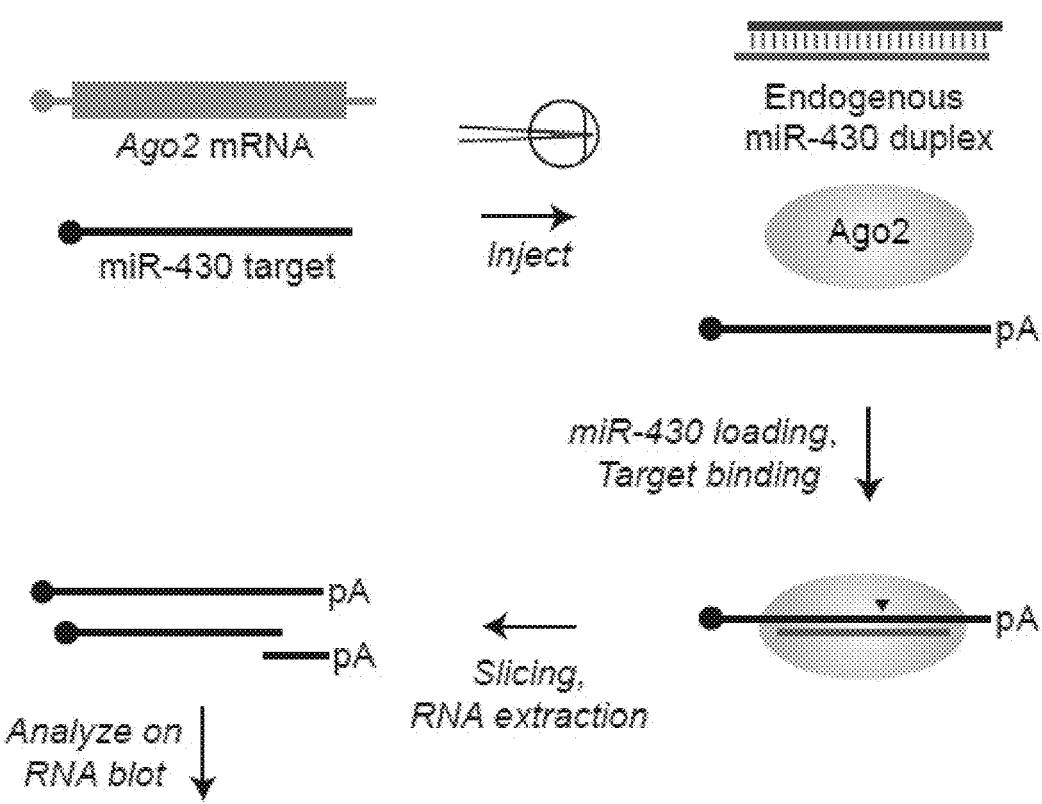
FIGS. 5A-5B depict ineffective slicing by drAgo2 in zebrafish embryos.
Figure 5B:
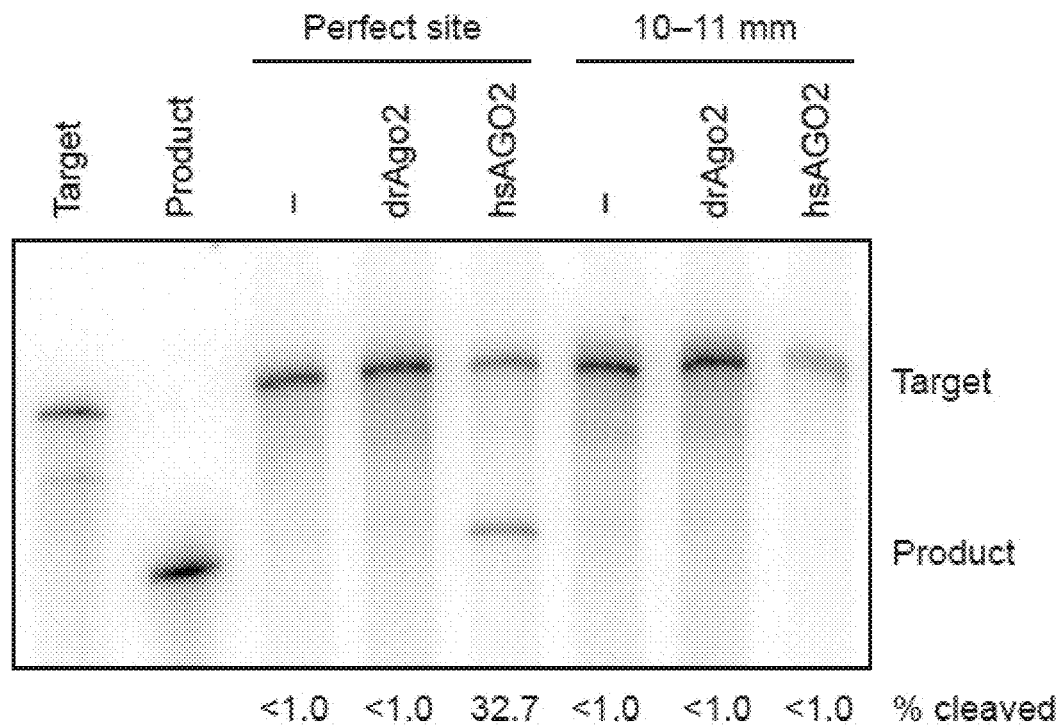
Figure 10A:
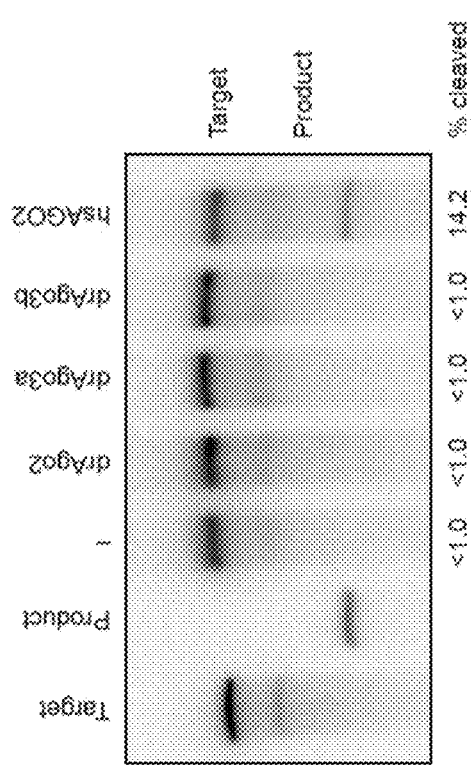
FIGS. 10A-10B depict drAgo2 is the only catalytically active Ago protein in zebrafish.
Figure 10B:
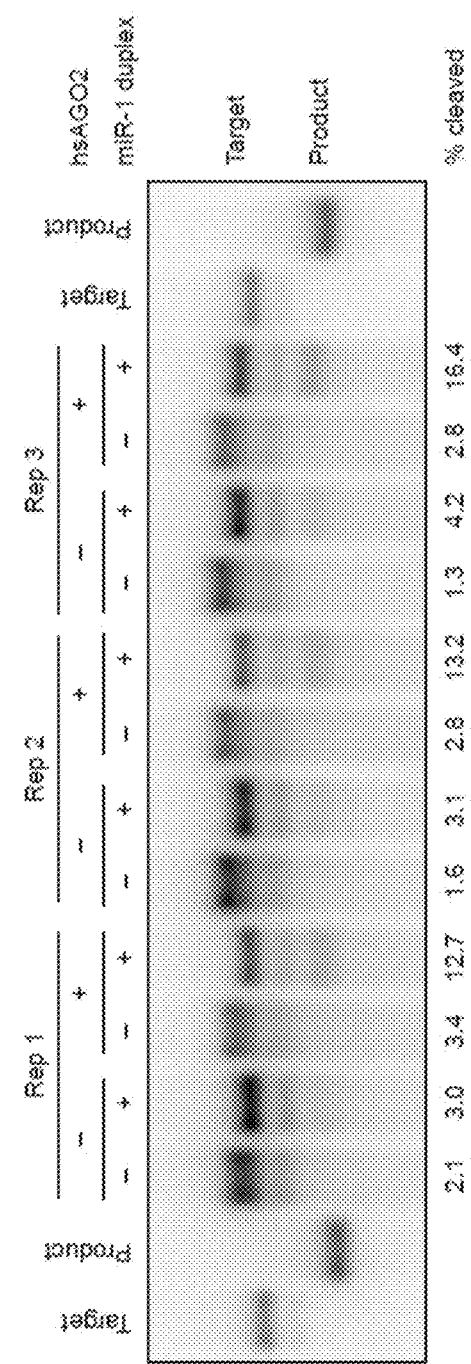

Although miR-196-directed slicing at the extensively paired site within the HoxB8 mRNA is readily detected in mouse embryos (REF), analogous efforts to detect slicing at the orthologous site within HoxB8b were unsuccessful in zebrafish embryos (S. Yekta & D. P. B., unpublished data). When considering this result together with the ineffectiveness of RNAi as a gene-knockdown tool in zebrafish, we decided to investigate the slicing ability of zebrafish Argonaute2 (drAgo2). We first assayed for miR-430-directed slicing in zebrafish embryos (FIG. 5A). Capped RNA with a single site perfectly complementarity to the dominant isoform of miR-430 was injected into single-cell zebrafish embryos. Embryos were then harvested at 4 hours post-fertilization (4 hpf), a stage at which miR-430 dominates the endogenous miRNA pool, and total RNA was extracted and analyzed on RNA blots. No slicing was detected, even when an mRNA encoding additional drAgo2 was co-injected into the one-cell embryo (FIG. 5B). In contrast, slicing was readily detected when mRNA for human Ago2 (hsAGO2) was co-injected, provided that the mRNA did not have mismatches at the cleavage site (10-11 mm), confirming that the conditions within the embryo were conducive to authentic slicing (FIG. 5B). Additional experiments confirmed that slicing activity had not been transferred to another zebrafish Ago paralog (FIG. 10A). Together, these data suggest that zebrafish Ago2 slicing activity is significantly reduced compared to that of the human protein.

Two Substitutions in a Teleost Ancestor Explain the Loss of Efficient Slicing

Figure 11A:
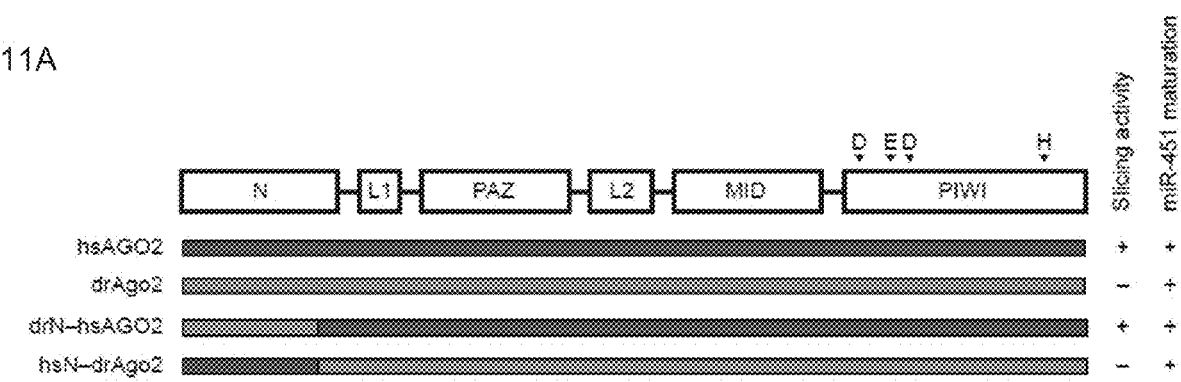
FIGS. 11A-11C depict exploration of differences in the N domain as a source of reduced catalytic activity.
Figure 11B:
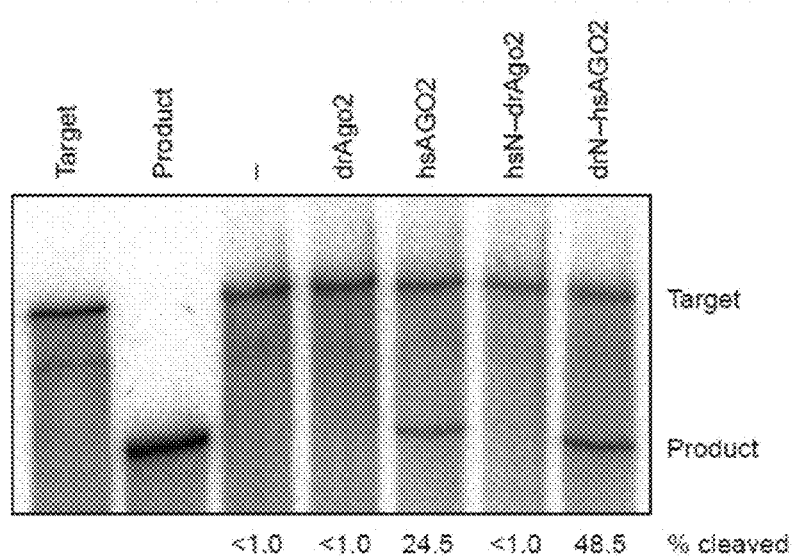

A search for differences that might explain the loss of efficient slicing in zebrafish started with the observation that drAgo2 and hsAGO2 differ mainly in their amino-terminal (N) domains and the knowledge that changes in the N domains explained the loss of slicing activity of hsAGO1, hsAGO3, and hsAGO4 (Faehnle et al., 2013; Hauptmann et al., 2013; Hauptmann et al., 2014). However, when we swapped the N domains of drAgo2 and hsAGO2 and examined the activity of these chimeric proteins using our assay for miR-430-guided slicing (FIG. 11), drAgo2 with a human N domain was not substantially better at slicing, and hsAGO2 with the zebrafish N domain had no worse activity, indicating that differences outside the drAgo2 N domain were inhibiting slicing activity (FIG. 11B).

Figure 6A:
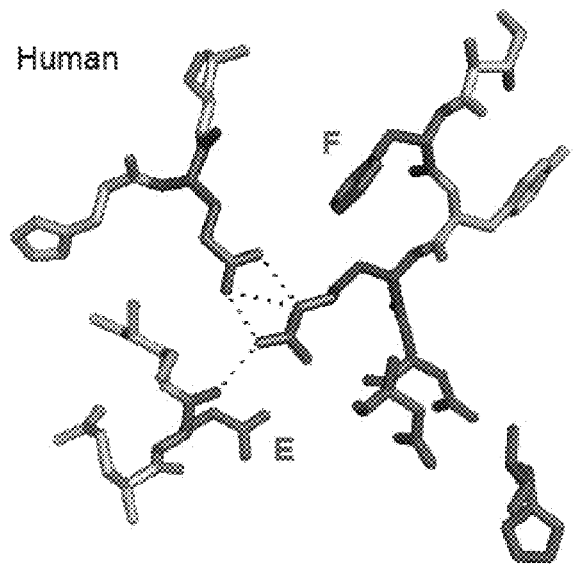
FIGS. 6A-6E depict two point substitutions that explain the effective slicing by drAgo2.
Figure 6B:
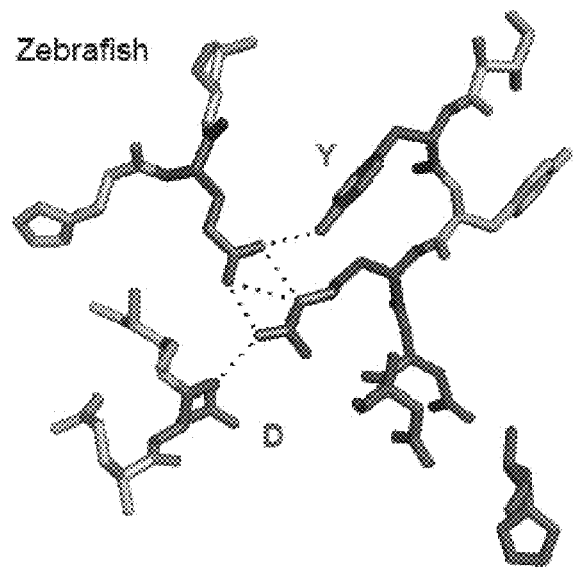

To search for differences outside the N domain that might explain the loss of efficient slicing, we compared Ago2 sequences from 11 vertebrate species. Assuming the most parsimonious evolutionary scenario, in which 1) efficient slicing was lost only once in the vertebrate clade, and 2) mammals have retained the ancestral slicing activity that is present in invertebrates and throughout most eukaryotes, we surmised that efficient slicing must have been lost at some point in the jawed-fish lineage that gave rise to zebrafish, after the common ancestor of humans and zebrafish (FIG. 6A, highlighted lineage of cladogram). By this reasoning, any substitution that compromised slicing in zebrafish would be at a residue that is identical in lamprey and the Sarcopterygii (ceolacanth and tetrapods) but differs in zebrafish. These criteria narrowed the number of candidate substitutions to 20, all of which imparted conservative amino acid changes, and most of which were at residues on the surface of the protein. Of the three at interior residues, the two best candidates for explaining the loss of efficient slicing were near the active site (FIG. 6B). Indeed, one changed the active-site glutamate (E), previously found to complete a DEDH catalytic tetrad (Nakanishi et al., 2012); in zebrafish and other representatives of the teleost clade, this E changed to an aspartate (D). The second changed a nearby phenylalanine (F) to tyrosine (Y), and this change also occurred in all representatives of the teleost clade.

Figure 6C:
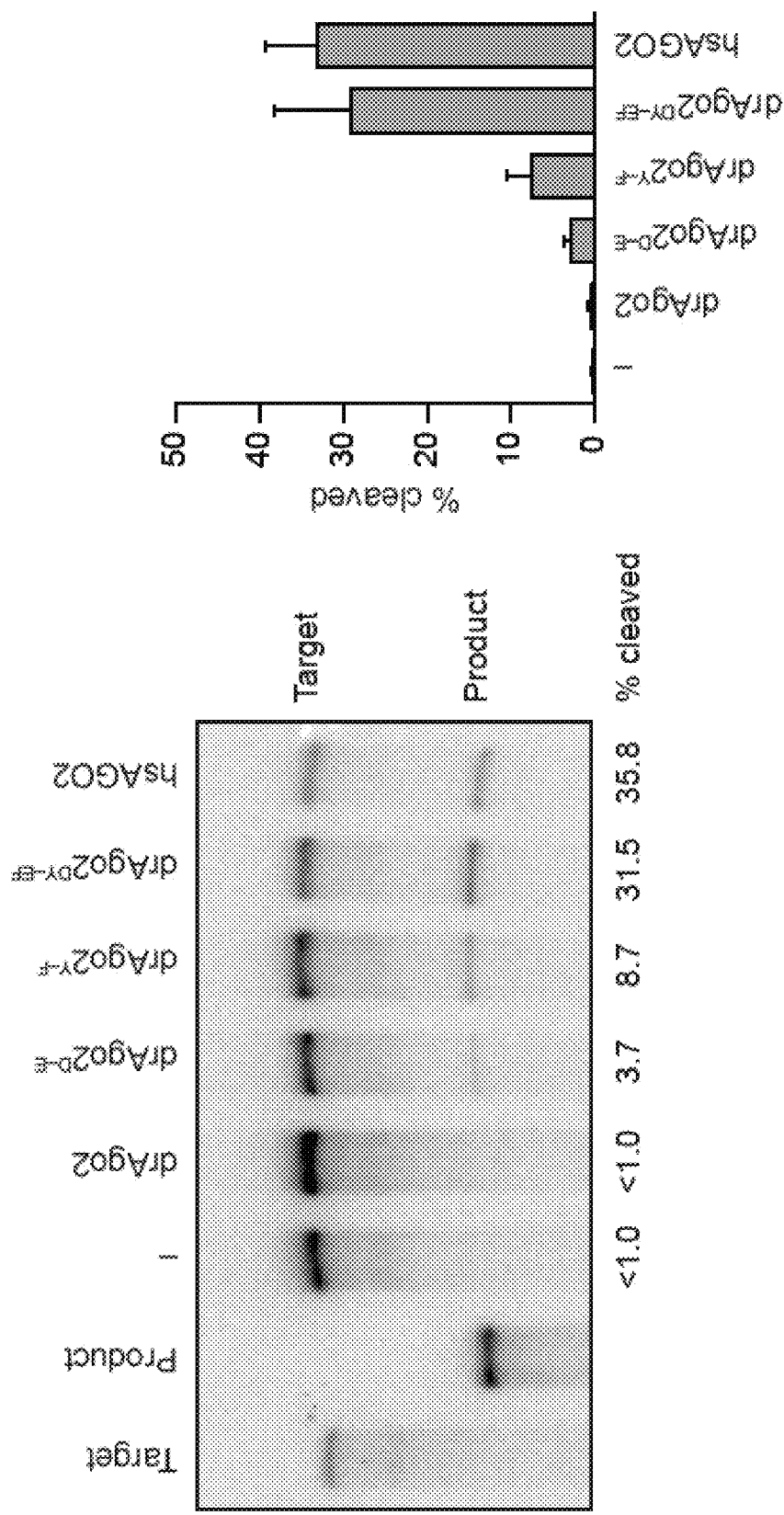
Figure 12A:
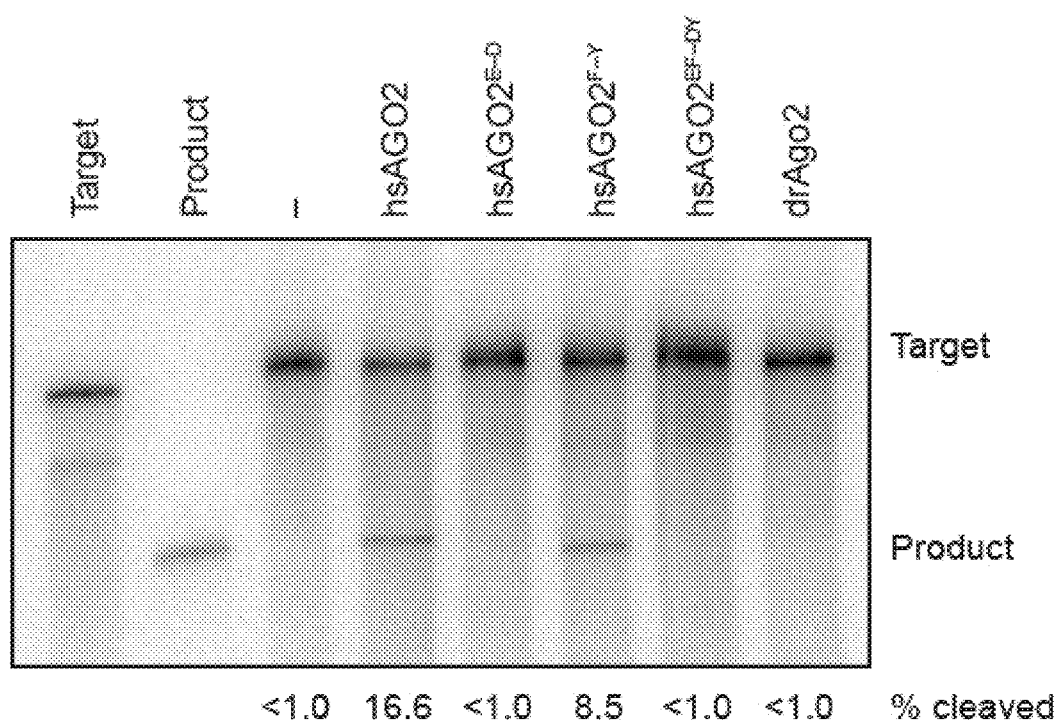
FIGS. 12A-12B depict widespread presence of crippling substitutions among teleost fish.

To test the effect of these two substitutions, we made mRNAs that encoded drAgo2 proteins with the D and Y reverted back to their ancestral identities and examined the ability of these proteins to slice a miR-430 target. Each of the single reversions (drAgo2$^{D-E}$ and drAgo2$^{Y-F}$) conferred detectable slicing activity to the zebrafish protein, and the double reversion (drAgo2$^{DY-EF}$) imparted activity approaching that of the human protein (FIG. 6C). Moreover, the reciprocal human-to-zebrafish substitutions within hsAGO2 eliminated detectable miR-430-guided slicing activity (FIG. 12A). Together, these results showed that E-to-D and F-to-Y substitutions both contributed to the loss of efficient slicing in zebrafish embryos.

Figures 6D, 6E:
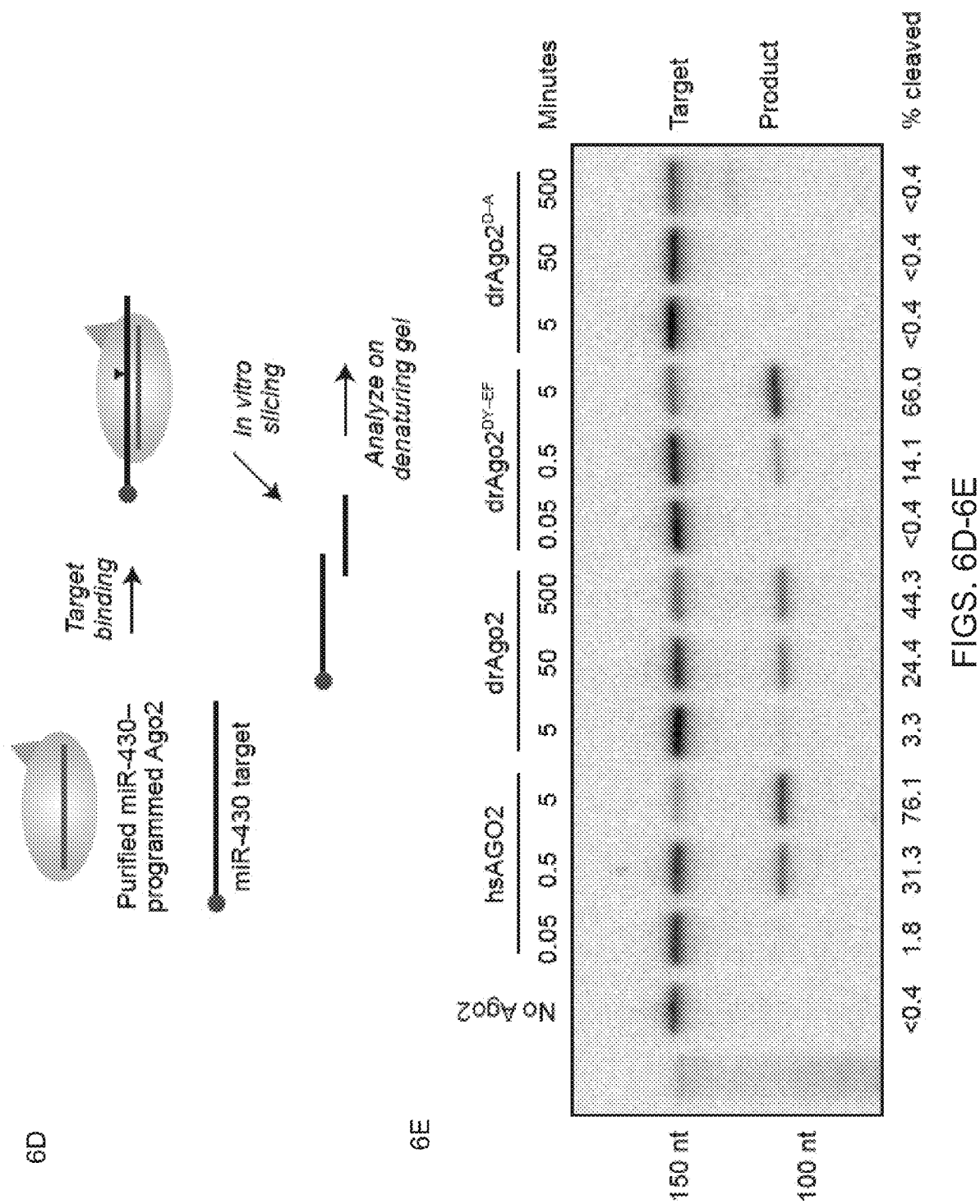

Although our assay within zebrafish embryos had the advantage of examining slicing under physiological conditions, its dynamic range was narrow, with only a ~50-fold difference separating the hsAGO2 activity from the lower limit of detection. Moreover, the in vivo setting of the developing embryo, with its large number of seed-matched miR-430 targets, its unknown amount of loaded Ago2 that varied over time, and its dynamic nuclease activities, prevented quantitative analysis of slicing kinetics. Therefore, to supplement the in vivo analyses, we adapted the protocol of Flores-Jasso et al. (2013) to purify the different Ago2 proteins loaded with miR-430 and then measured their ability to slice a cap-labeled substrate in vitro (FIG. 6D). To isolate the slicing step from the substrate-binding and product-release steps, we monitored single-turnover reactions in which each miR-430-programed Ago2 variant was in 10-fold excess over the slicing substrate and in even greater excess over the enzyme-substrate dissociation constant ($K_D$), expected to be in the low-picomolar range (Wee et al., 2012). In this more sensitive assay, drAgo2-catalyzed slicing was detectable but <1% as rapid as hsAGO2-catalyzed slicing (FIG. 6E, compare the 0.24 fraction reacted for drAgo2 at 50 minutes with the 0.31 fraction reacted for hAGO2 at 0.5 minutes). As expected, this slicing deficit was largely restored when reverting the two key residues to their ancestral identities (drAgo2$^{DY-EF}$), and abolished when mutating another active-site residue, in which the first aspartate of the DEDH catalytic tetrad was changed to alanine (drAgo2$^{D-A}$) (FIG. 6E).

Figure 12B:
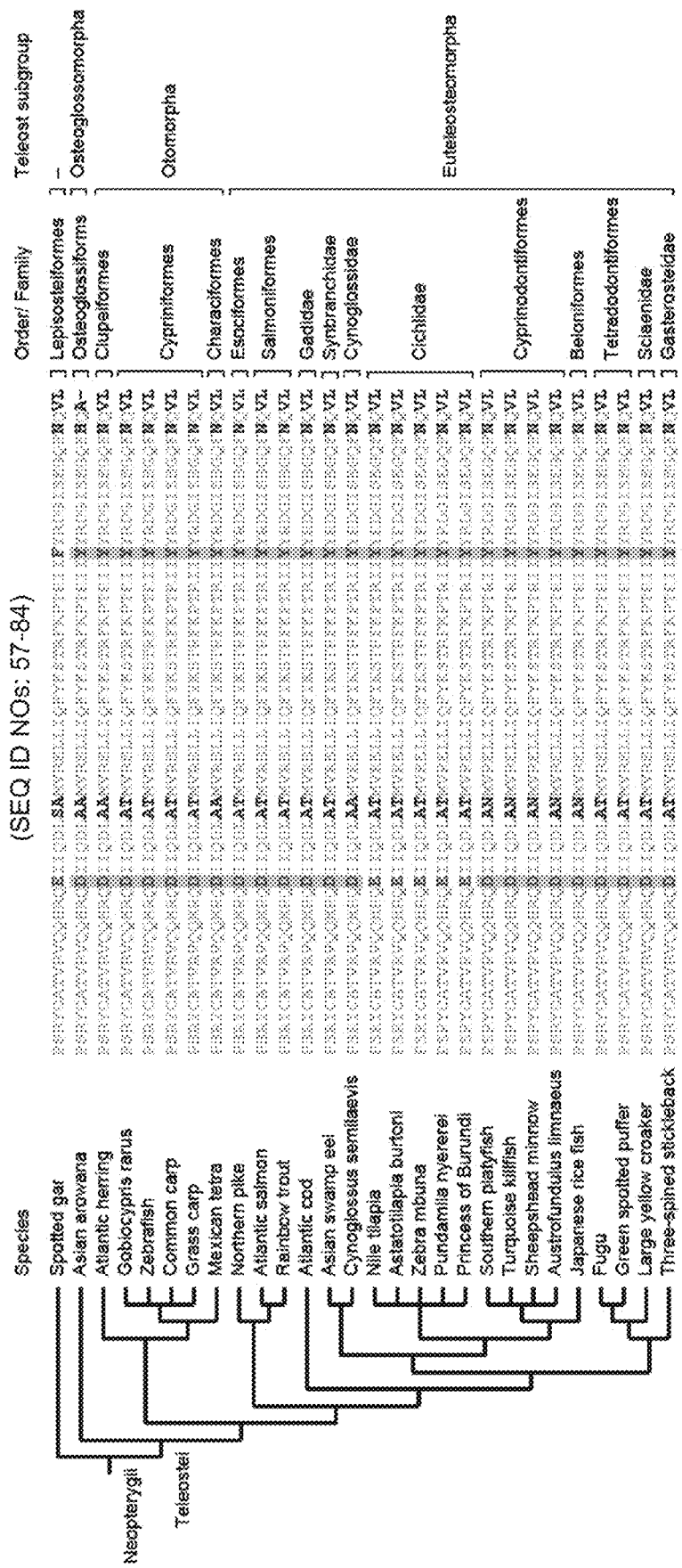

The E-to-D and F-to-Y substitutions, which together imparted this >100-fold diminution in slicing activity, are broadly distributed among teleost fish, which comprise most of the extant fish species. With the exception of a presumed D-to-E reversion in a Perciformes subclade, both the E-to-D and F-to-Y substitutions were present in all 29 teleost species examined (FIG. 12B). These 29 species included all teleosts with sequenced genomes and fell within the three teleost subgroups that encompass the vast majority of the extant teleost species (Broughton et al., 2013). Because these substitutions did not extend to more basal jawed fish, represented by gar (FIG. 6A), they presumably occurred approximately 300,000,000 years ago, in a common ancestor of most extant teleosts.

An Ancestral G-G Mismatch within Pre-miR-451 Enhances Cleavage

Figure 7A:
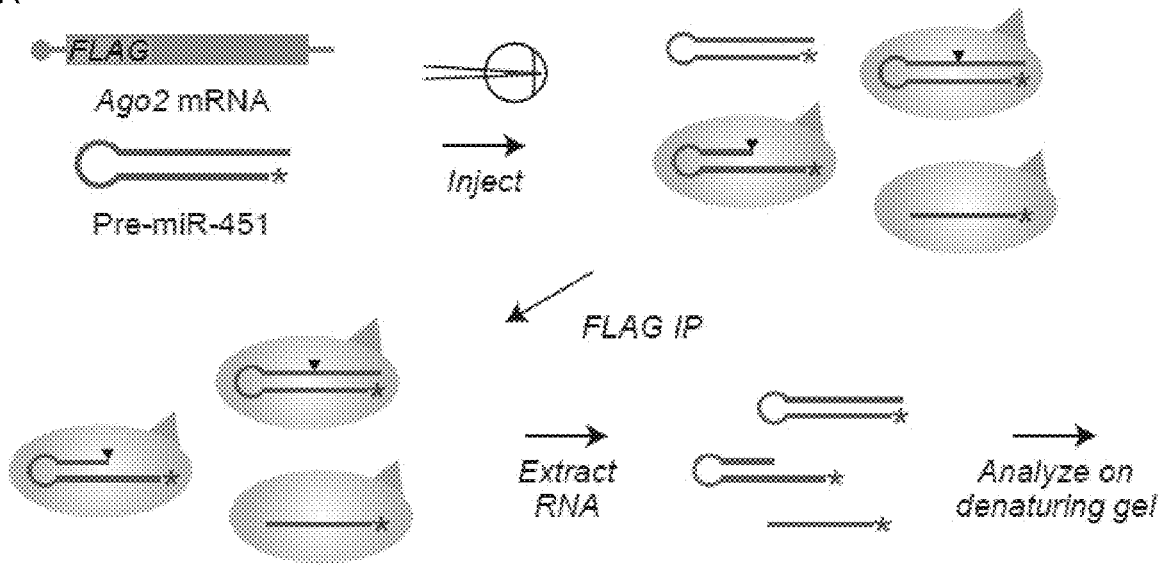
FIGS. 7A-7E depict a G-G mismatch that promotes maturation of fish pre-miR-451.
Figure 7B:
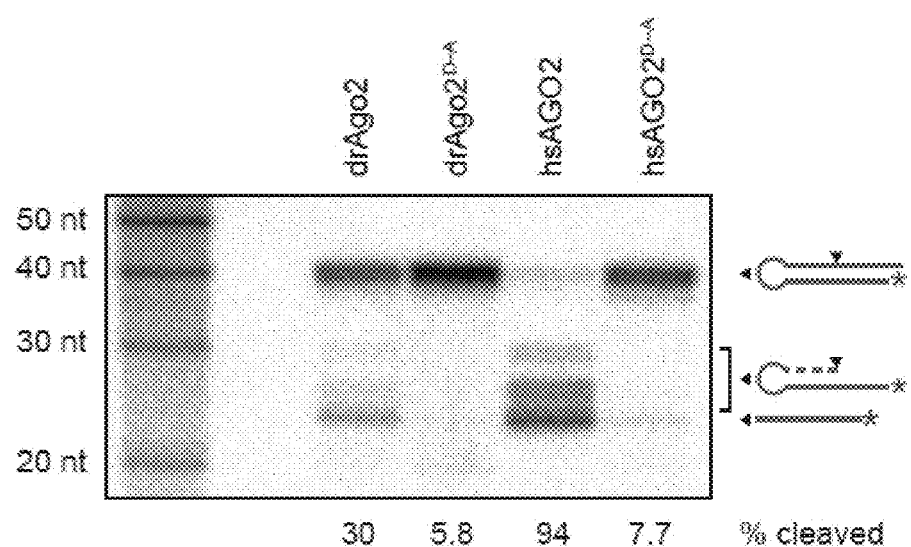
Figure 11C:
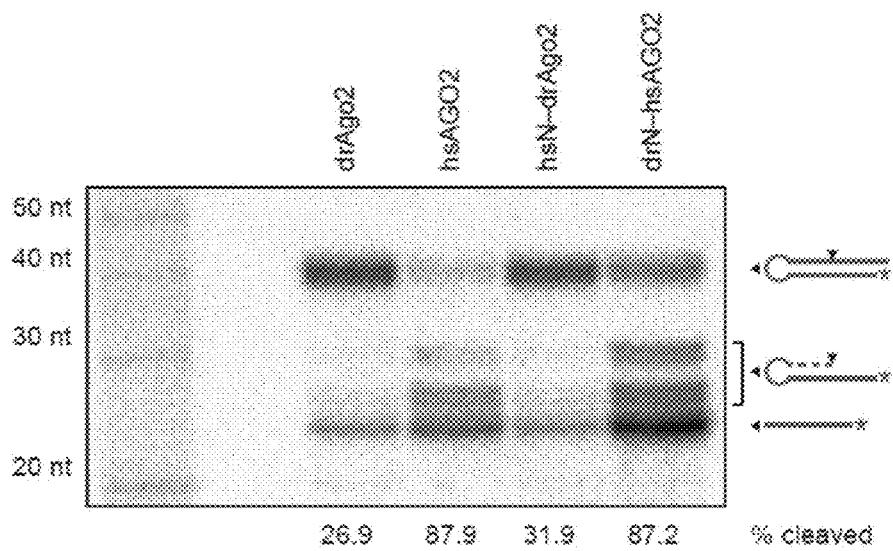

The inefficiency of drAgo2-catalyzed slicing explained why endogenous slicing products have not been reported in zebrafish, why RNAi is described as an ineffective tool for knocking down gene expression in zebrafish (Oates et al., 2000; Mangos et al., 2001; Zhao et al., 2001; Gruber et al., 2005; Kelly and Hurlstone, 2011), and why morpholino antisense reagents have instead been so popular. This inefficient slicing was nonetheless unexpected because genetic analyses indicate that a reaction analogous to slicing is required for miR-451 biogenesis in zebrafish (Cifuentes et al., 2010), which prompted us to examine further the ability of drAgo2 to process pre-miR-451. To do this, we developed an assay for pre-miR-451 binding and cleavage, in which mRNA for FLAG-tagged Ago2 was co-injected with 5' end-labeled pre-miR-451 into single-cell embryos, and then RNA co-purifying with Ago2 was isolated and analyzed on a denaturing gel (FIG. 7A). Consistent with the genetic results (Cifuentes et al., 2010), wild-type drAgo2 was able to bind and cleave pre-miR-451, although cleavage was not as efficient as that observed with hsAGO2 (FIG. 7B). Interestingly, some mature miR-451 was also detected with Ago2 active-site mutants (Ago2$^{D-A}$) (FIG. 7B), perhaps the result of cleavage within the loop of the injected pre-miRNA by another endonuclease. However, the amount of cleaved pre-miR-451 associated with wild-type drAgo2 was substantially greater, indicating that drAgo2 was indeed able to cleave the pre-miRNA, albeit at lower efficiency than that observed for hsAGO2 (FIG. 7B). As observed for slicing, this lower efficiency of drAgo2-mediated pre-miR-451 cleavage was attributed to the E-to-D and F-to-Y substitutions found in zebrafish and other teleosts, in that activity for the constructs with single and double reversions of these substitutions approached that of hsAGO2 (FIG. 7C, FIG. 11C).

Figures 7C, 7D:
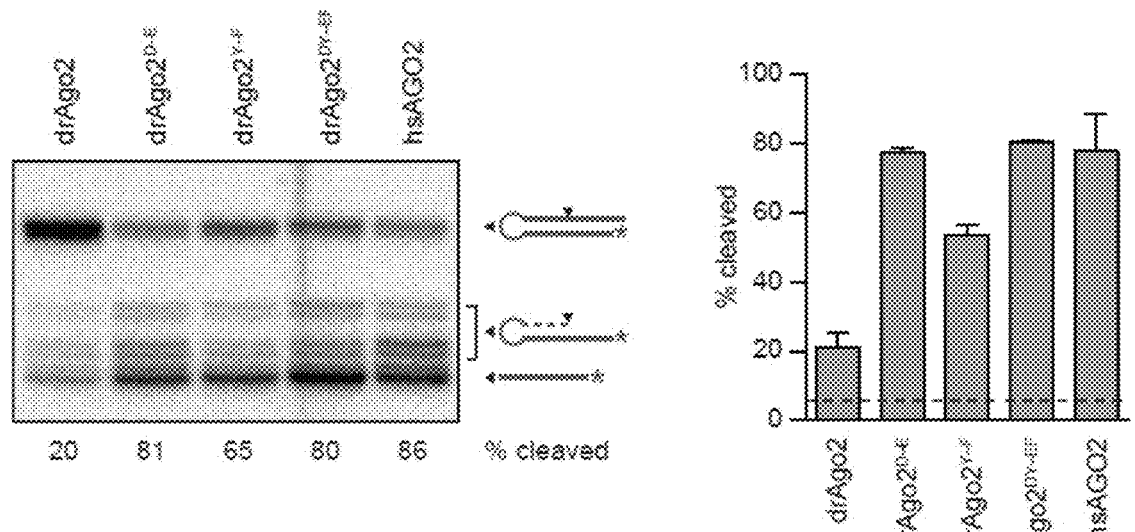

The >100-fold difference between the miR-430-guided slicing activities of hsAGO2 and drAgo2 (FIG. 5, FIG. 6) seemed much greater than the difference between their respective pre-miR-451 cleavage activities (FIG. 7B, FIG. 7C). Although we could not rule out the possibility that the smaller apparent difference for pre-miR-451 cleavage might be attributable to differences in the in vivo assays (as would be the case, if for instance the results for the more efficient constructs were beyond the dynamic range of the pre-miR-451 cleavage assay), we explored the more interesting possibility that the smaller apparent difference for pre-miR-451 cleavage might be attributable to differences between the two substrates of the two types of reactions. Apart from the loop in pre-miR-451, the most prominent structural difference between the two substrates was at miRNA position 6, which was perfectly paired in the slicing substrate but formed a G-G mismatch in the zebrafish pre-miR-451 hairpin.

Figure 13:
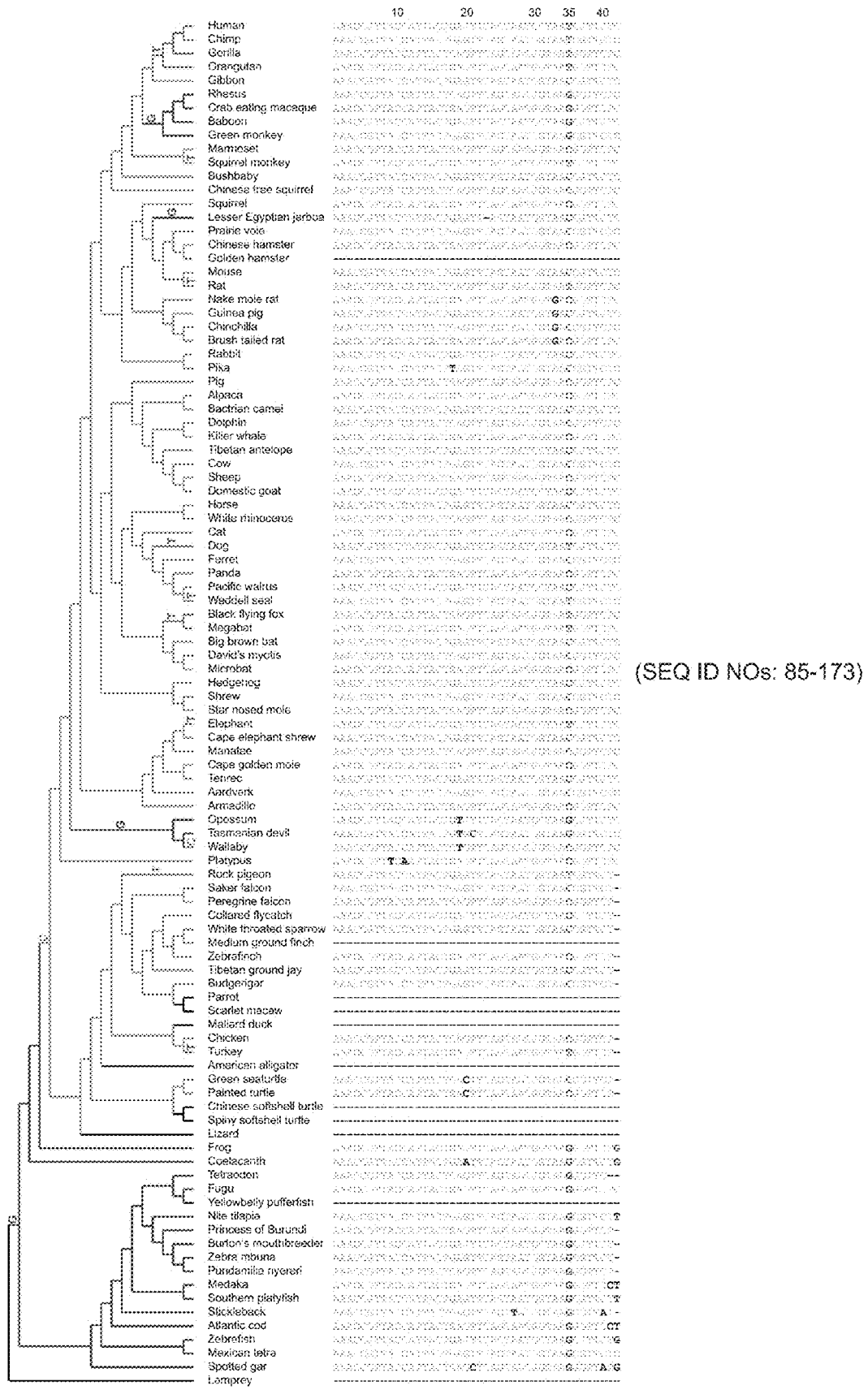
FIG. 13 depicts position 35 of pre-miR-451 is highly variable in amniotes but not fish. Shown is a cladogram (left) and sequence alignment (right) of pre-miR-451 DNA sequences from species in the whole-genome alignment (Tyner et al., 2017). Variable residues are in bold. The nucleotide identity at position 35 is colored (G, blue; C, grey; T, green; not sequenced or not aligned, dashes in alignment and gray in cladogram), with the most parsimonious timing and inheritance of substitutions at this position indicated in the cladogram. The ancestral G-G mismatch at positions 6 and 35 is present throughout the fish species, whereas in the amniotes of the whole-genome alignment, the identity of position 35 is variable, with inference of at least 14 events that changed position 35 to C or T, or back to G, as annotated in the cladogram.

Examination of the whole-genome alignments (Tyner et al., 2017) revealed that the G-G mismatch within pre-miR-451 has been conserved among the fish and amphibian species. However, G35 mutated to a C in an amniote ancestor that gave rise to reptiles, birds, and mammals (FIG. 13), thereby changing the ancestral G-G mismatch to a Watson-Crick match (FIG. 7D), as occurs in our slicing substrate. Although C35 has been retained within most amniote lineages, it mutated again in some linages, most often to the U transition (at least nine times) but sometimes transverting back to a G (at least 3 times) (FIG. 13). For example, all three possibilities were observed within primates, with humans and most other apes acquiring the U, gibbons retaining the C, and old-world monkeys reverting back to the G. Structure-function studies of human pre-miR-451 show that changing U35 to either a G or an A slightly enhances miR-451 activity in HeLa cells (Yang et al., 2012). This increased activity corresponds to increased miR-451 accumulation, which is attributable to more efficient resection of cleaved pre-miR-451 (Yang et al., 2012). These experiments comparing the human G-U wobble to the G-G and G-A mismatches at positions 6 and 35, respectively, establish an interesting tolerance for mismatches at this position, raising the question of how the G-C Watson-Crick match, which is found in most amniotes but untested in previous studies, might compare with the ancestral G-G mismatch.

Figure 7E:
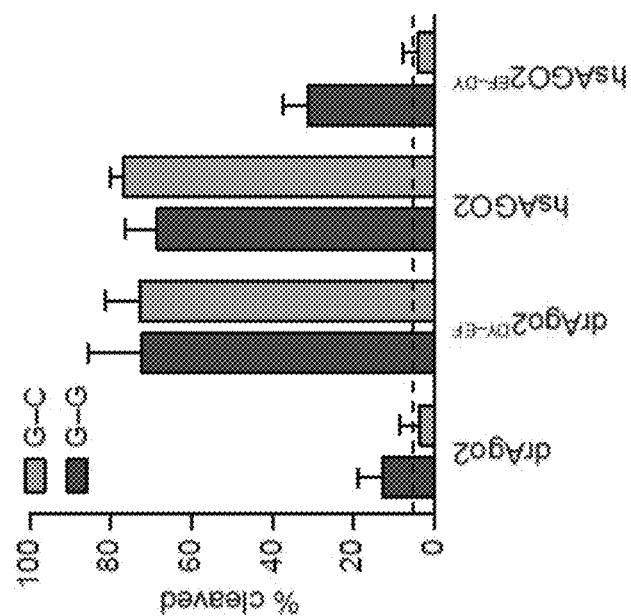
Figure 7E:
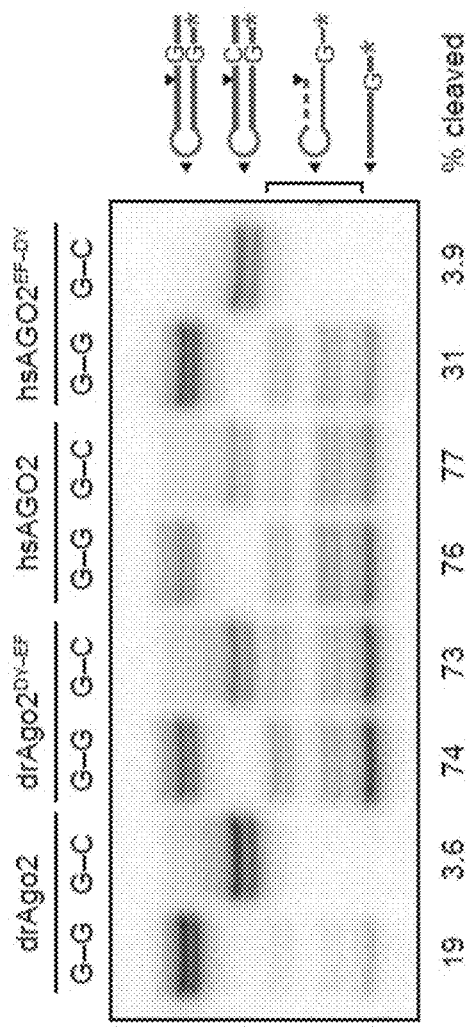

To answer this question, we tested ancestral and amniote pre-miR-451 structures in our assay for pre-miR-451 binding and cleavage and found that drAgo2 had a surprising preference for the ancestral G-G mismatch structure (FIG. 7E). Indeed, although drAgo2 could bind the G-C structure, cleavage did not exceed the background level observed for the D-to-A active-site mutants (FIG. 7B, FIG. 7E). Similar results were observed for the hsAGO2 with the zebrafish substitutions, hsAGO2$^{EF-DY}$ (FIG. 7E). Thus, for these slicing-impaired enzymes possessing the teleost E-to-D and F-to-Y substitutions, the benefit of the G-G mismatch appeared binary—either activity with the G-G mismatch or merely background activity with the G-C match. In contrast, for both repaired drAgo2 (drAgo2$^{DY-EF}$) and wild-type hsAGO2, no benefit of the mismatch was observed, perhaps reflecting a limited dynamic range of this assay (FIG. 7E).

We speculate that the only remaining role for Ago2 catalytic activity in teleost fish is to produce miR-451. Moreover, the reason that their catalytically impaired Ago2 has been able to play this role is the presence of an ancestral G-G mismatch within pre-miR-451, which compensates for the impaired cleavage activity, allowing these fish to produce enough miR-451 to avoid erythropoiesis defects.

A G-G Mismatch at Position 6 Enhances Slicing of Bound Target

Figure 8:
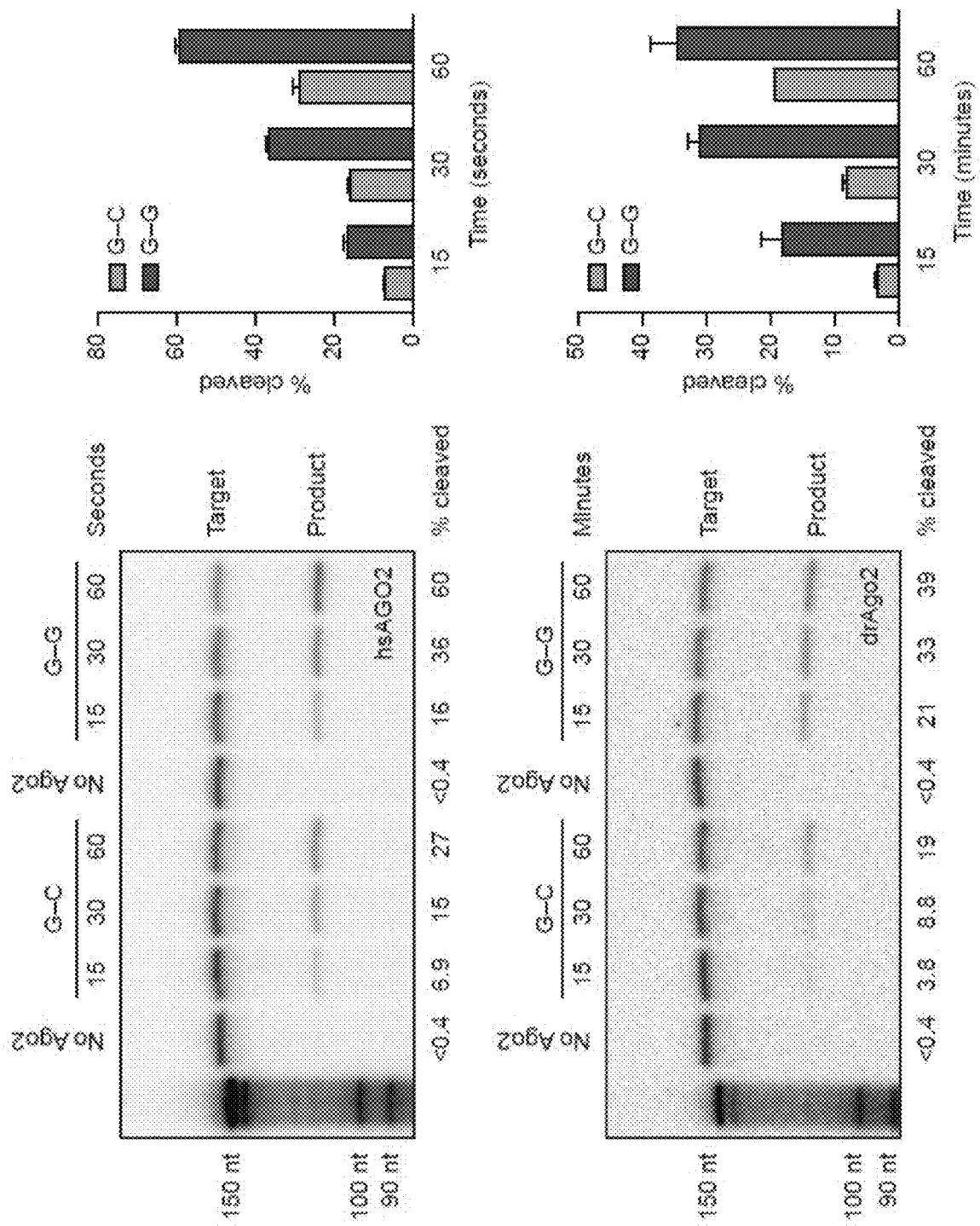
FIG. 8 depicts effects of the G-G mismatch on slicing of bound target. Shown are effects of position-6 G-G mismatch on target slicing by programed hsAGO2 (top) or programed drAgo2 (bottom) in vitro. Assays were as in FIG. 2E, using Ago2 (0.5 nM) in excess over substrate (0.05 nM). The graph plots the mean percent cleavage from two experiments (error bars, range).

Intrigued by the strong benefit of the G-G mismatch for drAgo2-mediated pre-miR-451 cleavage, we tested whether an analogous mismatch might also enhance target slicing in the in vitro assay. To focus first on the slicing step, rather than substrate binding or product release, we started with single-turnover reactions, in which miR-430-programed Ago2 was in 10-fold excess over the slicing substrate and in large excess over the expected $K_D$'s (FIG. 8). Based on the percent reacted at early time points, hsAGO2 sliced the G-G substrate 2.3-fold more rapidly than it sliced the G-C substrate, whereas drAgo2 sliced the G-G substrate 5.5-fold more rapidly.

Figure 9A:
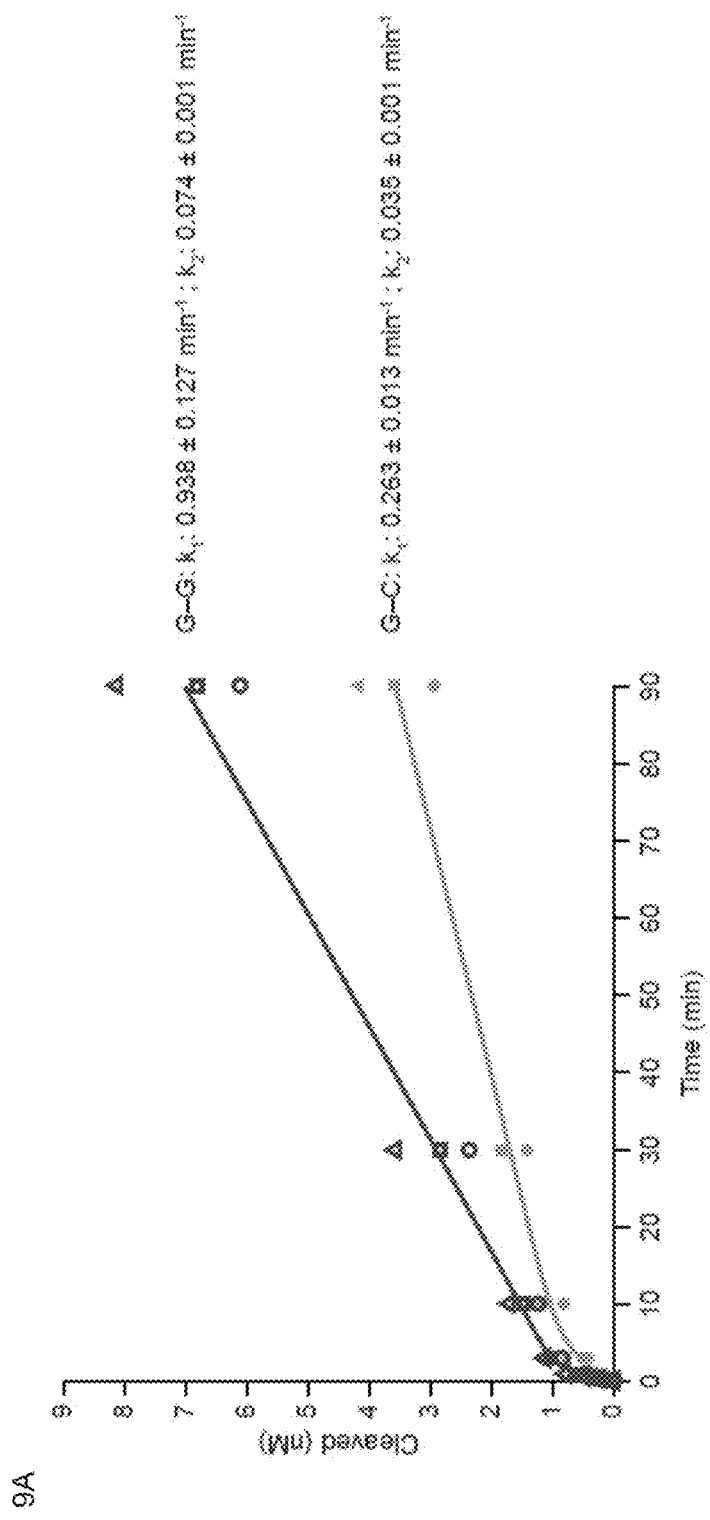
FIGS. 9A-9D depict effects of the G-G mismatch on target association, slicing and product release.
Figure 14A:
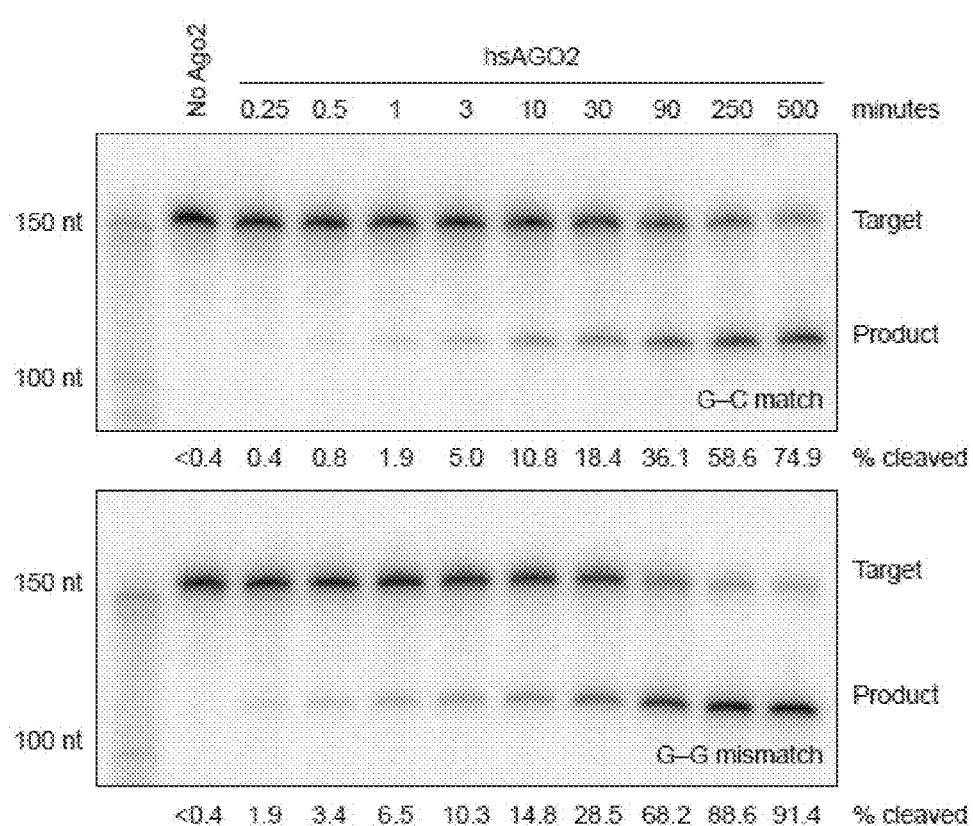
FIGS. 14A-14B depict effects of the G-G mismatch on burst and steady state kinetics.
Figure 14B:
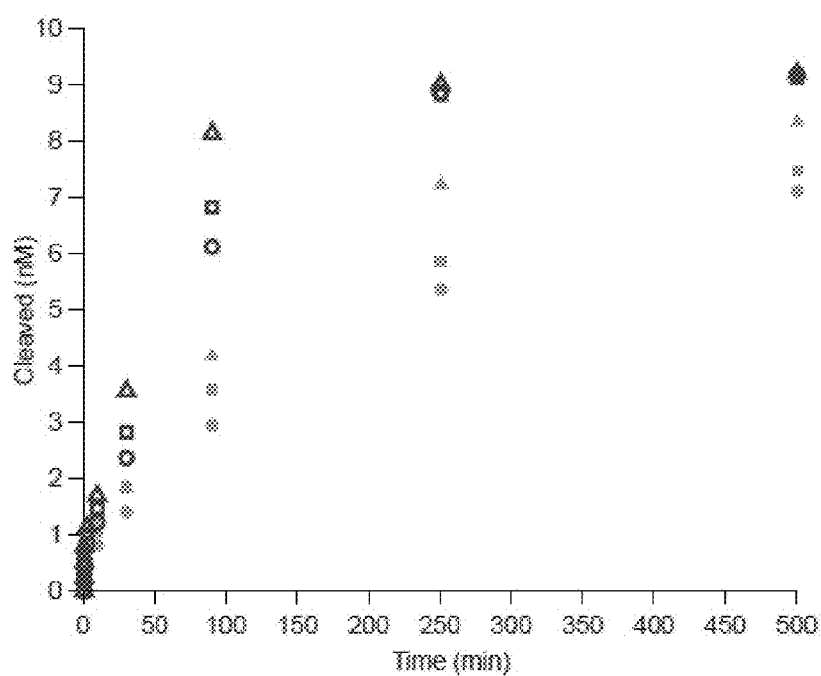

Previous analyses of slicing kinetics show that mismatches to the guide RNA promote product release, thereby enhancing the rate of multiple-turnover slicing of substrates for which release of the fully matched product is rate limiting (Wee et al., 2012). To investigate whether the G-G mismatch to miR-430 might confer this additional, post-slicing rate enhancement, we examined its effect on multiple-turnover slicing, choosing hsAGO2 over drAgo2 for this analysis, as hsAGO2 was deemed more prone to encounter rate-limiting product release by virtue of its more rapid slicing. Indeed, as expected for rate-limiting product release, accumulation of product was biphasic, with an initial burst of rapid slicing ($k_1$) that proceeded until the product concentration approached the enzyme concentration (FIG. 9A, FIG. 14). For the G-G substrate, the rate for the second, slower phase ($k_2$) was 2.1-fold faster than that for the G-C substrate ($k_2$=0.074±0.001 and 0.035±0.001 $min^{-1}$, respectively), consistent with the idea that following miR-430-guided slicing, dissociation of the 3' cleavage product (which differed for the two substrates) was at least partially rate limiting, and the G-G mismatch enhanced this dissociation rate.

As expected, the initial burst for the G-G substrate was also faster than that for the G-C substrate (FIG. 5A, $k_1$=0.938±0.127 and 0.263±0.013 $min^{-1}$, respectively). Indeed, this 3.6-fold enhancement attributed to the G-G mismatch during the initial burst was somewhat greater than the 2.3-fold enhancement attributed to the G-G mismatch during the hsAGO2-catalyzed single-turnover reaction (FIG. 8). This difference in the magnitude of the apparent rate enhancements was presumably a consequence of 1) the somewhat slower association rate expected for a slicing substrate with a mismatch to miRNA position 6 (Salomon et al., 2015), 2) the short time points, which were within a range expected to allow this difference in association rates to perceptively influence product accumulation (Salomon et al., 2015), and 3) the concentration dependence of the association rates, which were governed by substrate concentration (5 nM) in the multiple-turnover reaction and by hsAGO2 concentration (1 nM) in the single-turnover reaction. Because of this concentration dependence, the limiting component (hsAGO2 in the multiple-turnover reaction and the slicing substrate in single-turnover reaction) reached binding saturation less rapidly in the single-turnover reactions, thereby increasing the influence of the different association rates in this format. Thus, in the single-turnover reactions, the slower association rate of the G-G mismatched substrate was expected to more substantially offset the faster slicing of this substrate. By this reasoning, the 3.6-fold enhancement observed in the first phase of the multiple-turnover reaction with hsAGO2 and the 5.5-fold enhancement observed in the single-turnover reaction with drAgo2 best represent the degree to which the G-G mismatch confers enhanced slicing of bound substrate.

Figure 9B:
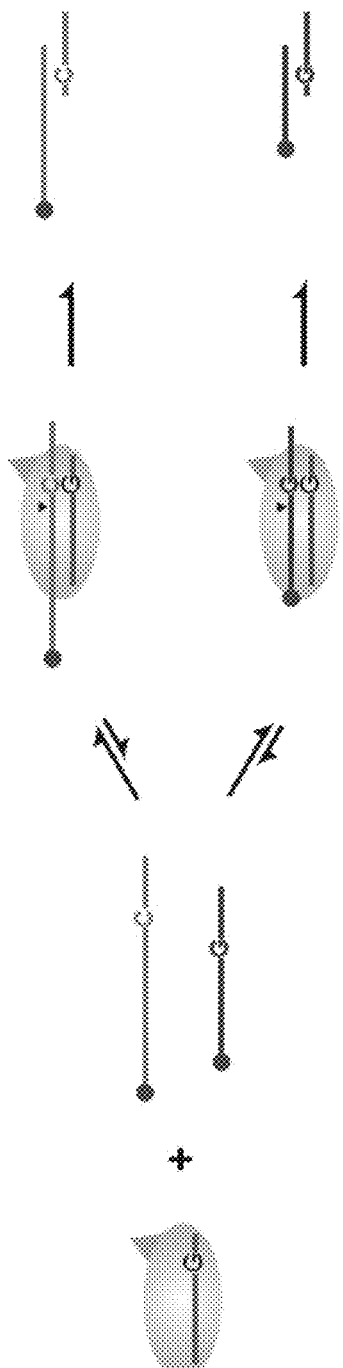
Figure 9C:
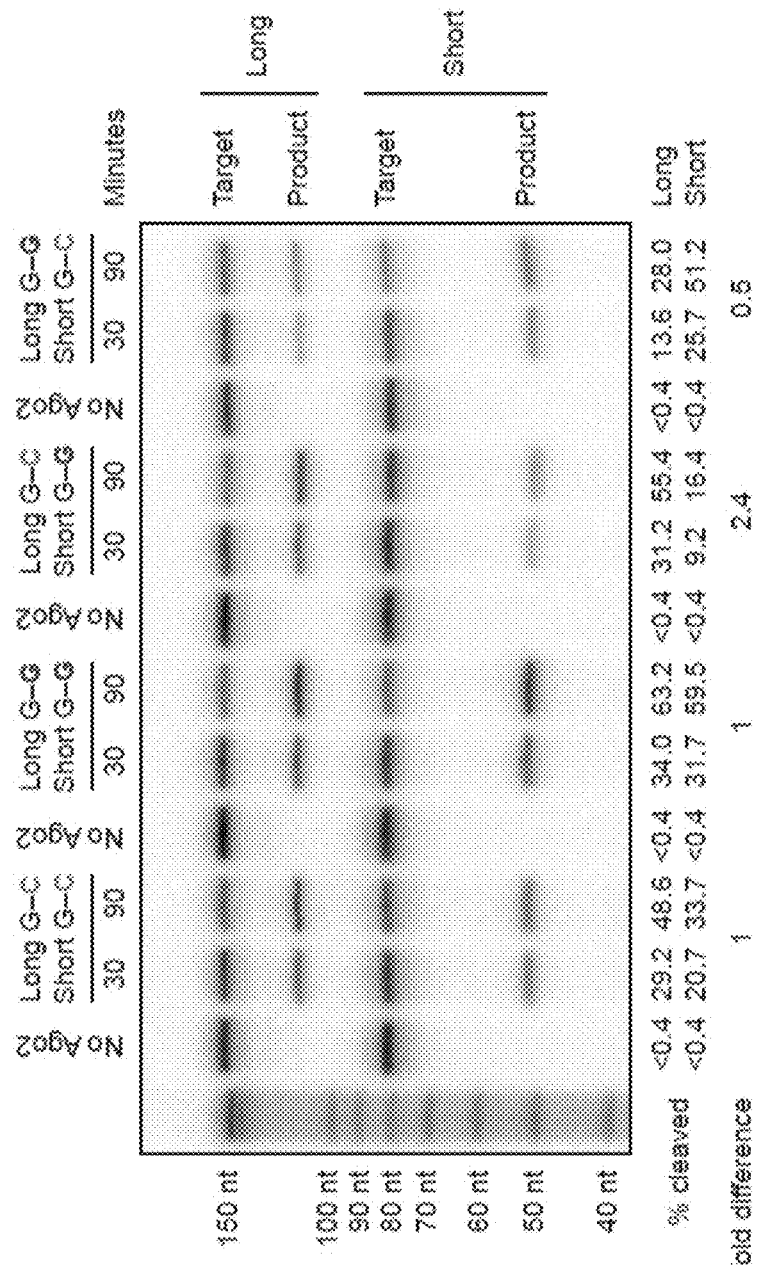
Figure 9D:
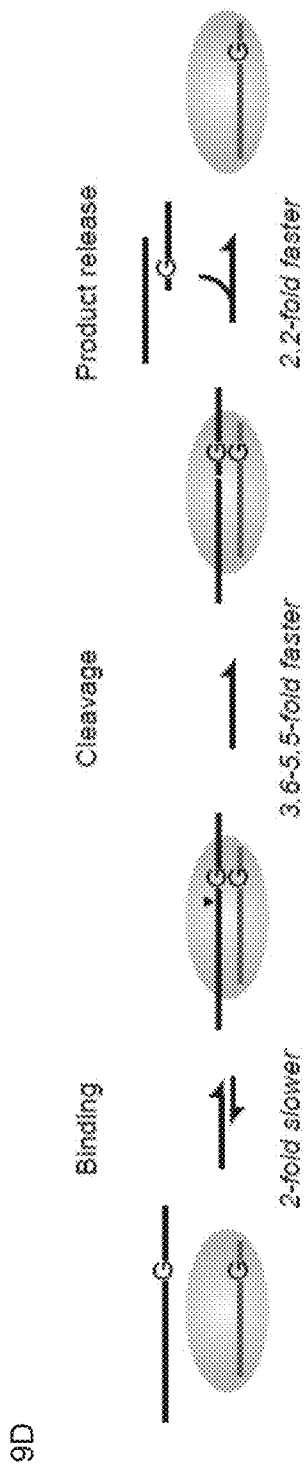

Our results showed that a G-G mismatch at miRNA position 6 imparted a benefit during both pre-miR-451 cleavage (FIG. 7E) and slicing of a bound substrate (FIG. 8, FIG. 9A) but also appeared to slow the association of slicing substrate. To measure this detrimental effect of this G-G mismatch on substrate association, we developed a competitive-cleavage assay, in which a long (168-nt) and short (80-nt) cap-labeled slicing substrate—one with a perfectly paired site, the other with a G-G-mismatched site—were incubated with limiting miR-430-loaded Ago2 (FIG. 9B). As controls, short and long substrates with the same sites were tested, and these controls revealed a slight preference for the longer version of each substrate and reiterated the observation of somewhat faster slicing of G-G substrates in the second phase of miR-430-guided multiple-turnover slicing (FIG. 9C, left half of gel). In the experimental lanes, in which the two site types competed with each other for limiting programed hsAGO2, the G-C site was bound and sliced 2.4-fold more efficiently when it resided in the longer substrate and 1.9-fold more efficiently when it resided in the shorter substrate, indicating a 2.2-fold overall preference for the G-C site over the G-G site (FIG. 9C, right half of gel). Because slicing is much faster than substrate release (Wee et al., 2012), and because the first time point provided ample time for slicing (30 minutes for reactions proceeding at >0.2 $min^{-1}$), most of the molecules that bound to programed hsAGO2 were also sliced, and thus the observed 2.2-fold preference for slicing of the G-C site in this competitive assay was primarily attributable to more rapid association of the G-C site compared to the G-G site.

Discussion

Our discovery that zebrafish lacks efficient slicing demonstrates that a vertebrate species can persist in the wild despite lacking effective RNAi, a powerful gene-silencing pathway that many other eukaryotic species deploy to silence viruses and transposons (Tomari and Zamore, 2005; Malone and Hannon, 2009). Indeed, the two point substitutions that confer this loss of effective RNAi appear to have occurred 300,000,000 years ago in a common ancestor of the sequenced teleost fish. Because this lineage includes most of the extant fish species—and indeed, most of the vertebrate species currently inhabiting the planet, our results imply that this vertebrate lineage that has lost effective RNAi has not only persisted, but it has thrived.

Perhaps the possession of alternative pathways to combat viruses and transposons allowed the RNAi pathway to be lost without consequence. Alternatively, the cost of losing the pathway in teleosts might have been offset by a benefit. This type of cost-benefit tradeoff explains why the presence of RNAi is so variable among fungi: Losing RNAi imparts a cost of decreased protection against transposons but also imparts a benefit, in that it enables acquisition and retention of Killer, a dsRNA element that encodes a toxin that kills neighboring cells that lack Killer (Drinnenberg et al., 2009; Drinnenberg et al., 2011). For fish, we can only speculate on the potential benefits of losing efficient slicing. One possibility is that it would confer resistance to polyoma viruses or other DNA viruses that produce miRNAs that direct slicing of complementary mRNAs transcribed from the opposite viral strand (Grundhoff and Sullivan, 2011).

Whether losing RNAi was essentially neutral or conferred a net benefit to the teleost lineage, the lack of efficient RNAi is clearly not a benefit for the use of zebrafish as a model organism to study the molecular basis of vertebrate development and physiology. Our identification of the two point substitutions that conferred the loss of efficient slicing in teleosts suggests how, with the use of modern gene-editing methods, this activity might be restored to zebrafish. The generation of a zebrafish line that possess efficient slicing activity might not only enable RNAi-based gene-knockdown tools in this model organism but would also reveal the consequences of regaining efficient slicing in a lineage that has not experienced it in 0.3 billion years.

The cost of losing efficient Ago2 catalytic activity was attenuated in teleosts because they retained the G-G mismatch within pre-miR-451, the precursor of a miRNA required for erythrocyte development. We found that this G-G mismatch to position 6 of the miRNA enabled drAgo2-mediated pre-miR-451 cleavage; without the mismatch, pre-miR-451 cleavage was essentially abolished. Despite this enhancement, maturation of the G-G mismatched pre-miR-451 within drAgo2 was not as rapid as that observed within hsAGO2, although it did appear to be sufficient for adequate miR-451 to be produced within the timeframe of erythropoiesis. The unanticipated advantage of this mismatch to a seed nucleotide was also observed during Ago2-catalyzed slicing of bound target transcripts, which occurred 3.6- to 5.5-fold more rapidly for bound substrates containing the mismatch compared to those that were perfectly matched.

Many lines of evidence point to the strict preference for perfect Watson-Crick pairing to the miRNA seed during target binding (Bartel, 2009), and with no evidence to the contrary, this seed pairing, together with pairing to the midsection of the guide RNA, has been assumed to be also preferred for slicing of bound target. Our results reveal that in fact there is a tradeoff between the preferences for binding and those of the subsequent conformational and chemical steps required for slicing. Moreover, for miR-430-directed slicing, the post-chemistry advantage of the G-G mismatch, with its 2.1-fold more favorable product release, essentially negated the ~2-fold disadvantage that this mismatch imparted on target association.

siRNAs and artificial miRNAs are important research tools for gene-knockdown studies, and siRNAs are showing promise in the clinic (Bobbin and Rossi, 2016). In the current design of these gene-knockdown tools, pairing to the last few nucleotides of the guide is considered unimportant (Elbashir et al., 2001b), as is pairing to the first nucleotide of the guide, which is bound to Ago2 in a configuration that prevents pairing to the mRNA (Frank et al., 2010). However, the remainder of the guide is typically designed to pair perfectly to the target mRNA. Knowledge that mismatches between the guide and target can enhance product dissociation rates and thereby potentially increase the multiple-turnover rate of slicing (Wee et al., 2012) is not typically exploited to improve these reagents, presumably out of concern that the benefits to multiple turnover would be offset by less efficient target binding and slicing. Our results revealing the tradeoff between binding and slicing preferences suggest that, depending on the relative importance of target association, target slicing, and product release, a G-G mismatch at position 6 might impart an overall benefit. This strategy for enhancing slicing and product release might be particularly useful for improving siRNAs with nucleotide modifications that protect them from nucleases, as these modifications often also enhance pairing stability, which could shift the balance with respect to the relative importance of target association, predicted to become less of a concern, and product release, predicted to become more of a concern.

The discovery that a G-G mismatch at position 6 of the guide enhances both pre-miR-451 cleavage and target slicing raises the question of whether other mismatches or wobbles at this or other seed positions might also enhance these activities. The perturbed geometry or increased flexibility imparted by this mismatch presumably favors either the transition-state geometry of the active site or an on-pathway pre-chemistry conformational change. Now that the unanticipated benefits of this mismatch and the tradeoff between the pairing preferences for binding and slicing are known, systematic biochemical and biophysical studies can be designed to take aim at these questions.

EXPERIMENTAL PROCEDURES

Plasmids

All plasmids generated for this study (Table S1) are available at Addgene with maps and sequences. To construct Ago2 plasmids, the coding sequence of human or zebrafish Ago2 was inserted into the pCS2+ vector (RZPD). The sequence encoding the 3×-FLAG tag was then added downstream of the start codon by PCR-mediated insertion to generate pCS2+-FLAG3-hsAgo2 and pCS2+-FLAG3-drAgo2. To construct domain-swap plasmids, both the coding sequence of the N domain as well as the remaining domains of human or zebrafish Ago2 were separately amplified by PCR and then spliced together by overlap extension PCR (Table S2). Point substitutions were introduced by PCR-based mutagenesis using QuikChange Lightning Multi Site-Directed Mutagenesis (Agilent) to generate plasmids encoding FLAG-tagged mutant Ago2 proteins. To construct plasmids used to generate the injected miR-430 target RNAs, the coding sequence of Zeocin was inserted into the pCS2+ vector. A single miR-430 site (perfect, 10-11 mismatch, or G-G mismatch) was inserted downstream of the Zeocin sequence using QuikChange Lightning Multi Site-Directed Mutagenesis. To construct plasmids used to generate purified programed Ago2 complexes, the coding sequence of human or zebrafish Ago2 was inserted into the pcDNA3 vector (Invitrogen) and then the 3×-FLAG tag and point substitutions were introduced as described above.

In Vivo Slicing Assay

Ago2 mRNAs and target RNAs were transcribed in vitro using mMESSAGE mMACHINE SP6 according to the manufacturer's instructions (Ambion). The transcribed RNA was purified with RNeasy Mini (QIAGEN) according to the manufacturer's instructions, ethanol precipitated, and stored in water at −80° C. One-cell embryos were injected with target RNA containing one miR-430 site (10 pg/embryo) with or without additional Ago2 mRNA (100 pg/embryo) in a volume of 1 nL (PLI-100 Plus Pico-Injector, Harvard Apparatus). For each condition, 50 embryos were injected. Embryos that developed to the sphere stage (which was approximately 4 hpf and when endogenous miR-430 peaks) were manually de-chorionated, pooled by condition, and placed in 1 mL TRI Reagent (Sigma) for RNA isolation. Isolated RNA was chloroform extracted, ethanol precipitated, and stored at −80° C. prior to analysis on small-RNA blots.

Small-RNA Blot

Total RNA (2 µg) from each condition was denatured and resolved on a 5% urea-polyacrylamide gel. RNA was then electroblotted onto a Amersham Hybon-NX nylon membrane (GE Healthcare Life Sciences) and UV cross-linked at 254 nm. Membranes were pre-incubated with ULTRAhyb Ultrasensitive Hybridization Buffer (Ambion) at 68° C. under rotation for 1 hour and then hybridized under the same conditions overnight with a body-labeled RNA probe complementary to the 5' cleavage product. This RNA probe was transcribed in vitro using MAXIscript T7 RNA polymerase according to the manufacturer's instructions (Invitrogen), replacing the UTP with [α-32P]UTP (PerkinElmer), and desalted with Micro Bio-Spin P-30 Gel Columns (Bio-Rad). Radiolabeled RNA was purified on a 4% urea-polyacrylamide gel, eluted from gel slices in 0.3 M NaCl overnight at 4° C., and ethanol precipitated prior to incubation with the membrane. Membranes were then washed twice with low-stringency buffer (2% 20×SSC and 0.1% SDS) for 5 minutes under rotation at 68° C., and once with high-stringency buffer (0.1% 20×SSC and 0.1% SDS) for 30 minutes under rotation at 68° C. The blots were then exposed to a phosphorimaging screen for 1-14 days. Signal was detected using the Typhoon FLA 7000 phosphorimager (GE Healthcare Life Sciences) and analyzed using the MultiGauge software (FujiFilm).

miR-430 Duplex

Synthetic RNA oligonucleotides (IDT) representing the miR-430b duplex (Table S2) were purified on a 15% urea-polyacrylamide gel and incubated in 2× Annealing buffer (60 mM Tris-HCl pH 7.5, 200 mM NaCl, 2 mM EDTA) at 90° C. for 2 minutes and then slow cooled to room temperature over >3 hours. Annealed RNA was separated from ssRNAs on a native 15% polyacrylamide gel, and duplex was eluted from gel slices in 0.3 M NaCl overnight at 4° C., ethanol precipitated, and stored in 1× Annealing buffer at −80° C.

miR-430-Programmed Ago2

HEK293T cells were cultured in DMEM (Corning) supplemented with 10% heat-inactivated fetal bovine serum at 37° C. with 5% CO2 and split every second or third day at approximately 90% confluency. Cells grown in 150 mm plates were co-transfected with pcDNA3-FLAG3-Ago2 and pMAX-GFP (control) using Lipofectamine 2000 (Invitrogen) at approximately 50% confluency, according to the manufacturer's instructions. At 24 hours post-transfection, cells were transferred to 254 mm square plates and allowed to grow for another 48 hours. Cells were harvested, and S100 extracts were prepared as described (Wee et al., 2012), except that the cells were lysed with a 23G needle and syringe. miR-430 duplex was incubated in 1 ml extract at a final concentration of 50 nM for 2 hours at 25° C., and then programmed Ago2 was affinity purified using a protocol modified from that of Flores-Jasso et al. (2013). Assembled Ago2-RISC was captured with a 3' biotinylated 2'-O-methyl-modified oligonucleotide that paired with nucleotides 2-8 of miR-430 (Table S2) and displaced with a competitor DNA oligonucleotide (Table S2) as described (Wee et al., 2012; Flores-Jasso et al., 2013), except the complex was displaced from the capture oligonucleotide in two successive rounds, each with 100 µL of elution solution (10 µM competitor oligo in 18 mM HEPES pH 7.4, 1 mM potassium acetate, 3 mM magnesium acetate, 0.01% NP-40, 0.2 mg/mL BSA, 0.01 mg/mL yeast tRNA) for 2 hours. To remove complex that had formed with endogenous Agos from the extract, the complex with the ectopically expressed Ago2 was immunopurified based on affinity to the FLAG tag. Anti-FLAG M2 Magnetic Beads (Sigma) were equilibrated with binding buffer (18 mM HEPES pH 7.4, 100 mM potassium acetate, 1 mM magnesium acetate, 0.01 mg/mL yeast tRNA, 0.01% NP-40, 0.2 mg/mL BSA) and incubated with the pooled elution fractions for 2 hours, shaking at 1100 rpm on a ThermoMixer (Eppendorf) at 25° C. The beads were washed with binding buffer three times and eluted with FLAG peptide in binding buffer. The eluted protein in storage buffer [binding buffer supplemented with glycerol and DTT (13% and 1 mM final concentrations, respectively), which diluted the binding buffer by 25%] was flash frozen in liquid nitrogen and stored at −80° C. To measure the binding capacity of the complex and thereby determine its concentration, complex was incubated with excess radiolabeled target RNA that contained a phosphorothioate linkage flanked by 2'-O-methyl-ribose at positions 10 and 11 to block cleavage (Table S2) and layered nitrocellulose-nylon filter-binding assays were performed to quantitate bound and unbound RNA (REF).

RNA Targets for In Vitro Slicing Assays

Targets for in vitro slicing assays were transcribed in vitro with T7 RNA polymerase, treated with TURBO DNase (Ambion) and purified on a urea-polyacrylamide gel. Purified RNA was capped in two batches to generate RNA with high and low specific activity, using the Vaccinia Capping System (New England BioLabs) according to the manufacturer's directions. RNA of high specific activity was prepared by incubating 10 picomol RNA with only [α-32P]GTP for 2 hours in a 10 µl reaction, before adding 0.5 nanomol GTP for another hour, and RNA of low specific activity was prepared by using a 140:1 molar ratio of GTP:[α-32P]GTP. Capped RNA was gel purified, phenol-cholorform and chloroform extracted, ethanol precipitated, resuspended in water, quantified by UV absorbance (NanoDrop) and stored at −80° C.

In Vitro Slicing Assay

Slicing assays are performed in the 37° C. warm room. Pre-mixed, cap-labeled target RNA was pre-incubated in reaction buffer (18 mM HEPES pH 7.4, 100 mM potassium acetate, 1 mM magnesium acetate, 0.01 mg/mL yeast tRNA, 0.01% NP-40, 5 mM DTT) for 15 minutes at 37° C. To initiate the slicing reaction, miR-430-programed Ago2 was added to the RNA-reaction buffer mixture. Reactions were incubated at 37° C., and 2 µL aliquots were removed at each indicated time point and quenched with Gel Loading Buffer II (95% formamide, 18 mM EDTA, 0.025% SDS, 0.025% xylene cyanol, and 0.025% bromophenol blue; Ambion). To monitor slicing, RNAs were resolved on a urea-polyacrylamide gel, and radiolabeled target and product were visualized on the Typhoon FLA 7000 phosphorimager and analyzed using the MultiGauge software. Data in FIG. 5A and Figure S5B were fit in MATLAB to the burst and steady-state equation (Wee et al., 2012), $$F(t) = E \times \frac{a^2}{(a+b)^2}(1 - e^{-(a+b)t}) + E \times \frac{ab}{a+b}t,$$

where F(t) is target cleaved over time, E is the enzyme concentration, and a and b are rate constants according to the following scheme,

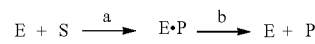

Pre-miR-451 Binding and Cleavage Assay

Synthetic pre-miR-451 RNAs (IDT) (Table S2) were purified on a urea-polyacrylamide gel, phosphorylated with [γ-32P]ATP using T4 polynucleotide kinase (New England BioLabs), desalted with Micro Bio-Spin P-30 Gel Columns (BioRad), and gel purified again. One-cell embryos were co-injected with end-labeled pre-miR-451 (10 pg/embryo) and Ago2 mRNA (100 pg/embryo), injecting 250-300 embryos for each condition (i.e., each lane on the gel). At 4 hpf, injected embryos were manually de-chorionated in the presence of 1 mg/mL pronase (Sigma), washed 3 times with E3 (5 mM NaCl, 0.17 mM KCl, 0.33 mM CaCl2, and 0.33 mM MgSO4), and transferred to a 0.6 mL Eppendorf tube. To break the yolk sak, embryos were gently pipetted with 400 µL of de-yolking buffer [55 mM NaCl, 1.8 mM KCl, 1.25 mM NaHCO$_3$, protease inhibitor cocktail tablet (cOmplete, mini, EDTA-free, Sigma; one tablet per 10 mL buffer)]. The embryos were then shaken at 1100 rpm on a Thermo-Mixer for 5 minutes and centrifuged at 300 g for 1 minute to separate the yolk from the cells. The yolk-containing supernatant was removed, and this de-yolking process was repeated 3 times. Embryo lysis buffer (25 mM Tris pH 7.5, 2 mM EDTA, 150 mM NaCl, 10% glycerol, 1% Triton X-100) was then added and vortexed with 0.5 mm glass beads (BioSpec) for 5 seconds every 30 seconds for 4 minutes at 4° C. The 0.6 mL Eppendorf tube was punctured at its bottom with a 26G gauge needle and placed inside a 1.5 mL Eppendorf tube. The lysate was separated from the glass beads and clarified by centrifugation at 21,130 g for 10 minutes at 4° C. Clarified lysates were flash frozen in liquid nitrogen and stored at −80° C. prior to FLAG immunoprecipitation. To immunoprecipitate FLAG-tagged Ago2, the lysate was incubated with Anti-FLAG M2 Magnetic Beads (Sigma) under rotation at 4° C. overnight in binding buffer (25 mM Tris pH 7.5, 2 mM EDTA, 150 mM NaCl, 10% glycerol, 1% Triton X-100). The lysate was removed, and the beads were washed three times with wash buffer (25 mM Tris pH 7.5, 2 mM EDTA, 1 M NaCl, 10% glycerol, 1% Triton X-100) for 10 minutes each, under rotation, at 4° C. 1 mL TRI Reagent (Sigma) was added directly to the beads to extract total RNA from the immunoprecipitated material. After chloroform extraction and ethanol precipitation, extracted RNA was resolved on urea-polyacrylamide gels, visualized on the Typhoon FLA 7000 phosphorimager, and analyzed using the MultiGauge software.

TABLE S1

| Description |
| --- |
| Zebrafish expression plasmid, eGFP |
| Zebrafish expression plasmid, *D. rerio* Ago2 |
| Zebrafish expression plasmid, 3X-FLAG-tagged *D. rerio* Ago2 |
| Zebrafish expression plasmid, 3X-FLAG-tagged *D. rerio* Ago2 (D683A) |
| Zebrafish expression plasmid, 3X-FLAG-tagged *D. rerio* Ago2 (D651E) |
| Zebrafish expression plasmid, 3X-FLAG-tagged *D. rerio* Ago2 (Y680F) |
| Zebrafish expression plasmid, 3X-FLAG-tagged *D. rerio* Ago2 (D651E, F680Y) |
| Zebrafish expression plasmid, 3X-FLAG-tagged *H. Sapiens* Ago2 (1-175), *D. rerio* Ago2 (190-873) |
| Zebrafish expression plasmid, *H. Sapiens* Ago2 |
| Zebrafish expression plasmid, 3X-FLAG-tagged *H. Sapiens* Ago2 |
| Zebrafish expression plasmid, 3X-FLAG-tagged *H. Sapiens* Ago2 (D669A) |
| Zebrafish expression plasmid, 3X-FLAG-tagged *H. Sapiens* Ago2 (E637D) |
| Zebrafish expression plasmid, 3X-FLAG-tagged *H. Sapiens* Ago2 (F666Y) |
| Zebrafish expression plasmid, 3X-FLAG-tagged *H. Sapiens* Ago2 (E637D, F666Y) |
| Zebrafish expression plasmid, 3X-FLAG-tagged *D. rerio* Ago2 (1-189), *H. Sapiens* Ago2 (176-859) |
| Zebrafish expression plasmid, Zeocin |
| Zebrafish expression plasmid, Zeocin, miR-430 site |
| Zebrafish expression plasmid, Zeocin, miR-430 site with a 10-11 mm |
| Zebrafish expression plasmid, Zeocin, miR-430 site with a G-G mm at position 6 |
| Mammalian expression plasmid, GFP |
| Mammalian expression plasmid, *D. rerio* Ago2 |
| Mammalian expression plasmid, 3X-FLAG-tagged *D. rerio* Ago2 |
| Mammalian expression plasmid, 3X-FLAG-tagged *D. rerio* Ago2 (D651E, F680Y) |
| Mammalian expression plasmid, 3X-FLAG-tagged *D. rerio* Ago2 (D611A) |
| Mammalian expression plasmid, *H. Sapiens* Ago2 |
| Mammalian expression plasmid, 3X-FLAG-tagged *H. Sapiens* Ago2 |
| Zebrafish expression plasmid, GFP |
| Control cloning vector |

TABLE S2

| DNA Name | Sequence |
| --- | --- |
| Chimera N_for | GCTACTTGTTCTTTTTGCAGGATCC (SEQ ID NO: 3) |
| drAgo2 N_rev | CCTCATGGATGGCAAGTGCCTCATGACAACATCCAGAGCC (SEQ ID NO: 4) |
| hsAGO2 N_rev | CCTCATAGAGGGCAAATGTCTCATGACCACGTCCAGGGCC (SEQ ID NO: 5) |
| drAgo2 body_for | TGGACGGCTACCAAACATCC (SEQ ID NO: 6) |
| hsAGO2 body_for | TGCCTAGCGTCCCTTTTGAG (SEQ ID NO: 7) |
| Chimera body_rev | TGGTTTGTCCAAACTCATCAA (SEQ ID NO: 8) |
| drAgo2 D683A_sense | CATCATCTACTACAGAGCCGGCATCTCTGAAGGCC (SEQ ID NO: 9) |

TABLE S2-continued

| Name | Sequence |
|---|---|
| drAgo2 D683A_antisense | GGCCTTCAGAGATGCCGGCTCTGTAGTAGATGATG (SEQ ID NO: 10) |
| drAgo2 D651E_sense | CAGCACCGGCAGGAGATCATTCAGGATCTG (SEQ ID NO: 11) |
| drAgo2 D651E_antisense | CAGATCCTGAATGATCTCCTGCCGGTGCTG (SEQ ID NO: 12) |
| drAgo2 Y680F_sense | CCAACACGCATCATCTTCTACAGAGACGGCATC (SEQ ID NO: 13) |
| drAgo2 Y680F_antisense | GATGCCGTCTCTGTAGAAGATGATGCGTGTTGG (SEQ ID NO: 14) |
| hsAGO2 D669A_sense | TCATCTTCTACCGCGCCGGTGTCTCTGAAGG (SEQ ID NO: 15) |
| hsAGO2 D669A_antisense | CCTTCAGAGACACCGGCGCGGTAGAAGATGA (SEQ ID NO: 16) |
| hsAGO2 E637D_sense | GCAGCACCGGCAGGATATCATACAAGACCTG (SEQ ID NO: 17) |
| hsAGO2 E637D_antisense | CAGGTCTTGTATGATATCCTGCCGGTGCTGC (SEQ ID NO: 18) |
| hsAGO2_F666Y_sense | CCCACCCGCATCATCTATTACCGCGACGGTGT (SEQ ID NO: 19) |
| hsAGO2 F666Y_antisense | ACACCGTCGCGGTAATAGATGATGCGGGTGGG (SEQ ID NO: 20) |
| Zeocin target_miR-430_for | ACTGACTCGAGCCTCTAGAAATAAGCTACCCCAACTT GATAGCACTTTATAAGCTATAGTGAGTCGTATTACG (SEQ ID NO: 21) |
| Zeocin target_miR-430_rev | CGTAATACGACTCACTATAGCTTATAAAGTGCTATCA AGTTGGGGTAGCTTATTTCTAGAGGCTCGAGTCAGT (SEQ ID NO: 22) |
| Zeocin_miR-430_10-11 mm_for | ACTGACTCGAGCCTCTAGAAATAAGCTACCCCAACTT CTTAGCACTTTATAAGCTATAGTGAGTCGTATTACG (SEQ ID NO: 23) |
| Zeocin miR-430_10-11 mm_rev | CGTAATACGACTCACTATAGCTTATAAAGTGCTAAGA AGTTGGGGTAGCTTATTTCTAGAGGCTCGAGTCAGT (SEQ ID NO: 24) |
| Zeocin_miR-430_G-G_for | ACTGACTCGAGCCTCTAGAAATAAGCTACCCCAACTT GATAGGACTTTATAAGCTATAGTGAGTCGTATTACG (SEQ ID NO: 25) |
| Zeocin_miR-430_G-G_rev | CGTAATACGACTCACTATAGCTTATAAAGTCCTATCA AGTTGGGGTAGCTTATTTCTAGAGGCTCGAGTCAGT (SEQ ID NO: 26) |
| Zeocin probe_for | ATTCAGGATCATGGCCAAGTTG (SEQ ID NO: 27) |
| Zeocin probe_rev | TTCTAATACGACTCACTATAGGGAGAAGGAGGTTTCT AGAGGCTCGAGTCAGTC (SEQ ID NO: 28) |
| GFP probe | GTCCAGCTCGACCAGGATGGGCACCACCCCGGTGAA CAGCTCCTCGCCCTTGCTCACCAT (SEQ ID NO: 29) |
| 168-nt target_for | GCGTAATACGACTCACTATAGGGTCACATCTCATCTA CCTCC (SEQ ID NO: 30) |
| 168-nt target_miR-430_perfect_rev | CCCATTTACATCGCGTTGAGTGTAGAACGGTTGTATA AAAGGTAAAGTGCTATCAAGTTGGGGTAGATCCAGA GGAATTCATTATCAGTG (SEQ ID NO: 31) |

TABLE S2-continued

| | |
|---|---|
| 168-nt target_miR-430_10-11 mm_rev | CCCATTTACATCGCGTTGAGTGTAGAACGGTTGTATA AAAGGTAAAGTGCTAAGAAGTTGGGGTAGATCCAGA GGAATTCATTATCAGTG (SEQ ID NO: 32) |
| 168-nt target_miR-430_G-G_rev | CCCATTTACATCGCGTTGAGTGTAGAACGGTTGTATA AAAGGTAAAGTCCTATCAAGTTGGGGTAGATCCAGA GGAATTCATTATCAGTG (SEQ ID NO: 33) |
| 80-nt target_miR-430 | TTGTTGTTGTTGTTGTTGTTAAAGTGCTATCAAGTTGG GGTAGTGTTGTTGTTGTTGTTGTTGTTGTTGTTGTTGC TCCCTATAGTGAGTCGTATTAGAA (SEQ ID NO: 34) |
| 80-nt target_miR-430_G-G | TTGTTGTTGTTGTTGTTGTTAAAGTCCTATCAAGTTGG GGTAGTGTTGTTGTTGTTGTTGTTGTTGTTGTTGTTGC TCCCTATAGTGAGTCGTATTAGAA (SEQ ID NO: 35) |
| miR-430 capture | mUmCmUmUmCmCmUmCmCmGmCmAmCmCmAmCmA mCmAmGmCmAmCmUmUmAmAmCmCmUmUmAmCmA mCmAmC/3Bio/ (SEQ ID NO: 36) |
| miR-430 competitor | AAGGTTAAGTGCTGTGTGGTGCGGAGGAAGA (SEQ ID NO: 37) |

| RNA Name | Sequence |
|---|---|
| miR-430b guide | AAAGUGCUAUCAAGUUGGGGUAG (SEQ ID NO: 38) |
| miR-430b passenger | ACCCUAACUUUAGCAUCUUUCU (SEQ ID NO: 39) |
| pre-miR-451 (ancestral) | AAACCGUUACCAUUACUGAGUUUAGUAAUGGUAAG GGUUCUG (SEQ ID NO: 40) |
| pre-miR-451 (amniote) | AAACCGUUACCAUUACUGAGUUUAGUAAUGGUAAC GGUUCUG (SEQ ID NO: 41) |

REFERENCES

Babiarz, J. E., Ruby, J. G., Wang, Y., Bartel, D. P., and Blelloch, R. (2008). Mouse ES cells express endogenous shRNAs, siRNAs, and other Microprocessor-independent, Dicer-dependent small RNAs. Genes & development 22, 2773-2785.

Bartel, D. P. (2004). MicroRNAs: genomics, biogenesis, mechanism, and function. Cell 116, 281-297.

Bartel, D. P. (2009). MicroRNAs: target recognition and regulatory functions. Cell 136, 215-233.

Bernardi, G., Wiley, E. O., Mansour, H., Miller, M. R., Orti, G., Haussler, D., O'Brien, S. J., Ryder, O. A., and Venkatesh, B. (2012). The fishes of Genome 10K. Mar Genomics 7, 3-6.

Betancur, R. R., Broughton, R. E., Wiley, E. O., Carpenter, K., Lopez, J. A., Li, C., Holcroft, N. I., Arcila, D., Sanciangco, M., Cureton Ii, J. C., et al. (2013). The tree of life and a new classification of bony fishes. PLoS currents 5.

Bobbin, M. L., and Rossi, J. J. (2016). RNA Interference (RNAi)-Based Therapeutics: Delivering on the Promise? Annu Rev Pharmacol Toxicol 56, 103-122.

Broughton, R. E., Betancur, R. R., Li, C., Arratia, G., and Orti, G. (2013). Multi-locus phylogenetic analysis reveals the pattern and tempo of bony fish evolution. PLoS currents 5.

Cheloufi, S., Dos Santos, C. O., Chong, M. M., and Hannon, G. J. (2010). A dicer-independent miRNA biogenesis pathway that requires Ago catalysis. Nature 465, 584-589.

Cifuentes, D., Xue, H., Taylor, D. W., Patnode, H., Mishima, Y., Cheloufi, S., Ma, E., Mane, S., Hannon, G. J., Lawson, N. D., et al. (2010). A novel miRNA processing pathway independent of Dicer requires Argonaute2 catalytic activity. Science 328, 1694-1698.

Davis, E., Caiment, F., Tordoir, X., Cavaille, J., Ferguson-Smith, A., Cockett, N., Georges, M., and Charlier, C. (2005). RNAi-mediated allelic trans-interaction at the imprinted Rtll/Pegll locus. Curr Biol 15, 743-749.

Drinnenberg, I. A., Fink, G. R., and Bartel, D. P. (2011). Compatibility with killer explains the rise of RNAi-deficient fungi. Science 333, 1592.

Drinnenberg, I. A., Weinberg, D. E., Xie, K. T., Mower, J. P., Wolfe, K. H., Fink, G. R., and Bartel, D. P. (2009). RNAi in budding yeast. Science 326, 544-550.

Eichhorn, S. W., Guo, H., McGeary, S. E., Rodriguez-Mias, R. A., Shin, C., Baek, D., Hsu, S. H., Ghoshal, K., Villen, J., and Bartel, D. P. (2014). mRNA destabilization is the dominant effect of mammalian microRNAs by the time substantial repression ensues. Molecular cell 56, 104-115.

Elbashir, S. M., Harborth, J., Lendeckel, W., Yalcin, A., Weber, K., and Tuschl, T. (2001). Duplexes of 21-nucleotide RNAs mediate RNA interference in cultured mammalian cells. Nature 411, 494-498.

Elbashir, S. M., Lendeckel, W., and Tuschl, T. (2001b). RNA interference is mediated by 21- and 22-nucleotide RNAs. Genes Dev 15, 188-200.

Faehnle, C. R., Elkayam, E., Haase, A. D., Hannon, G. J., and Joshua-Tor, L. (2013). The making of a slicer: activation of human Argonaute-1. Cell reports 3, 1901-1909.

Farazi, T. A., Juranek, S. A., and Tuschl, T. (2008). The growing catalog of small RNAs and their association with distinct Argonaute/Piwi family members. Development 135, 1201-1214.

Flemr, M., Malik, R., Franke, V., Nejepinska, J., Sedlacek, R., Vlahovicek, K., and Svoboda, P. (2013). A retrotransposon-driven dicer isoform directs endogenous small interfering RNA production in mouse oocytes. Cell 155, 807-816.

Flores-Jasso, C. F., Salomon, W. E., and Zamore, P. D. (2013). Rapid and specific purification of Argonaute-small RNA complexes from crude cell lysates. Rna 19, 271-279.

Frank, F., Sonenberg, N., and Nagar, B. (2010). Structural basis for 5'-nucleotide base-specific recognition of guide RNA by human AGO2. Nature 465, 818-822.

Friedman, R. C., Farh, K. K., Burge, C. B., and Bartel, D. P. (2009). Most mammalian mRNAs are conserved targets of microRNAs. Genome Res 19, 92-105.

Giraldez, A. J., Cinalli, R. M., Glasner, M. E., Enright, A. J., Thomson, J. M., Baskerville, S., Hammond, S. M., Bartel, D. P., and Schier, A. F. (2005). MicroRNAs regulate brain morphogenesis in zebrafish. Science 308, 833-838.

Gruber, J., Manninga, H., Tuschl, T., Osborn, M., and Weber, K. (2005). Specific RNAi mediated gene knockdown in zebrafish cell lines. RNA Biol 2, 101-105.

Grundhoff, A., and Sullivan, C. S. (2011). Virus-encoded microRNAs. Virology 411, 325-343.

Guo, H., Ingolia, N. T., Weissman, J. S., and Bartel, D. P. (2010). Mammalian microRNAs predominantly act to decrease target mRNA levels. Nature 466, 835-840.

Ha, M., and Kim, V. N. (2014). Regulation of microRNA biogenesis. Nature reviews Molecular cell biology 15, 509-524.

Haley, B., and Zamore, P. D. (2004). Kinetic analysis of the RNAi enzyme complex. Nature structural & molecular biology 11, 599-606.

Hansen, T. B., Wiklund, E. D., Bramsen, J. B., Villadsen, S. B., Statham, A. L., Clark, S. J., and Kjems, J. (2011). miRNA-dependent gene silencing involving Ago2-mediated cleavage of a circular antisense RNA. EMBO J 30, 4414-4422.

Hauptmann, J., Dueck, A., Harlander, S., Pfaff, J., Merkl, R., and Meister, G. (2013). Turning catalytically inactive human Argonaute proteins into active slicer enzymes. Nature structural & molecular biology 20, 814-817.

Hauptmann, J., Kater, L., Loffler, P., Merkl, R., and Meister, G. (2014). Generation of catalytic human Ago4 identifies structural elements important for RNA cleavage. Rna 20, 1532-1538.

Iwasaki, Y. W., Siomi, M. C., and Siomi, H. (2015). PIWI-Interacting RNA: Its Biogenesis and Functions. Annu Rev Biochem 84, 405-433.

Jonas, S., and Izaurralde, E. (2015). Towards a molecular understanding of microRNA-mediated gene silencing. Nature reviews Genetics 16, 421-433.

Kelly, A., and Hurlstone, A. F. (2011). The use of RNAi technologies for gene knockdown in zebrafish. Briefings in functional genomics 10, 189-196.

Kim, V. N. (2005). MicroRNA biogenesis: coordinated cropping and dicing. Nat Rev Mol Cell Biol 6, 376-385.

Liu, J., Carmell, M. A., Rivas, F. V., Marsden, C. G., Thomson, J. M., Song, J. J., Hammond, S. M., Joshua-Tor, L., and Hannon, G. J. (2004). Argonaute2 is the catalytic engine of mammalian RNAi. Science 305, 1437-1441.

Ma, J. B., Yuan, Y. R., Meister, G., Pei, Y., Tuschl, T., and Patel, D. J. (2005). Structural basis for 5'-end-specific recognition of guide RNA by the *A. fulgidus* Piwi protein. Nature 434, 666-670.

Malone, C. D., and Hannon, G. J. (2009). Small RNAs as guardians of the genome. Cell 136, 656-668.

Mangos, S., Vanderbeld, B., Krawetz, R., Sudol, K., and Kelly, G. M. (2001). Ran binding protein RanBP1 in zebrafish embryonic development. Mol Reprod Dev 59, 235-248.

Meister, G., Landthaler, M., Patkaniowska, A., Dorsett, Y., Teng, G., and Tuschl, T. (2004). Human Argonaute2 mediates RNA cleavage targeted by miRNAs and siRNAs. Molecular cell 15, 185-197.

Moazed, D. (2009). Small RNAs in transcriptional gene silencing and genome defence. Nature 457, 413-420.

Nakanishi, K., Ascano, M., Gogakos, T., Ishibe-Murakami, S., Serganov, A. A., Briskin, D., Morozov, P., Tuschl, T., and Patel, D. J. (2013). Eukaryote-specific insertion elements control human ARGONAUTE slicer activity. Cell reports 3, 1893-1900.

Nakanishi, K., Weinberg, D. E., Bartel, D. P., and Patel, D. J. (2012). Structure of yeast Argonaute with guide RNA. Nature 486, 368-374.

Oates, A. C., Bruce, A. E., and Ho, R. K. (2000). Too much interference: injection of double-stranded RNA has non-specific effects in the zebrafish embryo. Dev Biol 224, 20-28.

Olive, V., Minella, A. C., and He, L. (2015). Outside the coding genome, mammalian microRNAs confer structural and functional complexity. Science signaling 8, re2.

Parker, J. S., Roe, S. M., and Barford, D. (2005). Structural insights into mRNA recognition from a PIWI domain-siRNA guide complex. Nature 434, 663-666.

Patrick, D. M., Zhang, C. C., Tao, Y., Yao, H., Qi, X., Schwartz, R. J., Jun-Shen Huang, L., and Olson, E. N. (2010). Defective erythroid differentiation in miR-451 mutant mice mediated by 14-3-3zeta. Genes Dev 24, 1614-1619.

Rasmussen, K. D., Simmini, S., Abreu-Goodger, C., Bartonicek, N., Di Giacomo, M., Bilbao-Cortes, D., Horos, R., Von Lindern, M., Enright, A. J., and O'Carroll, D. (2010). The miR-144/451 locus is required for erythroid homeostasis. The Journal of experimental medicine 207, 1351-1358.

Rozhkov, N. V., Hammell, M., and Hannon, G. J. (2013). Multiple roles for Piwi in silencing Drosophila transposons. Genes & development 27, 400-412.

Salomon, W. E., Jolly, S. M., Moore, M. J., Zamore, P. D., and Serebrov, V. (2015). Single-Molecule Imaging Reveals that Argonaute Reshapes the Binding Properties of Its Nucleic Acid Guides. Cell 162, 84-95.

Schirle, N. T., and MacRae, I. J. (2012). The crystal structure of human Argonaute2. Science 336, 1037-1040.

Shabalina, S. A., and Koonin, E. V. (2008). Origins and evolution of eukaryotic RNA interference. Trends in ecology & evolution 23, 578-587.

Shin, C., Nam, J. W., Farh, K. K., Chiang, H. R., Shkumatava, A., and Bartel, D. P. (2010). Expanding the microRNA targeting code: functional sites with centered pairing. Mol Cell 38, 789-802.

Sienski, G., Donertas, D., and Brennecke, J. (2012). Transcriptional silencing of transposons by Piwi and maelstrom and its impact on chromatin state and gene expression. Cell 151, 964-980.

Song, J. J., Smith, S. K., Hannon, G. J., and Joshua-Tor, L. (2004). Crystal structure of Argonaute and its implications for RISC slicer activity. Science 305, 1434-1437.

Song, R., Hennig, G. W., Wu, Q., Jose, C., Zheng, H., and Yan, W. (2011). Male germ cells express abundant endogenous siRNAs. Proceedings of the National Academy of Sciences of the United States of America 108, 13159-13164.

Stein, P., Rozhkov, N. V., Li, F., Cardenas, F. L., Davydenko, O., Vandivier, L. E., Gregory, B. D., Hannon, G. J., and Schultz, R. M. (2015). Essential Role for endogenous siRNAs during meiosis in mouse oocytes. PLoS genetics 11, e1005013.

Tam, O. H., Aravin, A. A., Stein, P., Girard, A., Murchison, E. P., Cheloufi, S., Hodges, E., Anger, M., Sachidanandam, R., Schultz, R. M., et al. (2008). Pseudogene-derived small interfering RNAs regulate gene expression in mouse oocytes. Nature 453, 534-538.

Tolia, N. H., and Joshua-Tor, L. (2007). Slicer and the argonautes. Nat Chem Biol 3, 36-43.

Tomari, Y., and Zamore, P. D. (2005). Perspective: machines for RNAi. Genes & development 19, 517-529.

Tuschl, T. (2001). RNA interference and small interfering RNAs. Chembiochem 2, 239-245.

Tyner, C., Barber, G. P., Casper, J., Clawson, H., Diekhans, M., Eisenhart, C., Fischer, C. M., Gibson, D., Gonzalez, J. N., Guruvadoo, L., et al. (2017). The UCSC Genome Browser database: 2017 update. Nucleic Acids Res 45, D626-D634.

Vidigal, J. A., and Ventura, A. (2015). The biological functions of miRNAs: lessons from in vivo studies. Trends in cell biology 25, 137-147.

Watanabe, T., Totoki, Y., Toyoda, A., Kaneda, M., Kuramochi-Miyagawa, S., Obata, Y., Chiba, H., Kohara, Y., Kono, T., Nakano, T., et al. (2008). Endogenous siRNAs from naturally formed dsRNAs regulate transcripts in mouse oocytes. Nature 453, 539-543.

Wee, L. M., Flores-Jasso, C. F., Salomon, W. E., and Zamore, P. D. (2012). Argonaute divides its RNA guide into domains with distinct functions and RNA-binding properties. Cell 151, 1055-1067.

Weick, E. M., and Miska, E. A. (2014). piRNAs: from biogenesis to function. Development 141, 3458-3471.

Yang, J. S., and Lai, E. C. (2010). Dicer-independent, Ago2-mediated microRNA biogenesis in vertebrates. Cell cycle 9, 4455-4460.

Yang, J. S., Maurin, T., and Lai, E. C. (2012). Functional parameters of Dicer-independent microRNA biogenesis. Rna 18, 945-957.

Yang, J. S., Maurin, T., Robine, N., Rasmussen, K. D., Jeffrey, K. L., Chandwani, R., Papapetrou, E. P., Sadelain, M., O'Carroll, D., and Lai, E. C. (2010). Conserved vertebrate mir-451 provides a platform for Dicer-independent, Ago2-mediated microRNA biogenesis. Proc Natl Acad Sci USA 107, 15163-15168.

Yekta, S., Shih, I. H., and Bartel, D. P. (2004). MicroRNA-directed cleavage of HOXB8 mRNA. Science 304, 594-596.

Yoda, M., Cifuentes, D., Izumi, N., Sakaguchi, Y., Suzuki, T., Giraldez, A. J., and Tomari, Y. (2013). Poly(A)-specific ribonuclease mediates 3'-end trimming of Argonaute2-cleaved precursor microRNAs. Cell reports 5, 715-726.

Zhao, Z., Cao, Y., Li, M., and Meng, A. (2001). Double-stranded RNA injection produces nonspecific defects in zebrafish. Dev Biol 229, 215-223.

---

What is claimed is:

1. A method of treating a mammal suffering from a condition, the method comprising administering to the mammal a therapeutically effective amount of an siRNA targeted to a target gene having a target sequence, wherein the siRNA comprises a guide sequence having at least one mismatch with respect to the target sequence, wherein the guide sequence mismatch with respect to the target sequence is located at guide position 6 of the guide sequence and is a G-G mismatch.

2. The method of claim 1, wherein the siRNA is administered parenterally.

3. The method of claim 1, wherein the siRNA is administered intravenously.

4. The method of claim 1, wherein the siRNA is administered by bolus injection into a target organ or tissue.

5. The method of claim 1, wherein the siRNA is administered intraperitoneally.

6. The method of claim 1, wherein the siRNA is administered subcutaneously.

7. The method of claim 1, wherein the mammal is a human.

* * * * *

SEQUENCE LISTING

```
<160> NUMBER OF SEQ ID NOS: 173

<210> SEQ ID NO 1
<211> LENGTH: 59
<212> TYPE: PRT
<213> ORGANISM: Artificial
<220> FEATURE:
<223> OTHER INFORMATION: zebrafish Ago2 segment

<400> SEQUENCE: 1

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 2
<211> LENGTH: 873
<212> TYPE: PRT
<213> ORGANISM: Artificial
<220> FEATURE:
<223> OTHER INFORMATION: zebrafish Ago2 polypeptide (isoform 1)

<400> SEQUENCE: 2
```

```
Met Tyr Pro Ile Gly Ala Ala Gly Ala Thr Glu Leu Phe Gln Gly Arg
1               5                   10                  15

Pro Ser Ser Gly Ser Asp Val Ser Ala Pro Ala Ser Pro Pro Ala Pro
            20                  25                  30

Gln Glu Tyr Val Phe Lys Pro Pro Gln Arg Pro Asp Phe Gly Thr Met
            35                  40                  45

Gly Arg Thr Ile Lys Leu Gln Ala Asn Phe Phe Glu Met Glu Ile Pro
50                  55                  60

Lys Leu Glu Val Tyr His Tyr Glu Ile Asp Ile Lys Pro Glu Lys Cys
65                  70                  75                  80

Pro Arg Gly Val Asn Arg Glu Ile Val Glu His Met Val Gln His Phe
                85                  90                  95

Lys Thr Gln Ile Phe Gly Asp Arg Lys Pro Val Tyr Asp Gly Arg Lys
            100                 105                 110

Asn Leu Tyr Thr Ala Met Pro Leu Pro Ile Gly Arg Asp Lys Val Glu
            115                 120                 125

Leu Glu Val Thr Ile Pro Gly Glu Gly Lys Asp Arg Ser Phe Lys Val
        130                 135                 140

Ala Ile Lys Trp Met Ser Cys Val Ser Leu Gln Ala Leu His Glu Ala
145                 150                 155                 160

Leu Ser Gly Arg Leu Pro Asn Ile Pro Phe Glu Thr Ile Gln Ala Leu
                165                 170                 175

Asp Val Val Met Arg His Leu Pro Ser Met Arg Tyr Thr Pro Val Gly
            180                 185                 190

Arg Ser Phe Phe Thr Pro Ser Glu Gly Cys Ser Asn Pro Leu Gly Gly
            195                 200                 205

Gly Arg Glu Val Trp Phe Gly Phe His Gln Ser Val Arg Pro Ser Leu
210                 215                 220

Trp Lys Met Met Leu Asn Ile Asp Val Ser Ala Thr Ala Phe Tyr Lys
225                 230                 235                 240

Ala Gln Pro Val Ile Glu Phe Met Cys Glu Val Leu Asp Phe Lys Ser
                245                 250                 255

Ile Glu Glu Gln Gln Lys Pro Leu Thr Asp Ser Gln Arg Val Lys Phe
            260                 265                 270

Thr Lys Glu Ile Lys Gly Leu Lys Val Glu Ile Thr His Cys Gly Gln
            275                 280                 285

Met Lys Arg Lys Tyr Arg Val Cys Asn Val Thr Arg Arg Pro Ala Ser
            290                 295                 300

His Gln Thr Phe Pro Leu Gln Gln Glu Asn Gly Gln Thr Ile Glu Cys
305                 310                 315                 320

Thr Val Ala Gln Tyr Phe Lys Asp Lys Tyr Lys Leu Val Leu Arg Tyr
                325                 330                 335

Pro His Leu Pro Cys Leu Gln Val Gly Gln Glu Gln Lys His Thr Tyr
            340                 345                 350

Leu Pro Leu Glu Val Cys Asn Ile Val Ala Gly Gln Arg Cys Ile Lys
            355                 360                 365

Lys Leu Thr Asp Asn Gln Thr Ser Thr Met Ile Arg Ala Thr Ala Arg
370                 375                 380

Ser Ala Pro Asp Arg Gln Asp Glu Ile Ser Lys Leu Met Arg Ser Ala
385                 390                 395                 400

Asn Phe Asn Thr Asp Pro Tyr Val Arg Glu Phe Gly Val Met Val Arg
                405                 410                 415

Asp Asp Met Thr Glu Val Asn Gly Arg Val Leu Gln Ala Pro Ser Ile
```

-continued

```
                420             425             430
Leu Tyr Gly Gly Arg Asn Lys Ala Ile Ala Thr Pro Val Gln Gly Val
                435             440             445

Trp Asp Met Arg Asn Lys Gln Phe His Thr Gly Ile Glu Ile Lys Val
        450             455             460

Trp Ala Ile Ala Cys Phe Ala Pro Gln Arg Gln Cys Thr Glu Leu Leu
465             470             475             480

Leu Lys Ala Phe Thr Asp Gln Leu Arg Lys Ile Ser Arg Asp Ala Gly
                485             490             495

Met Pro Ile Gln Gly Gln Pro Cys Phe Cys Lys Tyr Ala Gln Gly Ala
                500             505             510

Asp Ser Val Glu Pro Met Phe Lys His Leu Lys Tyr Thr Tyr Gln Gly
        515             520             525

Leu Gln Leu Val Val Ile Leu Pro Gly Lys Thr Pro Val Tyr Ala
        530             535             540

Glu Val Lys Arg Val Gly Asp Thr Val Leu Gly Met Ala Thr Gln Cys
545             550             555             560

Val Gln Val Lys Asn Val Gln Lys Thr Thr Pro Gln Thr Leu Ser Asn
                565             570             575

Leu Cys Leu Lys Ile Asn Val Lys Leu Gly Gly Val Asn Asn Ile Leu
                580             585             590

Leu Pro Gln Gly Arg Pro Leu Val Phe Gln Gln Pro Val Ile Phe Leu
                595             600             605

Gly Ala Asp Val Thr His Pro Pro Ala Gly Asp Gly Lys Lys Pro Ser
        610             615             620

Ile Ala Ala Val Val Gly Ser Met Asp Ala His Pro Ser Arg Tyr Cys
625             630             635             640

Ala Thr Val Arg Val Gln Gln His Arg Gln Asp Ile Ile Gln Asp Leu
                645             650             655

Ala Thr Met Val Arg Glu Leu Leu Ile Gln Phe Tyr Lys Ser Thr Arg
                660             665             670

Phe Lys Pro Thr Arg Ile Ile Tyr Tyr Arg Asp Gly Ile Ser Glu Gly
                675             680             685

Gln Phe Asn Gln Val Leu Gln His Glu Leu Leu Ala Ile Arg Glu Ala
        690             695             700

Cys Ile Lys Leu Glu Lys Asp Tyr Gln Pro Gly Ile Thr Phe Val Val
705             710             715             720

Val Gln Lys Arg His His Thr Arg Leu Phe Cys Met Asp Arg Asn Glu
                725             730             735

Arg Val Gly Lys Ser Gly Asn Ile Pro Ala Gly Thr Thr Val Asp Thr
                740             745             750

Lys Ile Thr His Pro Phe Glu Phe Asp Phe Tyr Leu Cys Ser His Ala
                755             760             765

Gly Ile Gln Gly Thr Ser Arg Pro Ser His Tyr His Val Leu Trp Asp
        770             775             780

Asp Asn His Phe Thr Ser Asp Glu Leu Gln Val Leu Thr Tyr Gln Leu
785             790             795             800

Cys His Thr Tyr Val Arg Cys Thr Arg Ser Val Ser Ile Pro Ala Pro
        805             810             815

Ala Tyr Tyr Ala His Leu Val Ala Phe Arg Ala Arg Tyr His Leu Val
        820             825             830

Asp Lys Glu His Asp Ser Ala Glu Gly Ser His Thr Ser Gly Gln Ser
        835             840             845
```

Asn Gly Arg Asp Gln Gln Ala Leu Ala Lys Ala Val Gln Ile His Gln
    850                 855                 860

Asp Thr Leu Arg Thr Met Tyr Phe Ala
865                 870

<210> SEQ ID NO 3
<211> LENGTH: 25
<212> TYPE: DNA
<213> ORGANISM: Artificial
<220> FEATURE:
<223> OTHER INFORMATION: Chimera N_for

<400> SEQUENCE: 3
gctacttgtt cttttgcag gatcc                                              25

<210> SEQ ID NO 4
<211> LENGTH: 40
<212> TYPE: DNA
<213> ORGANISM: Artificial
<220> FEATURE:
<223> OTHER INFORMATION: drAgo2 N_rev

<400> SEQUENCE: 4
cctcatggat ggcaagtgcc tcatgacaac atccagagcc                             40

<210> SEQ ID NO 5
<211> LENGTH: 40
<212> TYPE: DNA
<213> ORGANISM: Artificial
<220> FEATURE:
<223> OTHER INFORMATION: hsAGO2 N_rev

<400> SEQUENCE: 5
cctcatagag ggcaaatgtc tcatgaccac gtccagggcc                             40

<210> SEQ ID NO 6
<211> LENGTH: 20
<212> TYPE: DNA
<213> ORGANISM: Artificial
<220> FEATURE:
<223> OTHER INFORMATION: drAgo2 body_for

<400> SEQUENCE: 6
tggacggcta ccaaacatcc                                                   20

<210> SEQ ID NO 7
<211> LENGTH: 20
<212> TYPE: DNA
<213> ORGANISM: Artificial
<220> FEATURE:
<223> OTHER INFORMATION: hsAGO2 body_for

<400> SEQUENCE: 7
tgcctagcgt cccttttgag                                                   20

<210> SEQ ID NO 8
<211> LENGTH: 21
<212> TYPE: DNA
<213> ORGANISM: Artificial
<220> FEATURE:
<223> OTHER INFORMATION: Chimera body_rev

<400> SEQUENCE: 8
tggtttgtcc aaactcatca a                                                 21

<210> SEQ ID NO 9
<211> LENGTH: 35
<212> TYPE: DNA
<213> ORGANISM: Artificial
<220> FEATURE:
<223> OTHER INFORMATION: drAgo2 D683A_sense

<400> SEQUENCE: 9
catcatctac tacagagccg gcatctctga aggcc                              35

<210> SEQ ID NO 10
<211> LENGTH: 35
<212> TYPE: DNA
<213> ORGANISM: Artificial
<220> FEATURE:
<223> OTHER INFORMATION: drAgo2 D683A_antisense

<400> SEQUENCE: 10
ggccttcaga gatgccggct ctgtagtaga tgatg                              35

<210> SEQ ID NO 11
<211> LENGTH: 30
<212> TYPE: DNA
<213> ORGANISM: Artificial
<220> FEATURE:
<223> OTHER INFORMATION: drAgo2 D651E_sense

<400> SEQUENCE: 11
cagcaccggc aggagatcat tcaggatctg                                    30

<210> SEQ ID NO 12
<211> LENGTH: 30
<212> TYPE: DNA
<213> ORGANISM: Artificial
<220> FEATURE:
<223> OTHER INFORMATION: drAgo2 D651E_antisense

<400> SEQUENCE: 12
cagatcctga atgatctcct gccggtgctg                                    30

<210> SEQ ID NO 13
<211> LENGTH: 33
<212> TYPE: DNA
<213> ORGANISM: Artificial
<220> FEATURE:
<223> OTHER INFORMATION: drAgo2 Y680F_sense

<400> SEQUENCE: 13
ccaacacgca tcatcttcta cagagacggc atc                                33

<210> SEQ ID NO 14
<211> LENGTH: 33
<212> TYPE: DNA
<213> ORGANISM: Artificial
<220> FEATURE:
<223> OTHER INFORMATION: drAgo2 Y680F_antisense

<400> SEQUENCE: 14
gatgccgtct ctgtagaaga tgatgcgtgt tgg                                33

<210> SEQ ID NO 15
<211> LENGTH: 31
<212> TYPE: DNA
<213> ORGANISM: Artificial
<220> FEATURE:
<223> OTHER INFORMATION: hsAGO2 D669A_sense

```
<400> SEQUENCE: 15
tcatcttcta ccgcgccggt gtctctgaag g                              31

<210> SEQ ID NO 16
<211> LENGTH: 31
<212> TYPE: DNA
<213> ORGANISM: Artificial
<220> FEATURE:
<223> OTHER INFORMATION: hsAGO2 D669A_antisense

<400> SEQUENCE: 16
ccttcagaga caccggcgcg gtagaagatg a                              31

<210> SEQ ID NO 17
<211> LENGTH: 31
<212> TYPE: DNA
<213> ORGANISM: Artificial
<220> FEATURE:
<223> OTHER INFORMATION: hsAGO2 E637D_sense

<400> SEQUENCE: 17
gcagcaccgg caggatatca tacaagacct g                              31

<210> SEQ ID NO 18
<211> LENGTH: 31
<212> TYPE: DNA
<213> ORGANISM: Artificial
<220> FEATURE:
<223> OTHER INFORMATION: hsAGO2 E637D_antisense

<400> SEQUENCE: 18
caggtcttgt atgatatcct gccggtgctg c                              31

<210> SEQ ID NO 19
<211> LENGTH: 32
<212> TYPE: DNA
<213> ORGANISM: Artificial
<220> FEATURE:
<223> OTHER INFORMATION: hsAGO2_F666Y_sense

<400> SEQUENCE: 19
cccacccgca tcatctatta ccgcgacggt gt                             32

<210> SEQ ID NO 20
<211> LENGTH: 32
<212> TYPE: DNA
<213> ORGANISM: Artificial
<220> FEATURE:
<223> OTHER INFORMATION: hsAGO2_F666Y_antisense

<400> SEQUENCE: 20
acaccgtcgc ggtaatagat gatgcgggtg gg                             32

<210> SEQ ID NO 21
<211> LENGTH: 73
<212> TYPE: DNA
<213> ORGANISM: Artificial
<220> FEATURE:
<223> OTHER INFORMATION: Zeocin target_miR-430_for

<400> SEQUENCE: 21
actgactcga gcctctagaa ataagctacc ccaacttgat agcactttat aagctatagt     60
gagtcgtatt acg                                                       73
```

<210> SEQ ID NO 22
<211> LENGTH: 73
<212> TYPE: DNA
<213> ORGANISM: Artificial
<220> FEATURE:
<223> OTHER INFORMATION: Zeocin target_miR-430_rev

<400> SEQUENCE: 22
cgtaatacga ctcactatag cttataaagt gctatcaagt tggggtagct tatttctaga      60
ggctcgagtc agt                                                        73

<210> SEQ ID NO 23
<211> LENGTH: 73
<212> TYPE: DNA
<213> ORGANISM: Artificial
<220> FEATURE:
<223> OTHER INFORMATION: Zeocin_miR-430_10-11 mm_for

<400> SEQUENCE: 23
actgactcga gcctctagaa ataagctacc ccaacttctt agcactttat aagctatagt      60
gagtcgtatt acg                                                        73

<210> SEQ ID NO 24
<211> LENGTH: 73
<212> TYPE: DNA
<213> ORGANISM: Artificial
<220> FEATURE:
<223> OTHER INFORMATION: Zeocin miR-430_10-11 mm_rev

<400> SEQUENCE: 24
cgtaatacga ctcactatag cttataaagt gctaagaagt tggggtagct tatttctaga      60
ggctcgagtc agt                                                        73

<210> SEQ ID NO 25
<211> LENGTH: 73
<212> TYPE: DNA
<213> ORGANISM: Artificial
<220> FEATURE:
<223> OTHER INFORMATION: Zeocin_miR-430_G-G_for

<400> SEQUENCE: 25
actgactcga gcctctagaa ataagctacc ccaacttgat aggactttat aagctatagt      60
gagtcgtatt acg                                                        73

<210> SEQ ID NO 26
<211> LENGTH: 73
<212> TYPE: DNA
<213> ORGANISM: Artificial
<220> FEATURE:
<223> OTHER INFORMATION: Zeocin_miR-430_G-G_rev

<400> SEQUENCE: 26
cgtaatacga ctcactatag cttataaagt cctatcaagt tggggtagct tatttctaga      60
ggctcgagtc agt                                                        73

<210> SEQ ID NO 27
<211> LENGTH: 22
<212> TYPE: DNA
<213> ORGANISM: Artificial
<220> FEATURE:
<223> OTHER INFORMATION: Zeocin probe_for

<400> SEQUENCE: 27
attcaggatc atggccaagt tg                                          22

<210> SEQ ID NO 28
<211> LENGTH: 54
<212> TYPE: DNA
<213> ORGANISM: Artificial
<220> FEATURE:
<223> OTHER INFORMATION: Zeocin probe_rev

<400> SEQUENCE: 28
ttctaatacg actcactata gggagaagga ggtttctaga ggctcgagtc agtc       54

<210> SEQ ID NO 29
<211> LENGTH: 60
<212> TYPE: DNA
<213> ORGANISM: Artificial
<220> FEATURE:
<223> OTHER INFORMATION: GFP probe

<400> SEQUENCE: 29
gtccagctcg accaggatgg gcaccacccc ggtgaacagc tcctcgccct tgctcaccat 60

<210> SEQ ID NO 30
<211> LENGTH: 42
<212> TYPE: DNA
<213> ORGANISM: Artificial
<220> FEATURE:
<223> OTHER INFORMATION: 168-nt target_for

<400> SEQUENCE: 30
gcgtaatacg actcactata gggtcacatc tcatctacct cc                   42

<210> SEQ ID NO 31
<211> LENGTH: 90
<212> TYPE: DNA
<213> ORGANISM: Artificial
<220> FEATURE:
<223> OTHER INFORMATION: 168-nt target_miR-430_perfect_rev

<400> SEQUENCE: 31
cccatttaca tcgcgttgag tgtagaacgg ttgtataaaa ggtaaagtgc tatcaagttg 60
gggtagatcc agaggaattc attatcagtg                                  90

<210> SEQ ID NO 32
<211> LENGTH: 90
<212> TYPE: DNA
<213> ORGANISM: Artificial
<220> FEATURE:
<223> OTHER INFORMATION: 168-nt target_miR-430_10-11 mm_rev

<400> SEQUENCE: 32
cccatttaca tcgcgttgag tgtagaacgg ttgtataaaa ggtaaagtgc taagaagttg 60
gggtagatcc agaggaattc attatcagtg                                  90

<210> SEQ ID NO 33
<211> LENGTH: 90
<212> TYPE: DNA
<213> ORGANISM: Artificial
<220> FEATURE:
<223> OTHER INFORMATION: 168-nt target_miR-430_G-G_rev

<400> SEQUENCE: 33
cccatttaca tcgcgttgag tgtagaacgg ttgtataaaa ggtaaagtcc tatcaagttg 60
gggtagatcc agaggaattc attatcagtg                                        90

<210> SEQ ID NO 34
<211> LENGTH: 100
<212> TYPE: DNA
<213> ORGANISM: Artificial
<220> FEATURE:
<223> OTHER INFORMATION: 80-nt target_miR-430

<400> SEQUENCE: 34
ttgttgttgt tgttgttgtt aaagtgctat caagttgggg tagtgttgtt gttgttgttg      60
ttgttgttgt tgttgctccc tatagtgagt cgtattagaa                            100

<210> SEQ ID NO 35
<211> LENGTH: 100
<212> TYPE: DNA
<213> ORGANISM: Artificial
<220> FEATURE:
<223> OTHER INFORMATION: 80-nt target_miR-430_G-G

<400> SEQUENCE: 35
ttgttgttgt tgttgttgtt aaagtcctat caagttgggg tagtgttgtt gttgttgttg      60
ttgttgttgt tgttgctccc tatagtgagt cgtattagaa                            100

<210> SEQ ID NO 36
<211> LENGTH: 74
<212> TYPE: DNA
<213> ORGANISM: Artificial
<220> FEATURE:
<223> OTHER INFORMATION: miR-430 capture

<400> SEQUENCE: 36
mumcmumumc mcmumcmcmg mcmamcmcma mcmamcmamg mcmamcmumu mamamcmcmu      60
mumamcmamc mamc                                                         74

<210> SEQ ID NO 37
<211> LENGTH: 31
<212> TYPE: DNA
<213> ORGANISM: Artificial
<220> FEATURE:
<223> OTHER INFORMATION: miR-430 competitor

<400> SEQUENCE: 37
aaggttaagt gctgtgtggt gcggaggaag a                                     31

<210> SEQ ID NO 38
<211> LENGTH: 23
<212> TYPE: RNA
<213> ORGANISM: Artificial
<220> FEATURE:
<223> OTHER INFORMATION: miR-430b guide

<400> SEQUENCE: 38
aaagugcuau caaguugggg uag                                              23

<210> SEQ ID NO 39
<211> LENGTH: 22
<212> TYPE: RNA
<213> ORGANISM: Artificial
<220> FEATURE:
<223> OTHER INFORMATION: miR-430b passenger

<400> SEQUENCE: 39
acccuaacuu uagcaucuuu cu                                               22

<210> SEQ ID NO 40
<211> LENGTH: 42
<212> TYPE: RNA
<213> ORGANISM: Artificial
<220> FEATURE:
<223> OTHER INFORMATION: pre-miR-451 (ancestral)

<400> SEQUENCE: 40
aaaccguuac cauuacugag uuuaguaaug guaaggguuc ug                          42

<210> SEQ ID NO 41
<211> LENGTH: 42
<212> TYPE: RNA
<213> ORGANISM: Artificial
<220> FEATURE:
<223> OTHER INFORMATION: pre-miR-451 (amniote)

<400> SEQUENCE: 41
aaaccguuac cauuacugag uuuaguaaug guaacgguuc ug                          42

<210> SEQ ID NO 42
<211> LENGTH: 59
<212> TYPE: PRT
<213> ORGANISM: Artificial
<220> FEATURE:
<223> OTHER INFORMATION: Ago2 PIWI domain

<400> SEQUENCE: 42

Pro Asn Arg Tyr Cys Ala Thr Val Arg Val Gln Gln His Arg Gln Glu
1               5                   10                  15

Ile Ile Gln Asp Leu Ala Ala Met Val Arg Glu Leu Leu Ile Gln Phe
            20                  25                  30

Tyr Lys Ser Thr Arg Phe Lys Pro Thr Arg Ile Ile Phe Tyr Arg Asp
        35                  40                  45

Gly Val Ser Glu Gly Gln Phe Gln Gln Val Leu
    50                  55

<210> SEQ ID NO 43
<211> LENGTH: 59
<212> TYPE: PRT
<213> ORGANISM: Artificial
<220> FEATURE:
<223> OTHER INFORMATION: Ago2 PIWI domain

<400> SEQUENCE: 43

Pro Asn Arg Tyr Cys Ala Thr Val Arg Val Gln Gln His Arg Gln Glu
1               5                   10                  15

Ile Ile Gln Asp Leu Ala Ala Met Val Arg Glu Leu Leu Ile Gln Phe
            20                  25                  30

Tyr Lys Ser Thr Arg Phe Lys Pro Thr Arg Ile Ile Phe Tyr Arg Asp
        35                  40                  45

Gly Val Ser Glu Gly Gln Phe Gln Gln Val Leu
    50                  55

<210> SEQ ID NO 44
<211> LENGTH: 59
<212> TYPE: PRT
<213> ORGANISM: Artificial
<220> FEATURE:
<223> OTHER INFORMATION: Ago2 PIWI domain

<400> SEQUENCE: 44

-continued

Pro Asn Arg Tyr Cys Ala Thr Val Arg Val Gln Gln His Arg Gln Glu
1               5                   10                  15

Ile Ile Gln Asp Leu Ala Ala Met Val Arg Glu Leu Leu Ile Gln Phe
            20                  25                  30

Tyr Lys Ser Thr Arg Phe Lys Pro Thr Arg Ile Ile Phe Tyr Arg Asp
        35                  40                  45

Gly Val Ser Glu Gly Gln Phe Gln Gln Val Leu
    50                  55

<210> SEQ ID NO 45
<211> LENGTH: 59
<212> TYPE: PRT
<213> ORGANISM: Artificial
<220> FEATURE:
<223> OTHER INFORMATION: Ago2 PIWI domain

<400> SEQUENCE: 45

Pro Asn Arg Tyr Cys Ala Thr Val Arg Val Gln Gln His Arg Gln Glu
1               5                   10                  15

Ile Ile Gln Asp Leu Ser Ala Met Val Arg Glu Leu Leu Ile Gln Phe
            20                  25                  30

Tyr Lys Ser Thr Arg Phe Lys Pro Thr Arg Ile Ile Phe Tyr Arg Asp
        35                  40                  45

Gly Val Ser Glu Gly Gln Phe Gln Gln Val Leu
    50                  55

<210> SEQ ID NO 46
<211> LENGTH: 59
<212> TYPE: PRT
<213> ORGANISM: Artificial
<220> FEATURE:
<223> OTHER INFORMATION: Ago2 PIWI domain

<400> SEQUENCE: 46

Pro Asn Arg Tyr Cys Ala Thr Val Arg Val Gln Gln His Arg Gln Glu
1               5                   10                  15

Ile Ile Gln Asp Leu Ala Ala Met Val Arg Glu Leu Leu Ile Gln Phe
            20                  25                  30

Tyr Lys Ser Thr Arg Phe Lys Pro Thr Arg Ile Ile Phe Tyr Arg Asp
        35                  40                  45

Gly Val Ser Glu Gly Gln Phe Gln Gln Val Leu
    50                  55

<210> SEQ ID NO 47
<211> LENGTH: 59
<212> TYPE: PRT
<213> ORGANISM: Artificial
<220> FEATURE:
<223> OTHER INFORMATION: Ago2 PIWI domain

<400> SEQUENCE: 47

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

```
<210> SEQ ID NO 48
<211> LENGTH: 59
<212> TYPE: PRT
<213> ORGANISM: Artificial
<220> FEATURE:
<223> OTHER INFORMATION: Ago2 PIWI domain

<400> SEQUENCE: 48

Pro Ser Arg Tyr Cys Ala Thr Val Arg Val Gln Gln His Arg Gln Asp
1               5                   10                  15

Ile Ile Gln Asp Leu Ala Asn Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 49
<211> LENGTH: 59
<212> TYPE: PRT
<213> ORGANISM: Artificial
<220> FEATURE:
<223> OTHER INFORMATION: Ago2 PIWI domain

<400> SEQUENCE: 49

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 50
<211> LENGTH: 59
<212> TYPE: PRT
<213> ORGANISM: Artificial
<220> FEATURE:
<223> OTHER INFORMATION: Ago2 PIWI domain

<400> SEQUENCE: 50

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 51
<211> LENGTH: 59
<212> TYPE: PRT
<213> ORGANISM: Artificial
<220> FEATURE:
<223> OTHER INFORMATION: Ago2 PIWI domain

<400> SEQUENCE: 51

Pro Asn Arg Tyr Cys Ala Thr Val Arg Val Gln Gln His Arg Gln Glu
1               5                   10                  15

Ile Ile Gln Asp Leu Ser Ala Met Val Arg Glu Leu Leu Ile Gln Phe
```

```
                 20                  25                  30

Tyr Lys Ser Thr Arg Phe Lys Pro Thr Arg Ile Ile Phe Tyr Arg Asp
         35                  40                  45

Gly Ile Ser Glu Gly Gln Phe Asn Gln Val Leu
         50                  55

<210> SEQ ID NO 52
<211> LENGTH: 59
<212> TYPE: PRT
<213> ORGANISM: Artificial
<220> FEATURE:
<223> OTHER INFORMATION: Ago2 PIWI domain

<400> SEQUENCE: 52

Pro Ser Arg Tyr Cys Ala Thr Val Arg Val Gln His His Arg Gln Glu
1               5                  10                  15

Ile Ile Gln Asp Leu Gly Thr Met Val Arg Glu Leu Leu Ile Gln Phe
                 20                  25                  30

Tyr Lys Ser Thr Arg Phe Lys Pro Thr Arg Ile Ile Phe Tyr Arg Asp
         35                  40                  45

Gly Val Ser Glu Gly Gln Phe Gln Gln Val Leu
         50                  55

<210> SEQ ID NO 53
<211> LENGTH: 21
<212> TYPE: RNA
<213> ORGANISM: Artificial
<220> FEATURE:
<223> OTHER INFORMATION: ancestral pre-miR-451 sequence

<400> SEQUENCE: 53
uuuaguaaug guaagggucu g                                           21

<210> SEQ ID NO 54
<211> LENGTH: 20
<212> TYPE: RNA
<213> ORGANISM: Artificial
<220> FEATURE:
<223> OTHER INFORMATION: ancestral pre-miR-451 sequence

<400> SEQUENCE: 54
gagucauuac cauugccaaa                                             20

<210> SEQ ID NO 55
<211> LENGTH: 22
<212> TYPE: RNA
<213> ORGANISM: Artificial
<220> FEATURE:
<223> OTHER INFORMATION: amniote pre-miR-451 sequence

<400> SEQUENCE: 55
uuuaguaaug guaacgguuc ug                                          22

<210> SEQ ID NO 56
<211> LENGTH: 20
<212> TYPE: RNA
<213> ORGANISM: Artificial
<220> FEATURE:
<223> OTHER INFORMATION: amniote pre-miR-451 sequence

<400> SEQUENCE: 56
gagucauuac cauugccaaa                                             20
```

```
<210> SEQ ID NO 57
<211> LENGTH: 59
<212> TYPE: PRT
<213> ORGANISM: Artificial
<220> FEATURE:
<223> OTHER INFORMATION: Ago2 PIWI domain

<400> SEQUENCE: 57

Pro Ser Arg Tyr Cys Ala Thr Val Arg Val Gln Gln His Arg Gln Glu
1               5                   10                  15

Ile Ile Gln Asp Leu Ser Ala Met Val Arg Glu Leu Leu Ile Gln Phe
            20                  25                  30

Tyr Lys Ser Thr Arg Phe Lys Pro Thr Arg Ile Ile Phe Tyr Arg Asp
        35                  40                  45

Gly Ile Ser Glu Gly Gln Phe Asn Gln Val Leu
    50                  55

<210> SEQ ID NO 58
<211> LENGTH: 58
<212> TYPE: PRT
<213> ORGANISM: Artificial
<220> FEATURE:
<223> OTHER INFORMATION: Ago2 PIWI domain

<400> SEQUENCE: 58

Pro Ser Arg Tyr Cys Ala Thr Val Arg Val Gln Gln His Arg Gln Asp
1               5                   10                  15

Ile Ile Gln Asp Leu Ala Ala Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe His Gln Ala
    50                  55

<210> SEQ ID NO 59
<211> LENGTH: 59
<212> TYPE: PRT
<213> ORGANISM: Artificial
<220> FEATURE:
<223> OTHER INFORMATION: Ago2 PIWI domain

<400> SEQUENCE: 59

Pro Ser Arg Tyr Cys Ala Thr Val Arg Val Gln Gln His Arg Gln Asp
1               5                   10                  15

Ile Ile Gln Asp Leu Ala Ala Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 60
<211> LENGTH: 59
<212> TYPE: PRT
<213> ORGANISM: Artificial
<220> FEATURE:
<223> OTHER INFORMATION: Ago2 PIWI domain

<400> SEQUENCE: 60

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
```

```
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 61
<211> LENGTH: 59
<212> TYPE: PRT
<213> ORGANISM: Artificial
<220> FEATURE:
<223> OTHER INFORMATION: Ago2 PIWI domain

<400> SEQUENCE: 61

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 62
<211> LENGTH: 59
<212> TYPE: PRT
<213> ORGANISM: Artificial
<220> FEATURE:
<223> OTHER INFORMATION: Ago2 PIWI domain

<400> SEQUENCE: 62

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 63
<211> LENGTH: 59
<212> TYPE: PRT
<213> ORGANISM: Artificial
<220> FEATURE:
<223> OTHER INFORMATION: Ago2 PIWI domain

<400> SEQUENCE: 63

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 64
<211> LENGTH: 59
<212> TYPE: PRT
<213> ORGANISM: Artificial
```

<220> FEATURE:
<223> OTHER INFORMATION: Ago2 PIWI domain

<400> SEQUENCE: 64

```
Pro Ser Arg Tyr Cys Ala Thr Val Arg Val Gln Gln His Arg Gln Asp
1               5                   10                  15

Ile Ile Gln Asp Leu Ala Ala Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55
```

<210> SEQ ID NO 65
<211> LENGTH: 59
<212> TYPE: PRT
<213> ORGANISM: Artificial
<220> FEATURE:
<223> OTHER INFORMATION: Ago2 PIWI domain

<400> SEQUENCE: 65

```
Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55
```

<210> SEQ ID NO 66
<211> LENGTH: 59
<212> TYPE: PRT
<213> ORGANISM: Artificial
<220> FEATURE:
<223> OTHER INFORMATION: Ago2 PIWI domain

<400> SEQUENCE: 66

```
Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55
```

<210> SEQ ID NO 67
<211> LENGTH: 59
<212> TYPE: PRT
<213> ORGANISM: Artificial
<220> FEATURE:
<223> OTHER INFORMATION: Ago2 PIWI domain

<400> SEQUENCE: 67

```
Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45
```

Gly Ile Ser Glu Gly Gln Phe Asn Gln Val Leu
         50                  55

<210> SEQ ID NO 68
<211> LENGTH: 59
<212> TYPE: PRT
<213> ORGANISM: Artificial
<220> FEATURE:
<223> OTHER INFORMATION: Ago2 PIWI domain

<400> SEQUENCE: 68

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
                20                  25                  30

Tyr Lys Ser Thr Arg Phe Lys Pro Thr Arg Ile Ile Tyr Tyr Arg Asp
            35                  40                  45

Gly Ile Ser Glu Gly Gln Phe Asn Gln Val Leu
         50                  55

<210> SEQ ID NO 69
<211> LENGTH: 59
<212> TYPE: PRT
<213> ORGANISM: Artificial
<220> FEATURE:
<223> OTHER INFORMATION: Ago2 PIWI domain

<400> SEQUENCE: 69

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
                20                  25                  30

Tyr Lys Ser Thr Arg Phe Lys Pro Thr Arg Ile Ile Tyr Tyr Arg Asp
            35                  40                  45

Gly Ile Ser Glu Gly Gln Phe Asn Gln Val Leu
         50                  55

<210> SEQ ID NO 70
<211> LENGTH: 59
<212> TYPE: PRT
<213> ORGANISM: Artificial
<220> FEATURE:
<223> OTHER INFORMATION: Ago2 PIWI domain

<400> SEQUENCE: 70

Pro Ser Arg Tyr Cys Ala Thr Val Arg Val Gln Gln His Arg Gln Asp
1               5                   10                  15

Ile Ile Gln Asp Leu Ala Ala Met Val Arg Glu Leu Leu Ile Gln Phe
                20                  25                  30

Tyr Lys Ser Thr Arg Phe Lys Pro Thr Arg Ile Ile Tyr Tyr Arg Asp
            35                  40                  45

Gly Ile Ser Glu Gly Gln Phe Asn Gln Val Leu
         50                  55

<210> SEQ ID NO 71
<211> LENGTH: 59
<212> TYPE: PRT
<213> ORGANISM: Artificial
<220> FEATURE:
<223> OTHER INFORMATION: Ago2 PIWI domain

<400> SEQUENCE: 71

Pro Ser Arg Tyr Cys Ala Thr Val Arg Val Gln Gln His Arg Gln Glu
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 72
<211> LENGTH: 59
<212> TYPE: PRT
<213> ORGANISM: Artificial
<220> FEATURE:
<223> OTHER INFORMATION: Ago2 PIWI domain

<400> SEQUENCE: 72

Pro Ser Arg Tyr Cys Ala Thr Val Arg Val Gln Gln His Arg Gln Glu
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 73
<211> LENGTH: 59
<212> TYPE: PRT
<213> ORGANISM: Artificial
<220> FEATURE:
<223> OTHER INFORMATION: Ago2 PIWI domain

<400> SEQUENCE: 73

Pro Ser Arg Tyr Cys Ala Thr Val Arg Val Gln Gln His Arg Gln Glu
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 74
<211> LENGTH: 59
<212> TYPE: PRT
<213> ORGANISM: Artificial
<220> FEATURE:
<223> OTHER INFORMATION: Ago2 PIWI domain

<400> SEQUENCE: 74

Pro Ser Arg Tyr Cys Ala Thr Val Arg Val Gln Gln His Arg Gln Glu
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 75
<211> LENGTH: 59
<212> TYPE: PRT
<213> ORGANISM: Artificial
<220> FEATURE:
<223> OTHER INFORMATION: Ago2 PIWI domain

<400> SEQUENCE: 75

Pro Ser Arg Tyr Cys Ala Thr Val Arg Val Gln Gln His Arg Gln Glu
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 76
<211> LENGTH: 59
<212> TYPE: PRT
<213> ORGANISM: Artificial
<220> FEATURE:
<223> OTHER INFORMATION: Ago2 PIWI domain

<400> SEQUENCE: 76

Pro Ser Arg Tyr Cys Ala Thr Val Arg Val Gln Gln His Arg Gln Asp
1               5                   10                  15

Ile Ile Gln Asp Leu Ala Asn Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 77
<211> LENGTH: 59
<212> TYPE: PRT
<213> ORGANISM: Artificial
<220> FEATURE:
<223> OTHER INFORMATION: Ago2 PIWI domain

<400> SEQUENCE: 77

Pro Ser Arg Tyr Cys Ala Thr Val Arg Val Gln Gln His Arg Gln Asp
1               5                   10                  15

Ile Ile Gln Asp Leu Ala Asn Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 78
<211> LENGTH: 59
<212> TYPE: PRT
<213> ORGANISM: Artificial
<220> FEATURE:
<223> OTHER INFORMATION: Ago2 PIWI domain

<400> SEQUENCE: 78

Pro Ser Arg Tyr Cys Ala Thr Val Arg Val Gln Gln His Arg Gln Asp
1               5                   10                  15

Ile Ile Gln Asp Leu Ala Asn Met Val Arg Glu Leu Leu Ile Gln Phe
            20                  25                  30

Tyr Lys Ser Thr Arg Phe Lys Pro Thr Arg Ile Ile Tyr Tyr Arg Asp
         35                  40                  45

Gly Ile Ser Glu Gly Gln Phe Asn Gln Val Leu
     50                  55

<210> SEQ ID NO 79
<211> LENGTH: 59
<212> TYPE: PRT
<213> ORGANISM: Artificial
<220> FEATURE:
<223> OTHER INFORMATION: Ago2 PIWI domain

<400> SEQUENCE: 79

Pro Ser Arg Tyr Cys Ala Thr Val Arg Val Gln Gln His Arg Gln Asp
1               5                   10                  15

Ile Ile Gln Asp Leu Ala Asn Met Val Arg Glu Leu Leu Ile Gln Phe
            20                  25                  30

Tyr Lys Ser Thr Arg Phe Lys Pro Thr Arg Ile Ile Tyr Tyr Arg Asp
         35                  40                  45

Gly Ile Ser Glu Gly Gln Phe Asn Gln Val Leu
     50                  55

<210> SEQ ID NO 80
<211> LENGTH: 59
<212> TYPE: PRT
<213> ORGANISM: Artificial
<220> FEATURE:
<223> OTHER INFORMATION: Ago2 PIWI domain

<400> SEQUENCE: 80

Pro Ser Arg Tyr Cys Ala Thr Val Arg Val Gln Gln His Arg Gln Asp
1               5                   10                  15

Ile Ile Gln Asp Leu Ala Asn Met Val Arg Glu Leu Leu Ile Gln Phe
            20                  25                  30

Tyr Lys Ser Thr Arg Phe Lys Pro Thr Arg Ile Ile Tyr Tyr Arg Asp
         35                  40                  45

Gly Ile Ser Glu Gly Gln Phe Asn Gln Val Leu
     50                  55

<210> SEQ ID NO 81
<211> LENGTH: 59
<212> TYPE: PRT
<213> ORGANISM: Artificial
<220> FEATURE:
<223> OTHER INFORMATION: Ago2 PIWI domain

<400> SEQUENCE: 81

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
         35                  40                  45

Gly Ile Ser Glu Gly Gln Phe Asn Gln Val Leu
     50                  55

<210> SEQ ID NO 82
<211> LENGTH: 59
<212> TYPE: PRT

```
<213> ORGANISM: Artificial
<220> FEATURE:
<223> OTHER INFORMATION: Ago2 PIWI domain

<400> SEQUENCE: 82

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 83
<211> LENGTH: 59
<212> TYPE: PRT
<213> ORGANISM: Artificial
<220> FEATURE:
<223> OTHER INFORMATION: Ago2 PIWI domain

<400> SEQUENCE: 83

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 84
<211> LENGTH: 59
<212> TYPE: PRT
<213> ORGANISM: Artificial
<220> FEATURE:
<223> OTHER INFORMATION: Ago2 PIWI domain

<400> SEQUENCE: 84

Pro Ser Arg Tyr Cys Ala Thr Val Arg Val Gln Gln His Arg Gln Asp
1               5                   10                  15

Ile Ile Gln Asp Leu Ala Thr Met Val Arg Glu Leu Leu Ile Gln Phe
            20                  25                  30

Tyr Lys Ser Thr Arg Phe Lys Pro Thr Arg Ile Ile Tyr Tyr Arg Asp
        35                  40                  45

Gly Ile Ser Glu Gly Gln Phe Asn Gln Val Leu
    50                  55

<210> SEQ ID NO 85
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 85
aaaccgttac cattactgag tttagtaatg gtaatggttc tc                    42

<210> SEQ ID NO 86
<211> LENGTH: 42
<212> TYPE: DNA
<213> ORGANISM: Artificial
```

-continued

<220> FEATURE:
<223> OTHER INFORMATION: pre-miR-451 DNA sequence

<400> SEQUENCE: 86
aaaccgttac cattactgag tttagtaatg gtaatggttc tc         42

<210> SEQ ID NO 87
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 87
aaaccgttac cattactgag tttagtaatg gtaatggttc tc         42

<210> SEQ ID NO 88
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 88
aaaccgttac cattactgag tttagtaatg gtaatggttc tc         42

<210> SEQ ID NO 89
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 89
aaaccgttac cattactgag tttagtaatg gtaacggttc tc         42

<210> SEQ ID NO 90
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 90
aaaccgttac cattactgag tttagtaatg gtaagggttc tc         42

<210> SEQ ID NO 91
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 91
aaaccgttac cattactgag tttagtaatg gtaagggttc tc         42

<210> SEQ ID NO 92
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 92
aaaccgttac cattactgag tttagtaatg gtaagggttc tc         42

```
<210> SEQ ID NO 93
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 93
aaaccgttac cattactgag tttagtaatg gtaagggttc tc                    42

<210> SEQ ID NO 94
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 94
aaaccgttac cattactgag tttagtaatg gtaacggttc tc                    42

<210> SEQ ID NO 95
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 95
aaaccgttac cattactgag tttagtaatg gtaatggttc tc                    42

<210> SEQ ID NO 96
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 96
aaaccgttac cattactgag tttagtaatg gtaacggttc tc                    42

<210> SEQ ID NO 97
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 97
aaaccgttac cattactgag tttagtaatg gtaacggttc tc                    42

<210> SEQ ID NO 98
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 98
aaaccgttac cattactgag tttagtaatg gtaacggttc tc                    42

<210> SEQ ID NO 99
<211> LENGTH: 41
<212> TYPE: DNA
<213> ORGANISM: Artificial
<220> FEATURE:
<223> OTHER INFORMATION: pre-miR-451 DNA sequence
```

<400> SEQUENCE: 99
aaaccgttac cattactgag ttagtaatgg taacggttct c         41

<210> SEQ ID NO 100
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 100
aaaccgttac cattactgag tttagtaatg gtaacggttc tc        42

<210> SEQ ID NO 101
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 101
aaaccgttac cattactgag tttagtaatg gtaacggttc tc        42

<210> SEQ ID NO 102
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 102
aaaccgttac cattactgag tttagtaatg gtaacggttc tc        42

<210> SEQ ID NO 103
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 103
aaaccgttac cattactgag tttagtaatg gtaatggttc tc        42

<210> SEQ ID NO 104
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 104
aaaccgttac cattactgag tttagtaatg gtgacggttc tc        42

<210> SEQ ID NO 105
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 105
aaaccgttac cattactgag tttagtaatg gtgacggttc tc        42

<210> SEQ ID NO 106

-continued

<210> SEQ ID NO 106
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 106
aaaccgttac cattactgag tttagtaatg gtgacggttc tc                          42

<210> SEQ ID NO 107
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 107
aaaccgttac cattactgag tttagtaatg gtgacggttc tc                          42

<210> SEQ ID NO 108
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 108
aaaccgttac cattactgag tttagtaatg gtaacggttc tc                          42

<210> SEQ ID NO 109
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 109
aaaccgttac cattacttag tttagtaatg gtaacggttc tc                          42

<210> SEQ ID NO 110
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 110
aaaccgttac cattactgag tttagtaatg gtaacggttc tc                          42

<210> SEQ ID NO 111
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 111
aaaccgttac cattactgag tttagtaatg gtaacggttc tc                          42

<210> SEQ ID NO 112
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 112
aaaccgttac cattactgag tttagtaatg gtaacggttc tc    42

<210> SEQ ID NO 113
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 113
aaaccgttac cattactgag tttagtaatg gtaacggttc tc    42

<210> SEQ ID NO 114
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 114
aaaccgttac cattactgag tttagtaatg gtaacggttc tc    42

<210> SEQ ID NO 115
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 115
aaaccgttac cattactgag tttagtaatg gtaacggttc tc    42

<210> SEQ ID NO 116
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 116
aaaccgttac cattactgag tttagtaatg gtaacggttc tc    42

<210> SEQ ID NO 117
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 117
aaaccgttac cattactgag tttagtaatg gtaacggttc tc    42

<210> SEQ ID NO 118
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 118
aaaccgttac cattactgag tttagtaatg gtaacggttc tc    42

<210> SEQ ID NO 119
<211> LENGTH: 42
<212> TYPE: DNA

-continued

<213> ORGANISM: Artificial
<220> FEATURE:
<223> OTHER INFORMATION: pre-miR-451 DNA sequence

<400> SEQUENCE: 119
aaaccgttac cattactgag tttagtaatg gtaacggttc tc         42

<210> SEQ ID NO 120
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 120
aaaccgttac cattactgag tttagtaatg gtaacggttc tc         42

<210> SEQ ID NO 121
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 121
aaaccgttac cattactgag tttagtaatg gtaacggttc tc         42

<210> SEQ ID NO 122
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 122
aaaccgttac cattactgag tttagtaatg gtaatggttc tc         42

<210> SEQ ID NO 123
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 123
aaaccgttac cattactgag tttagtaatg gtaacggttc tc         42

<210> SEQ ID NO 124
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 124
aaaccgttac cattactgag tttagtaatg gtaacggttc tc         42

<210> SEQ ID NO 125
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 125
aaaccgttac cattactgag tttagtaatg gtaacggttc tc         42

<210> SEQ ID NO 126
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 126
aaaccgttac cattactgag tttagtaatg gtaatggttc tc                            42

<210> SEQ ID NO 127
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 127
aaaccgttac cattactgag tttagtaatg gtaatggttc tc                            42

<210> SEQ ID NO 128
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 128
aaaccgttac cattactgag tttagtaatg gtaatggttc tc                            42

<210> SEQ ID NO 129
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 129
aaaccgttac cattactgag tttagtaatg gtaacggttc tc                            42

<210> SEQ ID NO 130
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 130
aaaccgttac cattactgag tttagtaatg gtaacggttc tc                            42

<210> SEQ ID NO 131
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 131
aaaccgttac cattactgag tttagtaatg gtaacggttc tc                            42

<210> SEQ ID NO 132
<211> LENGTH: 42
<212> TYPE: DNA
<213> ORGANISM: Artificial
<220> FEATURE:

<223> OTHER INFORMATION: pre-miR-451 DNA sequence

<400> SEQUENCE: 132
aaaccgttac cattactgag tttagtaatg gtaacggttc tc                             42

<210> SEQ ID NO 133
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 133
aaaccgttac cattactgag tttagtaatg gtaacggttc tc                             42

<210> SEQ ID NO 134
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 134
aaaccgttac cattactgag tttagtaatg gtaacggttc tc                             42

<210> SEQ ID NO 135
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 135
aaaccgttac cattactgag tttagtaatg gtaatggttc tc                             42

<210> SEQ ID NO 136
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 136
aaaccgttac cattactgag tttagtaatg gtaacggttc tc                             42

<210> SEQ ID NO 137
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 137
aaaccgttac cattactgag tttagtaatg gtaacggttc tc                             42

<210> SEQ ID NO 138
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 138
aaaccgttac cattactgag tttagtaatg gtaacggttc tc                             42

```
<210> SEQ ID NO 139
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 139
aaaccgttac cattactgag tttagtaatg gtaacggttc tc                              42

<210> SEQ ID NO 140
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 140
aaaccgttac cattactgag tttagtaatg gtaacggttc tc                              42

<210> SEQ ID NO 141
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 141
aaaccgttac cattactgag tttagtaatg gtaacggttc tc                              42

<210> SEQ ID NO 142
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 142
aaaccgttac cattactgtg tttagtaatg gtaagggttc tc                              42

<210> SEQ ID NO 143
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 143
aaaccgttac cattactgtg cttagtaatg gtaagggttc tc                              42

<210> SEQ ID NO 144
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 144
aaaccgttac cattactgtg tttagtaatg gtaacggttc tc                              42

<210> SEQ ID NO 145
<211> LENGTH: 42
<212> TYPE: DNA
<213> ORGANISM: Artificial
<220> FEATURE:
<223> OTHER INFORMATION: pre-miR-451 DNA sequence
```

```
<400> SEQUENCE: 145
aaaccgtttc aattactgag tttagtaatg gtaacggttc tc                          42

<210> SEQ ID NO 146
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 146
aaaccgttac cattactgag tttagtaatg gtaatggttc t                           41

<210> SEQ ID NO 147
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 147
aaaccgttac cattactgag tttagtaatg gtaacggttc t                           41

<210> SEQ ID NO 148
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 148
aaaccgttac cattactgag tttagtaatg gtaacggttc t                           41

<210> SEQ ID NO 149
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 149
aaaccgttac cattactgag tttagtaatg gtaacggttc t                           41

<210> SEQ ID NO 150
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 150
aaaccgttac cattactgag tttagtaatg gtaacggttc t                           41

<210> SEQ ID NO 151
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 151
aaaccgttac cattactgag tttagtaatg gtaacggttc t                           41

<210> SEQ ID NO 152
<211> LENGTH: 41
```

```
<212> TYPE: DNA
<213> ORGANISM: Artificial
<220> FEATURE:
<223> OTHER INFORMATION: pre-miR-451 DNA sequence

<400> SEQUENCE: 152
aaaccgttac cattactgag tttagtaatg gtaacggttc t          41

<210> SEQ ID NO 153
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 153
aaaccgttac cattactgag tttagtaatg gtaacggttc t          41

<210> SEQ ID NO 154
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 154
aaaccgttac cattactgag tttagtaatg gtaacggttc t          41

<210> SEQ ID NO 155
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 155
aaaccgttac cattactgag tttagtaatg gtaatggttc t          41

<210> SEQ ID NO 156
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 156
aaaccgttac cattactgac tttagtaatg gtaacggttc t          41

<210> SEQ ID NO 157
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 157
aaaccgttac cattactgac tttagtaatg gtaacggttc t          41

<210> SEQ ID NO 158
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 158
```
aaaccgttac cattactgag tttagtaatg gtaagggttc tg    42

<210> SEQ ID NO 159
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 159
aaaccgttac cattactgaa tttagtaatg gtaagggttc tg    42

<210> SEQ ID NO 160
<211> LENGTH: 40
<212> TYPE: DNA
<213> ORGANISM: Artificial
<220> FEATURE:
<223> OTHER INFORMATION: pre-miR-451 DNA sequence

<400> SEQUENCE: 160
aaaccgttac cattactgag tttagtaatg gtaagggttc    40

<210> SEQ ID NO 161
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 161
aaaccgttac cattactgag tttagtaatg gtaagggttc tc    42

<210> SEQ ID NO 162
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 162
aaaccgttac cattactgag tttagtaatg gtaagggttc tt    42

<210> SEQ ID NO 163
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 163
aaaccgttac cattactgag tttagtaatg gtaagggttc t    41

<210> SEQ ID NO 164
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 164
aaaccgttac cattactgag tttagtaatg gtaagggttc t    41

<210> SEQ ID NO 165
<211> LENGTH: 41
<212> TYPE: DNA
<213> ORGANISM: Artificial

```
<220> FEATURE:
<223> OTHER INFORMATION: pre-miR-451 DNA sequence

<400> SEQUENCE: 165
aaaccgttac cattactgag tttagtaatg gtaagggttc t                         41

<210> SEQ ID NO 166
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 166
aaaccgttac cattactgag tttagtaatg gtaagggttc t                         41

<210> SEQ ID NO 167
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 167
aaaccgttac cattactgag tttagtaatg gtaagggttc ct                        42

<210> SEQ ID NO 168
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 168
aaaccgttac cattactgag tttagtaatg gtaagggttc tt                        42

<210> SEQ ID NO 169
<211> LENGTH: 41
<212> TYPE: DNA
<213> ORGANISM: Artificial
<220> FEATURE:
<223> OTHER INFORMATION: pre-miR-451 DNA sequence

<400> SEQUENCE: 169
aaaccgttac cattactgag tttagttatg gtaagggtta t                         41

<210> SEQ ID NO 170
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 170
aaaccgttac cattactgag tttagtaatg gtaagggttc ct                        42

<210> SEQ ID NO 171
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 171
aaaccgttac cattactgag tttagtaatg gtaagggttc tg                        42
```

```
<210> SEQ ID NO 172
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 172
aaaccgttac cattactgag tttagtaatg gtaagggttc tc                              42

<210> SEQ ID NO 173
<211> LENGTH: 42
<212> TYPE: DNA
<213> ORGANISM: Artificial
<220> FEATURE:
<223> OTHER INFORMATION: pre-miR-451 DNA sequence

<400> SEQUENCE: 173
aaaccgttac cattactgag cttagtaatg gtaagggtta tg                              42
```